US011186857B2

(12) United States Patent
Stoddart et al.

(10) Patent No.: US 11,186,857 B2
(45) Date of Patent: *Nov. 30, 2021

(54) POLYNUCLEOTIDE MODIFICATION METHODS

(71) Applicant: Oxford Nanopore Technologies Ltd., Oxford (GB)

(72) Inventors: David Jackson Stoddart, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 45 days.

This patent is subject to a terminal disclaimer.

(21) Appl. No.: 16/655,907

(22) Filed: Oct. 17, 2019

(65) Prior Publication Data

US 2020/0131549 A1 Apr. 30, 2020

Related U.S. Application Data

(63) Continuation of application No. 14/911,853, filed as application No. PCT/GB2014/052505 on Aug. 14, 2014, now Pat. No. 10,501,767.

(30) Foreign Application Priority Data

Aug. 16, 2013 (GB) ...................... 1314695

(51) Int. Cl.
*C12P 19/34* (2006.01)
*C12Q 1/6869* (2018.01)
*C12N 9/12* (2006.01)
*C12Q 1/68* (2018.01)

(52) U.S. Cl.
CPC ............ *C12P 19/34* (2013.01); *C12N 9/1241* (2013.01); *C12Q 1/68* (2013.01); *C12Q 1/6869* (2013.01); *C12Y 207/07* (2013.01)

(58) Field of Classification Search
CPC ......... C12P 19/34; C12Q 1/6869; C12Q 1/68; C12N 9/1241; C12Y 207/07
See application file for complete search history.

(56) References Cited

U.S. PATENT DOCUMENTS

| | | |
|---|---|---|
| 5,215,899 A | 6/1993 | Dattagupta |
| 5,424,413 A | 6/1995 | Hogan et al. |
| 5,561,043 A | 10/1996 | Cantor et al. |
| 5,777,078 A | 7/1998 | Bayley et al. |
| 5,795,782 A | 8/1998 | Church et al. |
| 5,817,771 A | 10/1998 | Bayley et al. |
| 5,866,328 A | 2/1999 | Bensimon et al. |
| 5,866,336 A | 2/1999 | Nazarenko et al. |
| 5,985,834 A | 11/1999 | Engel et al. |
| 6,015,714 A | 1/2000 | Baldarelli et al. |
| 6,087,099 A | 7/2000 | Gupte et al. |
| 6,123,819 A | 9/2000 | Peeters |
| 6,127,166 A | 10/2000 | Bayley et al. |
| 6,251,610 B1 | 6/2001 | Gupte et al. |
| 6,362,002 B1 | 3/2002 | Denison et al. |
| 6,403,319 B1 | 6/2002 | Lizardi et al. |
| 6,426,231 B1 | 7/2002 | Bayley et al. |
| 6,451,563 B1 | 9/2002 | Wittig et al. |
| 6,465,193 B2 | 10/2002 | Akeson et al. |
| 6,627,067 B1 | 9/2003 | Branton et al. |
| 6,787,308 B2 | 9/2004 | Balasubramanian et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,087,729 B1 | 8/2006 | Prive |
| 7,189,503 B2 | 3/2007 | Akeson et al. |
| 7,238,485 B2 | 7/2007 | Akeson et al. |
| 7,361,466 B2 | 4/2008 | Korlach et al. |
| 7,507,575 B2 | 3/2009 | Bedingham et al. |
| 7,700,281 B2 | 4/2010 | Kubu et al. |
| 8,105,846 B2 | 1/2012 | Bayley et al. |
| 8,143,030 B2 | 3/2012 | Maxham et al. |
| 8,343,746 B2 | 1/2013 | Rank et al. |
| 8,383,369 B2 | 2/2013 | Maxham et al. |
| 8,628,940 B2 | 1/2014 | Sorenson et al. |
| 8,652,779 B2 | 2/2014 | Turner et al. |
| 8,785,211 B2 | 7/2014 | Bayley et al. |
| 8,822,160 B2 | 9/2014 | Bayley et al. |
| 8,889,348 B2 | 11/2014 | Ju |

(Continued)

FOREIGN PATENT DOCUMENTS

| | | |
|---|---|---|
| CN | 101495656 | 7/2009 |
| CN | 102245760 | 11/2011 |
| DE | 112016000293 T5 | 9/2017 |
| EP | 2682460 A1 | 1/2014 |
| EP | 3470529 A1 | 4/2019 |

(Continued)

OTHER PUBLICATIONS

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

(Continued)

*Primary Examiner* — Cynthia B Wilder
(74) *Attorney, Agent, or Firm* — Wolf, Greenfield & Sacks, P.C.

(57) ABSTRACT

The invention relates to a method for modifying a template double stranded polynucleotide, especially for characterisation using nanopore sequencing. The method produces from the template a plurality of modified double stranded polynucleotides. These modified polynucleotides can then be characterised.

17 Claims, 24 Drawing Sheets

Specification includes a Sequence Listing.

(56) References Cited

U.S. PATENT DOCUMENTS

| | | | |
|---|---|---|---|
| 9,057,102 B2 | 6/2015 | Turner et al. |
| 9,116,118 B2 | 8/2015 | Turner et al. |
| 9,145,623 B2 | 9/2015 | Kavanagh et al. |
| 9,150,918 B2 | 10/2015 | Turner et al. |
| 9,542,527 B2 | 1/2017 | Travers et al. |
| 9,546,400 B2 | 1/2017 | Turner et al. |
| 9,551,023 B2 | 1/2017 | Turner et al. |
| 9,556,480 B2 | 1/2017 | Turner et al. |
| 9,582,640 B2 | 2/2017 | Travers et al. |
| 9,600,626 B2 | 3/2017 | Travers et al. |
| 9,670,526 B2 | 6/2017 | Kokoris et al. |
| 9,678,056 B2 | 6/2017 | Turner et al. |
| 9,738,929 B2 | 8/2017 | Turner et al. |
| 9,957,560 B2 | 5/2018 | Brown et al. |
| 10,131,944 B2 | 11/2018 | Bernick et al. |
| 10,221,450 B2 | 3/2019 | Heron et al. |
| 10,501,767 B2 | 12/2019 | Stoddart et al. |
| 10,570,440 B2 | 2/2020 | White et al. |
| 10,597,713 B2 | 3/2020 | Brown et al. |
| 10,669,578 B2 | 6/2020 | Clarke et al. |
| 10,851,409 B2 | 12/2020 | Brown et al. |
| 2001/0039039 A1 | 11/2001 | Weissman et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0132350 A1* | 9/2002 | Suzuki ............... C12N 15/8206 435/476 |
| 2002/0142331 A1 | 10/2002 | Fu et al. |
| 2002/0177701 A1 | 11/2002 | Weissman et al. |
| 2002/0197618 A1 | 12/2002 | Sampson |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0165936 A1 | 9/2003 | Rabbani et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0055901 A1 | 3/2004 | Petersen et al. |
| 2004/0214177 A1 | 10/2004 | Bension |
| 2004/0229315 A1 | 11/2004 | Lee et al. |
| 2005/0042633 A1 | 2/2005 | Williams |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0227239 A1 | 10/2005 | Joyce |
| 2005/0260655 A1 | 11/2005 | Liu et al. |
| 2006/0063171 A1 | 3/2006 | Akeson et al. |
| 2006/0086626 A1 | 4/2006 | Joyce |
| 2006/0141516 A1 | 6/2006 | Kobold et al. |
| 2006/0147935 A1 | 7/2006 | Linnarsson |
| 2006/0292611 A1 | 12/2006 | Berka et al. |
| 2007/0015182 A1 | 1/2007 | Abarzua |
| 2007/0020640 A1 | 1/2007 | McCloskey |
| 2007/0031857 A1 | 2/2007 | Makarov et al. |
| 2007/0122885 A1 | 5/2007 | Reeves et al. |
| 2007/0224613 A1 | 9/2007 | Strathmann |
| 2007/0269825 A1 | 11/2007 | Wang et al. |
| 2007/0287151 A1 | 12/2007 | Linnarsson |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0098612 A1 | 4/2009 | Rhee et al. |
| 2009/0256116 A1 | 10/2009 | Shumaker-Parry et al. |
| 2009/0269771 A1 | 10/2009 | Schroeder |
| 2009/0280538 A1 | 11/2009 | Patel et al. |
| 2009/0298075 A1 | 12/2009 | Travers et al. |
| 2010/0003560 A1 | 1/2010 | Shibata |
| 2010/0035260 A1 | 2/2010 | Olasagasti et al. |
| 2010/0075309 A1 | 3/2010 | Maxham et al. |
| 2010/0075327 A1 | 3/2010 | Maxham et al. |
| 2010/0092960 A1 | 4/2010 | Fehr |
| 2010/0120098 A1 | 5/2010 | Grunenwald et al. |
| 2010/0221212 A1 | 9/2010 | Stagliano et al. |
| 2010/0221716 A1 | 9/2010 | Flusberg et al. |
| 2010/0276588 A1 | 11/2010 | Syms |
| 2010/0331194 A1 | 12/2010 | Turner et al. |
| 2011/0019186 A1 | 1/2011 | Himmelhaus et al. |
| 2011/0124518 A1 | 5/2011 | Cantor |
| 2011/0136676 A1 | 6/2011 | Greene |
| 2011/0214991 A1 | 9/2011 | Kim et al. |
| 2011/0224106 A1 | 9/2011 | Eshoo et al. |
| 2011/0281768 A1 | 11/2011 | Travers et al. |
| 2011/0287435 A1* | 11/2011 | Grunenwald ...... C12N 15/1093 435/6.12 |
| 2011/0311965 A1 | 12/2011 | Maglia et al. |
| 2012/0010085 A1 | 1/2012 | Rava et al. |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0196279 A1 | 8/2012 | Underwood et al. |
| 2012/0244525 A1 | 9/2012 | Hendrickson |
| 2013/0017978 A1 | 1/2013 | Kavanagh et al. |
| 2013/0078624 A1 | 3/2013 | Holmes et al. |
| 2013/0143802 A1 | 6/2013 | Chilkoti |
| 2013/0195908 A1 | 8/2013 | Leonetti et al. |
| 2013/0327644 A1 | 12/2013 | Turner et al. |
| 2014/0134618 A1 | 5/2014 | Kokoris et al. |
| 2014/0134629 A1 | 5/2014 | Turner et al. |
| 2014/0186823 A1 | 7/2014 | Clarke et al. |
| 2014/0206842 A1 | 7/2014 | Majeed et al. |
| 2014/0262784 A1 | 9/2014 | Clarke et al. |
| 2014/0296089 A1 | 10/2014 | Holmes et al. |
| 2014/0308661 A1 | 10/2014 | Holmes et al. |
| 2015/0008126 A1 | 1/2015 | Maglia et al. |
| 2015/0045257 A1 | 2/2015 | Kavanagh et al. |
| 2015/0152492 A1 | 6/2015 | Brown et al. |
| 2015/0167075 A1 | 6/2015 | Turner et al. |
| 2015/0175663 A1 | 6/2015 | Yokoi et al. |
| 2015/0197796 A1 | 7/2015 | White et al. |
| 2015/0265994 A1 | 9/2015 | Hyde et al. |
| 2015/0285781 A1 | 10/2015 | Heron et al. |
| 2015/0307934 A1 | 10/2015 | Turner et al. |
| 2016/0010147 A1 | 1/2016 | Heron et al. |
| 2016/0010148 A1 | 1/2016 | Turner et al. |
| 2016/0011169 A1 | 1/2016 | Turner et al. |
| 2016/0194677 A1 | 7/2016 | Stoddart et al. |
| 2016/0257942 A1 | 9/2016 | Bruce et al. |
| 2016/0281159 A1 | 9/2016 | Brown et al. |
| 2016/0362739 A1 | 12/2016 | Brown et al. |
| 2017/0002406 A1 | 1/2017 | Bowen et al. |
| 2017/0067101 A1 | 3/2017 | Clarke et al. |
| 2017/0240955 A1 | 8/2017 | White |
| 2017/0314062 A1 | 11/2017 | Kokoris et al. |
| 2017/0321266 A1 | 11/2017 | Mckeown |
| 2018/0030506 A1 | 2/2018 | Fujioka |
| 2018/0291440 A1 | 10/2018 | Mckeown |
| 2018/0291441 A1 | 10/2018 | Brown et al. |
| 2019/0194722 A1 | 6/2019 | Stoddart et al. |
| 2019/0211390 A1 | 7/2019 | Heron et al. |
| 2019/0376132 A1 | 12/2019 | Mckeown |
| 2020/0002761 A1 | 1/2020 | Mckeown |
| 2020/0024655 A1 | 1/2020 | Brown et al. |
| 2020/0032248 A1 | 1/2020 | White et al. |
| 2020/0131549 A1 | 4/2020 | Stoddart et al. |
| 2020/0239950 A1 | 7/2020 | Brown et al. |
| 2020/0291452 A1 | 9/2020 | White |
| 2020/0318179 A1 | 10/2020 | Clarke et al. |

FOREIGN PATENT DOCUMENTS

| | | |
|---|---|---|
| GB | 2130219 | 5/1984 |
| GB | 2237390 | 5/1991 |
| GB | 2453377 | 4/2009 |
| JP | H11-137260 | 5/1999 |
| JP | 2012-506704 A | 3/2012 |
| WO | WO 1994/23065 | 10/1994 |
| WO | WO 1999/05167 | 2/1999 |
| WO | WO 2000/28312 | 5/2000 |
| WO | WO 2001/40516 | 6/2001 |

(56) References Cited

FOREIGN PATENT DOCUMENTS

| | | |
|---|---|---|
| WO | WO 2001/42782 | 6/2001 |
| WO | WO 2001/59453 | 8/2001 |
| WO | WO 2002/42496 | 5/2002 |
| WO | WO 2003/095669 | 11/2003 |
| WO | WO 2005/056750 | 6/2005 |
| WO | WO 2005/118877 | 12/2005 |
| WO | WO 2005/124888 | 12/2005 |
| WO | WO 2006/020775 | 2/2006 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/114693 A2 | 10/2007 |
| WO | WO 2007/146158 | 12/2007 |
| WO | WO 2008/045575 | 4/2008 |
| WO | WO 2008/083554 | 7/2008 |
| WO | WO 2008/102120 | 8/2008 |
| WO | WO 2008/102121 | 8/2008 |
| WO | WO 2008/124107 | 10/2008 |
| WO | WO 2009/035647 | 3/2009 |
| WO | WO 2009/044170 A1 | 4/2009 |
| WO | WO 2009/077734 A2 | 6/2009 |
| WO | WO 2009/120372 A2 | 10/2009 |
| WO | WO 2010/004265 | 1/2010 |
| WO | WO 2010/004273 | 1/2010 |
| WO | WO 2010/034018 | 3/2010 |
| WO | WO 2010/048605 A1 | 4/2010 |
| WO | WO 2010/051773 | 5/2010 |
| WO | WO 2010/086602 A1 | 8/2010 |
| WO | WO 2010/086603 | 8/2010 |
| WO | WO 2010/086622 | 8/2010 |
| WO | WO 2010/094040 | 8/2010 |
| WO | WO 2010/109107 A1 | 9/2010 |
| WO | WO 2010/109197 | 9/2010 |
| WO | WO 2010/122293 | 10/2010 |
| WO | WO 2010/146349 A1 | 12/2010 |
| WO | WO 2011/067559 | 6/2011 |
| WO | WO 2012/033524 A2 | 3/2012 |
| WO | WO 2012/061832 | 5/2012 |
| WO | WO 2012/083249 A2 | 6/2012 |
| WO | WO 2012/098561 A2 | 7/2012 |
| WO | WO 2012/098562 A2 | 7/2012 |
| WO | WO 2012/103545 A1 | 8/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/131962 A1 | 9/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/108810 A2 | 7/2014 |
| WO | WO 2014/135838 A1 | 9/2014 |
| WO | WO 2014/153408 | 9/2014 |
| WO | WO 2015/022544 A1 | 2/2015 |
| WO | WO 2015/031909 A1 | 3/2015 |
| WO | WO 2015/055981 A2 | 4/2015 |
| WO | WO 2015/056028 A1 | 4/2015 |
| WO | WO 2015/110777 A1 | 7/2015 |
| WO | WO 2015/110813 A1 | 7/2015 |
| WO | WO 2015/189636 A1 | 12/2015 |
| WO | WO 2015/200609 A1 | 12/2015 |
| WO | WO 2016/003814 A1 | 1/2016 |
| WO | WO 2016/022557 A1 | 2/2016 |
| WO | WO 2016/028887 A1 | 2/2016 |
| WO | WO 2016/059363 A1 | 4/2016 |
| WO | WO 2017/215500 A1 | 12/2017 |

OTHER PUBLICATIONS

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Berger et al., Universal bases for hybridization, replication and chain termination. Nucleic Acids Res. Aug. 1, 2000;28(15):2911-4.

Bowie et al., Deciphering the message in protein sequences: tolerance to amino acid substitutions. Science. Mar. 16, 1990;247(4948):1306-10.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

(56) References Cited

OTHER PUBLICATIONS

Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., 1994;116:6081-6088.
El-Sagheer et al., Synthesis and polymerase chain reaction amplification of DNA strands containing an unnatural triazole linkage. J Am Chem Soc. Mar. 25, 2009; 131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Genschel et al., Interaction of E. coli single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Hobbs et al., SSB protein limits RecOR binding onto single-stranded DNA. J Biol Chem. Apr. 13, 2007;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{ 1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.

(56) References Cited

OTHER PUBLICATIONS

Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Kozlov et al., Regulation of Single-stranded DNA Binding by the C Termini of *Esherichia coli* Single-stranded DNA-binding (SBB) Protein. J. Biol. Chem. May 28, 2010;285(22):17246-52.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Martin et al., Nanoscale protein pores modified with PAMAM dendrimers. J Am Chem Soc. Aug. 8, 2007;129(31):9640-9. Epub Jul. 18, 2007.
Martinez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Paner et al., Studies of DNA dumbbells. III. Theoretical analysis of optical melting curves of dumbbells with a 16 base-pair duplex stem and Tn end loops (n=2, 3, 4, 6, 8, 10, 14). Biopolymers. Jul. 1992;32(7):881-92.

(56) References Cited

OTHER PUBLICATIONS

Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Song et al., Structure of staphylococcal alpha-hemolysin, a heptameric transmembrane pore. Science. Dec. 13, 1996;274(5294):1859-66.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3+2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
U.S. Appl. No. 14/415,459, filed Jan. 16, 2015, Oxford et al., 2015-0197796.
U.S. Appl. No. 16/243,357, filed Jan. 9, 2019, Heron et al., 2019-0211390.
U.S. Appl. No. 15/179,802, filed Jun. 10, 2016, Brown et al., 2016-0281159.
U.S. Appl. No. 15/245,557, filed Aug. 24, 2016, Brown et al., 2016-0362739.
U.S. Appl. No. 15/944,365, filed Apr. 3, 2018, Brown et al., 2018-0291441.
U.S. Appl. No. 16/428,834, filed May 31, 2019, Brown et al.
U.S. Appl. No. 15/906,964, filed Feb. 27, 2018, McKeown, 2018-0291440.
U.S. Appl. No. 16/363,444, filed Mar. 25, 2019, McKeown, 2019-0376132.
U.S. Appl. No. 16/568,781, filed Sep. 12, 2019, McKeown.
U.S. Appl. No. 15/120,186, filed Aug. 19, 2016, Clarke et al., 2017-0067101.
U.S. Appl. No. 15/519,287, filed Apr. 14, 2017, White, 2017-0240955.
U.S. Appl. No. 16/304,114, filed Nov. 21, 2018, Stoddart et al., 2019-0194722.

(56) References Cited

OTHER PUBLICATIONS

U.S. Appl. No. 16/412,346, filed May 14, 2019, White, 2015-0197796.
PCT/GB2014/052505, Oct. 28, 2014, International Search Report and Written Opinion.
PCT/GB2014/052505, Feb. 25, 2016, International Preliminary Report on Patentability.
Cheng, et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7. Epub Jul. 3, 2007.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.
Faller et al., The structure of a mycobacterial outer-membrane channel. Science. Feb. 20, 2004;303(5661):1189-92. doi: 10.1126/science.1094114.
Gacillàn-Barcia et al., The diversity of conjugative relaxases and its application in plasmid classification. FEMS Microbiol Rev. May 2009;33(3):657-87.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.
He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.
Heron et al., Simultaneous measurement of ionic current and fluorescence from single protein pores. J Am Chem Soc. Feb. 11, 2009;131(5):1652-3. doi: 10.1021/ja808128s.
Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.
Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.
Ivanov et al., DNA tunneling detector embedded in a nanopore. Nano Lett. Jan. 12, 2011;11(1):279-85. doi: 10.1021/nl103873a. Epub Dec. 6, 2010.
Kozarewa et al., 96-plex molecular barcoding for the Illumina Genome Analyzer. Methods Mol Biol. 2011;733:279-98. doi: 10.1007/978-1-61779-089-8_20.
Kuipers, Random mutagenesis by using mixtures of dNTP and dITP in PCR. Methods Mol Biol. 1996;57:351-6. doi: 10.1385/0-89603-332-5:351.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Lee et al., Importance of the conserved CA dinucleotide at Mu termini. J Mol Biol. Nov. 30, 2001;314(3):433-44.
Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.
Lohman et al., Non-hexameric DNA helicases and translocases: mechanisms and regulation. Nat Rev Mol Cell Biol. May 2008;9(5):391-401. doi: 10.1038/nrm2394.
Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.
Ma et al., Bright functional rotaxanes. Chem Soc Rev. Jan. 2010;39(1):70-80. doi: 10.1039/b901710k. Epub Jul. 21, 2009.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
O'Shea et al., X-ray structure of the GCN4 leucine zipper, a two-stranded, parallel coiled coil. Science. Oct. 25, 1991;254(5031):539-44.
Pfeiffer et al., Bivalent cholesterol-based coupling of oligonucleotides to lipid membrane assemblies. J Am Chem Soc. Aug. 25, 2004;126(33):10224-5.
Remaut et al., Protein-protein interaction through beta-strand addition. Trends Biochem Sci. Aug. 2006;31(8):436-44. Epub Jul. 7, 2006.
Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.x. Epub Mar. 9, 2008.
Soni et al., Synchronous optical and electrical detection of biomolecules traversing through solid-state nanopores. Rev Sci Instrum. Jan. 2010;81(1):014301. doi: 10.1063/1.3277116.
Spee et al., Efficient random mutagenesis method with adjustable mutation frequency by use of PCR and dITP. Nucleic Acids Res. Feb. 11, 1993;21(3):777-8. doi: 10.1093/nar/21.3.777.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van Heel et al., Single-particle electron cryo-microscopy: towards atomic resolution. Q Rev Biophys. Nov. 2000;33(4):307-69.
Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011; 6(4): 253-260. EPub Feb. 20, 2011. doi: 10.1038/nnano.2011.12.

\* cited by examiner

POLYNUCLEOTIDE MODIFICATION METHODS

RELATED APPLICATIONS

This application is a Continuation of U.S. application Ser. No. 14/911,853, filed Feb. 12, 2016; which is a national stage filing under 35 U.S.C. § 371 of PCT/GB2014/052505, filed Aug. 14, 2014; which claims foreign priority benefits under 35 U.S.C. § 365(b) of British application number 1314695.6, filed Aug. 16, 2013. The entire contents of these applications are incorporated herein by reference in their entirety.

FIELD OF THE INVENTION

The invention relates to a method for modifying a template double stranded polynucleotide, especially for characterisation using nanopore sequencing. The method produces from the template a plurality of modified double stranded polynucleotides. These modified polynucleotides can then be characterised.

BACKGROUND OF THE INVENTION

There are many commercial situations which require the preparation of a nucleic acid library. This is frequently achieved using a transposase. Depending on the transposase which is used to prepare the library it may be necessary to repair the transposition events in vitro before the library can be used, for example in sequencing.

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to modify a template double stranded polynucleotide to produce a plurality of shorter, modified double stranded polynucleotides. The modified double stranded polynucleotides may include, for instance, a hairpin loop or a single stranded leader sequence. These modifications can be designed such that the modified double stranded polynucleotides are each easier to characterise, such as by strand sequencing, than the original template polynucleotide. Subsequent characterisation of the modified polynucleotides allows the character of the template polynucleotide to be more easily determined.

In one embodiment, the modification method uses a MuA transposase and a population of MuA substrates each comprising an overhang of universal nucleotides. Universal nucleotides are nucleotides which will hybridise to some degree to all of the nucleotides in the template polynucleotide. The MuA transposase is capable of fragmenting the template polynucleotide and producing fragments with overhangs at both ends. The MuA transposase is also capable of ligating a substrate to the overhang at one or both ends of the double stranded fragments. The strand of the substrate without an overhang is typically ligated to the strand of the fragment with an overhang. This leaves a single stranded gap in the resulting double stranded construct. Surprisingly, the overhang in the substrate containing the universal nucleotides is capable of hybridizing to the overhang in the strand of the fragment (to which the opposite strand in the substrate without the overhang is ligated) and closing the gap left by the action of the transposase (see FIG. 1). Ligating the overhang to the adjacent strand in the fragment produces a modified double stranded polynucleotide.

Accordingly, the invention provides a method for modifying a template double stranded polynucleotide, comprising:

(a) contacting the template polynucleotide with a MuA transposase and a population of double stranded MuA substrates each comprising at least one overhang of universal nucleotides such that the transposase fragments the template polynucleotide and ligates a substrate to one or both ends of the double stranded fragments and thereby producing a plurality of fragment/substrate constructs; and (b) ligating the overhangs to the fragments in the constructs and thereby producing a plurality of modified double stranded polynucleotides. In an alternative embodiment, the modification method uses a MuA transposase and a population of MuA substrates each comprising at least one overhang and at least one nucleotide in the same strand as the overhang which comprises a nucleoside that is not present in the template polynucleotide. The MuA transposase is capable of fragmenting the template polynucleotide. It is also capable of ligating a substrate to one or both ends of the double stranded fragments. The overhangs are then specifically removed from the ligated constructs using the at least one nucleotide which comprises a nucleoside that is not present in the template polynucleotide. This leaves gaps in the double stranded fragments and repairing these gaps provides a plurality of modified double stranded polynucleotides.

Accordingly, the invention also provides a method for modifying a template double stranded polynucleotide, comprising:

(a) contacting the template polynucleotide with a MuA transposase and a population of double stranded MuA substrates each comprising (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby producing a plurality of fragment/substrate constructs;

(b) removing the overhangs from the constructs by selectively removing the at least one nucleotide and thereby producing a plurality of double stranded constructs comprising single stranded gaps; and (c) repairing the single stranded gaps in the constructs and thereby producing a plurality of modified double stranded polynucleotides.

The invention also provides:
a plurality of polynucleotides modified using a method of the invention;
a population of double stranded polynucleotide substrates for modifying a template polynucleotide, wherein the substrates are as defined above;
a method of characterising at least one polynucleotide modified using a method of the invention, comprising a) contacting the modified polynucleotide with a transmembrane pore such that at least one strand of the polynucleotide moves through the pore and b) taking one or more measurements as the at least one strand moves with respect to the pore wherein the measurements are indicative of one or more characteristics of the at least one strand and thereby characterising the modified polynucleotide;
a method of characterising a template polynucleotide, comprising a) modifying the template polynucleotide using a method of the invention to produce a plurality of modified polynucleotides, b) contacting each modified polynucleotide with a transmembrane pore such that at least one strand of each polynucleotide moves through the pore and c) taking one or more measurements as the at least one strand of each polynucleotide moves with respect to the pore wherein the measurements are indicative of one or more characteristics of the at least one strand of each polynucleotide and thereby characterising the template polynucleotide; and
a kit for modifying a template polynucleotide comprising (a) a population of substrates as defined above and (b) a MuA transposase.

DESCRIPTION OF THE FIGURES

FIG. 20 (*b*) shows the Lambda DNA construct produced during the sample preparation procedure detailed in Example 3. The 5-10 kB fragment of Lambda DNA is labelled X, the fragment of DNA filled in by the polymerase and joined to the rest of the construct by the ligase is labelled y (and is shown as a dotted line) and the iSpC3 spacers are shown as x's. A tether sequence (SEQ ID NO: 39) was hybridised to the DNA construct as shown. Attached at the 3' end of SEQ ID NO: 39 was six iSp18 spacers attached to two thymine residues and a 3' cholesterol TEG (shown as a grey circle).

FIG. 23 (b) shows the Lambda DNA construct produced during the sample preparation procedure detailed in Example 4. The 5-10 kB fragment of Lambda DNA is labelled X, the inosines which have now been attached to x are labelled as a rectangle and the iSpC3 spacers are shown as x's. A tether sequence (SEQ ID NO: 39) was hybridised to the DNA construct as shown. Attached at the 3' end of SEQ ID NO: 39 was six iSp18 spacers attached to two thymine residues and a 3' cholesterol TEG (shown as a grey circle).

DESCRIPTION OF THE SEQUENCE LISTING

Figure 1:
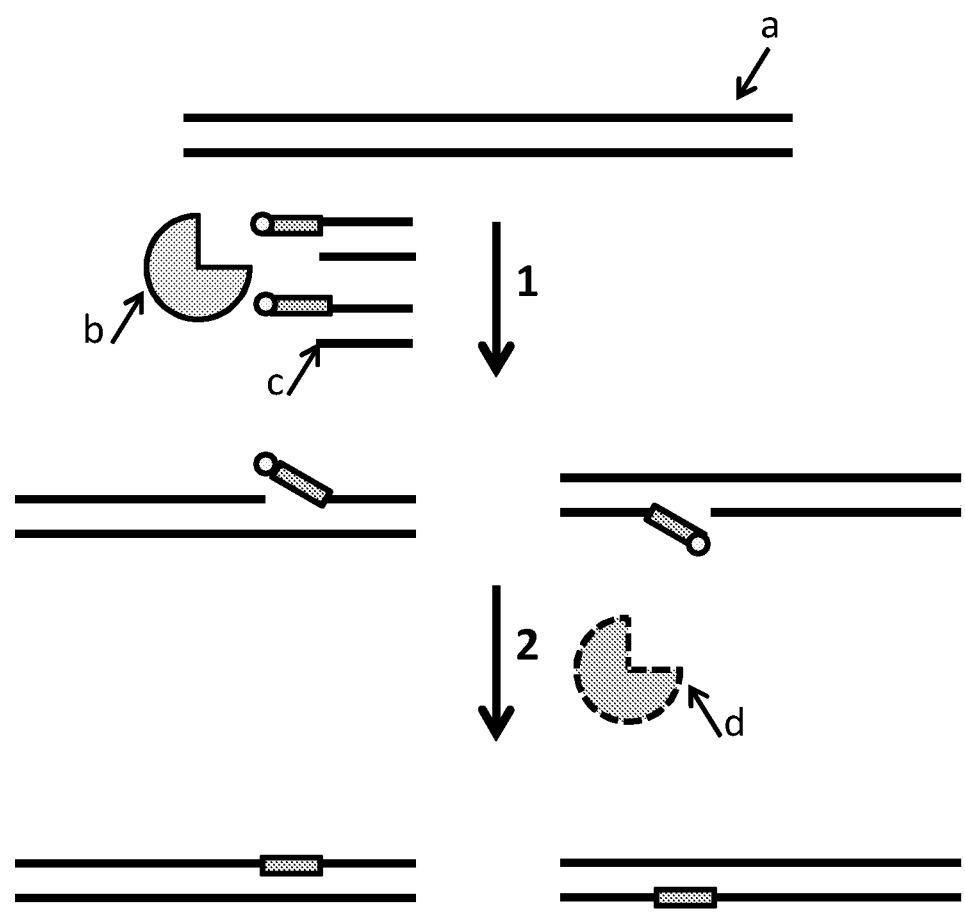
FIG. 1 shows a method of modifying a template double-stranded polynucleotide (a) by contacting the strand with a MuA transposase (b) and a population of double-stranded MuA substrates (c). The double stranded MuA substrates each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nick which is left in the fragmented double-stranded construct is then repaired using a DNA ligase (d), which ligates the strand containing the universal nucleotides to the double stranded construct (Step 2).
Figure 2:
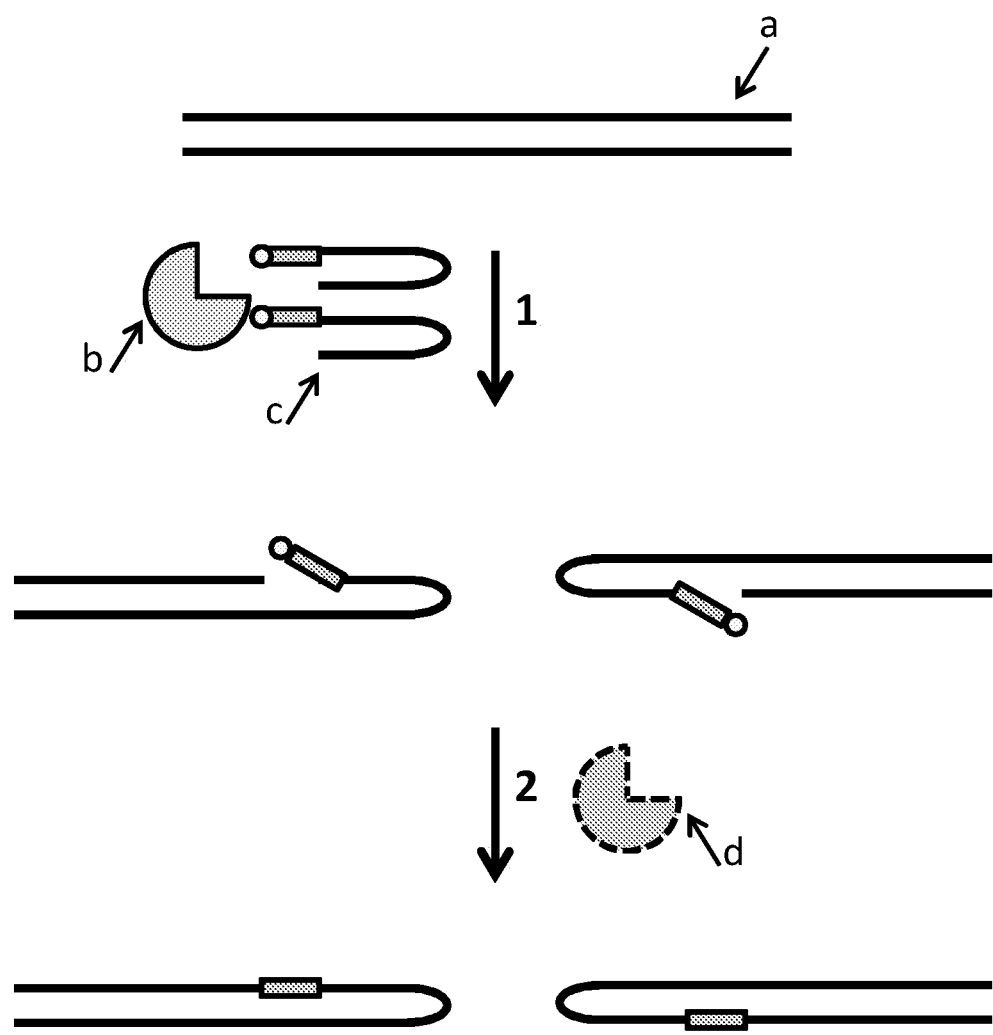
FIG. 2 shows a method of modifying a template double-stranded polynucleotide (a) by contacting the strand with a MuA transposase (b) and a population of double-stranded hairpin MuA substrates (c). The hairpin MuA substrates each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nick which is left in the fragmented double-stranded construct is then repaired using a DNA ligase (d), which ligates the strand containing the universal nucleotides to the double stranded construct (Step 2).

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of □-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOS: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the Hel308 motif of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the polynucleotide sequence of the double stranded portion of a MuA substrate of the invention. In Example 1 this sequence is attached to one end of a chain of four C3 spacer units by its 5' end. The opposite end of the chain of C3 spacer units is attached to the 3' end of SEQ ID NO: 27.

SEQ ID NO: 25 shows the polynucleotide sequence of the double stranded portion of a MuA substrate of the invention. This sequence is complementary to SEQ ID NO: 24 except that it contains a U at the 3' end.

SEQ ID NO: 26 shows polynucleotide sequence of the overhang strand of the double stranded MuA substrate of the invention. In Example 1 this sequence has a phosphate group attached to the 5' end of the sequence.

SEQ ID NO: 27 shows one of the polynucleotide sequences used in Example 1. It is attached to one end of a chain of four C3 spacer units by its 3' end. The opposite end of the chain of C3 spacer units is attached to the 5' end of SEQ ID NO: 24.

SEQ ID NO: 28 shows one of the polynucleotide sequences used in Example 1.

SEQ ID NO: 29 shows the polynucleotide sequence of the Enterobacteria phage λ. The sequence contains an additional 12 base overhang attached at the 5' end of the template strand. The sequence shown here is that of the template strand only.

SEQ ID NO: 30 shows one of the polynucleotide sequences used in Example 2.

SEQ ID NO: 31 shows one of the polynucleotide sequences used in Example 2.

SEQ ID NO: 32 shows one of the polynucleotide sequences used in Example 2. It has a phosphate group attached to the 5' end of the sequence.

SEQ ID NO: 33 shows the complementary polynucleotide sequence to SEQ ID NO: 30 used in Example 2.

SEQ ID NO: 34 shows part of a polynucleotide sequence used in Example 3 and 4. SEQ ID NO: 34 is attached at its 3' end to the 5' end of SEQ ID NO: 35 by four iSpC3 spacer units.

SEQ ID NO: 35 shows part of a polynucleotide sequence used in Example 3 and 4. In the Y-shaped MuA substrate of Examples 3 and 4 SEQ ID NO: 35 is attached at its 5' end to the 3' end of SEQ ID NO: 34 by four iSpC3 spacer units. In the hairpin loop of Example 3 SEQ ID NO: 35 is attached at its 5' end to the 3' end of SEQ ID NO: 36 by four iSpC3 spacers. In the hairpin MuA substrate of Example 4 SEQ ID NO: 35 is attached at its 5' end to the 3' end of SEQ ID NO: 41 by four iSpC3 spacers.

SEQ ID NO: 36 shows part of a polynucleotide sequence used in Example 3. In the Y-shaped MuA substrate SEQ ID NO: 36 is attached at its 3' end to the 5' end of SEQ ID NO: 37 by four iSpC3 spacer units. In the hairpin MuA substrate SEQ ID NO: 36 is attached at the 3' end to the 5' end of SEQ ID NO: 35 by four iSpC3 spacers.

SEQ ID NO: 37 shows part of a polynucleotide sequence used in Example 3 and 4. In Example 3 SEQ ID NO: 37 is attached at its 5' end to the 3' end of SEQ ID NO: 36 by four iSpC3 spacer units. In Example 4 SEQ ID NO: 37 is attached at its 5' end to the 3' end of SEQ ID NO: 41 by four iSpC3 spacer units.

SEQ ID NO: 38 shows part of a polynucleotide sequence used in Example 3.

SEQ ID NO: 39 shows a polynucleotide sequence used in Example 3 and 4 which at the 3' end of the sequence has six iSp18 spacers attached to two thymine residues and a 3' cholesterol TEG.

SEQ ID NO: 40 shows the amino acid sequence of the Trwc Cba helicase.

SEQ ID NO: 41 shows part of a polynucleotide sequence used in Example 4. In the Y-shaped MuA substrate SEQ ID NO: 41 is attached at its 3' end to the 5' end of SEQ ID NO: 37 by four iSpC3 spacer units. In the hairpin MuA substrate SEQ ID NO: 41 is attached at its 3' end to the 5' end of SEQ ID NO: 35 by four iSpC3 spacer units. This sequence has a phosphate attached to its 5' end and 5 deoxyinosines at positions 1 to 5 indicated in the sequence by an I.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes "polynucleotides", reference to "a substrate" includes two or more such substrates, reference to "a transmembrane protein pore" includes two or more such pores, and the like.

All publications, patents and patent applications cited herein, whether supra or infra, are hereby incorporated by reference in their entirety.

Modification Method of the Invention

The present invention provides a method of modifying a template polynucleotide. The template may be modified for any purpose. The method is preferably for modifying a template polynucleotide for characterisation, such as for strand sequencing. The template polynucleotide is typically the polynucleotide that will ultimately be characterised, or sequenced, in accordance with the invention. This is discussed in more detail below.

The method involves the formation of a plurality of modified double stranded polynucleotides. These modified double stranded polynucleotides are typically easier to characterise than the template polynucleotide, especially using strand sequencing. The plurality of modified double stranded polynucleotides may themselves be characterised in order to facilitate the characterisation of the template polynucleotide. For instance, the sequence of the template polynucleotide can be determined by sequencing each of the modified double stranded polynucleotides.

The modified double stranded polynucleotides are shorter than the template polynucleotide and so it is more straightforward to characterise them using strand sequencing.

The modified double strand polynucleotides can be selectively labelled by including the labels in the MuA substrates. Suitable labels include, but are not limited to, calibration sequences, coupling moieties and adaptor bound enzymes.

In some embodiments, the method introduces into the double stranded polynucleotides modifications which facilitate their characterisation using strand sequencing. It is well-established that coupling a polynucleotide to the membrane containing the nanopore lowers by several orders of magnitude the amount of polynucleotide required to allow its characterisation or sequencing. This is discussed in International Application No. PCT/GB2012/051191 (published as WO 2012/164270). The method of the invention allows the production of a plurality of double stranded polynucleotides each of which include a means for coupling the polynucleotides to a membrane. This is discussed in more detail below.

The characterisation of double stranded polynucleotides using a nanopore typically requires the presence of a leader sequence designed to preferentially thread into the nanopore. The method of the invention allows the production of a plurality of double stranded polynucleotides each of which include a single stranded leader sequence. This is discussed in more detail below.

It is also well established that linking the two strands of a double stranded polynucleotide by a bridging moiety, such as hairpin loop, allows both strands of the polynucleotide to be characterised or sequenced by a nanopore. This is advantageous because it doubles the amount of information obtained from a single double stranded polynucleotide. Moreover, because the sequence in the template complement strand is necessarily orthogonal to the sequence of the template strand, the information from the two strands can be combined informatically. Thus, this mechanism provides an orthogonal proof-reading capability that provides higher confidence observations. This is discussed in International Application No. PCT/GB2012/051786 (published as WO 2013/014451). The method of the invention allows the production of a plurality of modified double stranded polynucleotides in which the two strands of each polynucleotide are linked using a hairpin loop.

Template Polynucleotide

The method of the invention modifies a template double stranded polynucleotide, preferably for characterisation. The template polynucleotide is typically the polynucleotide that will ultimately be characterised, or sequenced, in accordance with the invention. It may also be called the target double stranded polynucleotide or the double stranded polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the template polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The template double stranded polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide is preferably a deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP.

The template double stranded polynucleotide preferably comprises the following nucleotides: dAMP, dUMP and/or dTMP, dGMP and dCMP.

A nucleotide may be abasic (i.e. lack a nucleobase). A nucleotide may also lack a nucleobase and a sugar (i.e. is a C3 spacer).

The nucleotides in the template polynucleotide may be attached to each other in any manner. The nucleotides are typically attached by their sugar and phosphate groups as in nucleic acids. The nucleotides may be connected via their nucleobases as in pyrimidine dimers.

The template polynucleotide is double stranded. The template polynucleotide may contain some single stranded regions, but at least a portion of the template polynucleotide is double stranded.

The template polynucleotide can be a nucleic acid, such as deoxyribonucleic acid (DNA) or ribonucleic acid (RNA). The template polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The template polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

MuA and Conditions

The template polynucleotide is contacted with a MuA transposase. This contacting occurs under conditions which allow the transposase to function, i.e. to fragment the template polynucleotide and to ligate MuA substrates to the one or both ends of the fragments. MuA transposase is commercially available, for instance from Thermo Scientific (Catalogue Number F-750 C, 20 μL (1.1 μg/μL)). Conditions under which MuA transposase will function are known in the art. Suitable conditions are described in the Examples.

Population of Substrates

The template polynucleotide is contacted with a population of double stranded MuA substrates. The double stranded substrates are polynucleotide substrates and may be formed from any of the nucleotides or nucleic acids discussed above. The substrates are typically formed from the same nucleotides as the template polynucleotide, except for the universal nucleotides or at least one nucleotide which comprises a nucleoside that is not present in the template polynucleotide.

The population of substrates is typically homogenous (i.e. typically contains a plurality of identical substrates). The population of substrates may be heterogeneous (i.e. may contain a plurality of different substrates).

Suitable substrates for a MuA transposase are known in the art (Saariaho and Savilahti, Nucleic Acids Research, 2006; 34(10): 3139-3149 and Lee and Harshey, J. Mol. Biol., 2001; 314: 433-444).

Each substrate typically comprises a double stranded portion which provides its activity as a substrate for MuA transposase. The double stranded portion is typically the same in each substrate. The population of substrates may comprise different double stranded portions.

The double stranded portion in each substrate is typically at least 50 nucleotide pairs in length, such as at least 55, at least 60 or at least 65 nucleotide pairs in length. The double stranded portion in each substrate preferably comprises a dinucleotide comprising deoxycytidine (dC) and deoxyadenosine (dA) at the 3' end of each strand. The dC and dA are typically in different orientations in the two strands of the double stranded portion, i.e. one strand has dC/dA and the other strand has dA/dC at the 3' end when reading from 5' to 3'.

One strand of the double stranded portion preferably comprises the sequence shown in SEQ ID NO: 24 and the other strand of the double stranded portion preferably comprises a sequence which is complementary to the sequence shown in SEQ ID NO: 24.

Universal Nucleotides

In one embodiment, the method comprises contacting the template polynucleotide with a population of double stranded MuA substrates each comprising at least one overhang of universal nucleotides. Each substrate preferably comprises a double stranded portion which comprises the sequence shown in SEQ ID NO: 24 hybridised to a sequence which is complementary to the sequence shown in SEQ ID NO: 24. The at least one overhang is preferably at the 5' end of the sequence which is complementary to the sequence shown in SEQ ID NO: 24.

Each substrate comprises at least one overhang of universal nucleotides. The overhang consists of universal nucleotides. There may be an overhang of universal nucleotides at one or both ends of each substrate. If there is an overhang at both ends of a substrate, each overhang is typically on different strands of the double stranded polynucleotide portion. Overhangs are preferably located at the 5' end of a strand of the double stranded portion.

Each substrate preferably comprises only one overhang. The only one overhang is preferably at the 5' end of one strand of the double stranded portion.

The overhang may be at least 3, at least 4, at least 5, at least 6 or at least 7 nucleotides in length. The overhang is preferably 5 nucleotides in length.

A universal nucleotide is one which will hybridise to some degree to all of the nucleotides in the template polynucleotide. A universal nucleotide is preferably one which will hybridise to some degree to nucleotides comprising the nucleosides adenosine (A), thymine (T), uracil (U), guanine (G) and cytosine (C). The universal nucleotide may hybridise more strongly to some nucleotides than to others. For instance, a universal nucleotide (I) comprising the nucleoside, 2'-deoxyinosine, will show a preferential order of pairing of I-C>I-A>I-G approximately =I-T. For the purposes of the invention, it is only necessary that the universal nucleotide used in the oligomers hybridises to all of the nucleotides in the template polynucleotide.

The universal nucleotide preferably comprises one of the following nucleobases: hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole or phenyl (C6-aromatic ring. The universal nucleotide more preferably comprises one of the following nucleosides: 2'-deoxyino sine, inosine, 7-deaza-2'-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside or phenyl C-2'-deoxyribosyl nucleoside. The universal nucleotide is most preferably comprises 2'-deoxyinosine.

The universal nucleotides in each overhang may be different from one another. The universal nucleotides in each overhang are preferably the same. All of the universal nucleotides in the population of substrates are preferably the same universal nucleotide.

The method of the invention preferably comprises (a) contacting the template polynucleotide with a MuA transposase and a population of double stranded MuA substrates each comprising at least one overhang of universal nucleotides such that the transposase fragments the template polynucleotide into fragments having an overhang at one or both ends and ligates a substrate strand without an overhang to an overhang at one or both ends of the double stranded fragments and thereby producing a plurality of fragment/substrate constructs;

(b) allowing the substrate overhangs to hybridise to the fragments overhangs in the constructs; and (b) ligating the substrate overhangs to the adjacent fragment strands in the constructs and thereby producing a plurality of modified double stranded polynucleotides.

The overhang(s) of universal nucleotides may further comprise a reactive group, preferably at the 5' end. The reactive group may be used to ligate the overhangs to the fragments in the constructs as discussed below. The reactive group may be used to ligate the fragments to the overhangs using click chemistry. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined the set of stringent criteria for click chemistry as follows: "The reaction must be modular, wide in scope, give very high yields, generate only inoffensive by-products that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by nonchromatographic methods, such as crystallization or distillation, and the product must be stable under physiological conditions".

Suitable examples of click chemistry include, but are not limited to, the following:
  (a) copper-free variant of the 1,3 dipolar cycloaddition reaction, where an azide reacts with an alkyne under strain, for example in a cyclooctane ring;
  (b) the reaction of an oxygen nucleophile on one linker with an epoxide or aziridine reactive moiety on the other; and
  (c) the Staudinger ligation, where the alkyne moiety can be replaced by an aryl phosphine, resulting in a specific reaction with the azide to give an amide bond.

Any reactive group may be used in the invention. The reactive group may be one that is suitable for click chemistry. The reactive group may be any of those disclosed in International Application No. PCT/GB10/000132 (published as WO 2010/086602), particularly in Table 3 of that application.

In a further embodiment, the modification method uses a MuA transposase and a population of MuA substrates each comprising at least one overhang comprising a reactive group. The overhang(s) may be any length and may comprise any combination of any nucleotide(s). Suitable lengths and nucleotides are disclosed above. Suitable reactive groups are discussed above. Accordingly, the invention provides a method for modifying a template double stranded polynucleotide, comprising:
  (a) contacting the template polynucleotide with a MuA transposase and a population of double stranded MuA substrates each comprising at least one overhang comprising a reactive group such that the transposase fragments the template polynucleotide and ligates a substrate to one or both ends of the double stranded fragments and thereby producing a plurality of fragment/substrate constructs; and
  (b) ligating the overhangs to the fragments in the constructs using the reactive group and thereby producing a plurality of modified double stranded polynucleotides.

Nucleosides that are not Present in the Template Polynucleotide

In one embodiment, the method comprises contacting the template polynucleotide with a population of double stranded MuA substrates each comprising (i) at least one overhang and (ii) at least one nucleotide in the same strand as the at least one overhang which comprises a nucleoside that is not present in the template polynucleotide.

As discussed above, the double stranded portion in each substrate preferably comprises a dinucleotide comprising deoxycytidine (dC) and deoxyadenosine (dA) at the 3' end of each strand. In some embodiments, one or both of the nucleotides in the dC and dA dinucleotide of one strand may be replaced with a nucleotide comprising a nucleoside that is not present in the template polynucleotide as discussed below. In a preferred embodiment, the template polynucleotide comprises deoxyadenosine (dA), thymidine (dT), deoxyguanosine (dG) and deoxycytidine (dC), but not deoxyuridine (dU) and the dA in the dC and dA dinucleotide of one strand is replaced with a nucleotide comprising deoxyuridine (dU). This is exemplified below.

One strand of the double stranded portion preferably comprises the sequence shown in SEQ ID NO: 24 and the other strand of the double stranded portion preferably comprises a sequence which is complementary to the sequence shown in SEQ ID NO: 24 and which is modified to include at least one nucleotide that is not present in the template polynucleotide. This "other strand" further comprises the overhang. In a more preferred embodiment, one strand of the double stranded portion comprises the sequence shown in SEQ ID NO: 24 and the other strand of the double stranded portion comprises the sequence shown in SEQ ID NO: 25 (see below). In SEQ ID NO: 25, the dA in the dC and dA dinucleotide at the 3' end had been replaced with dU. This double stranded portion (shown below) may be used when the template polynucleotide comprises deoxyadenosine (dA), thymidine (dT), deoxyguanosine (dG) and deoxycytidine (dC), but not deoxyuridine (dU).

```
                                          (SEQ ID NO: 24)
5'-GTTTTCGCATTTATCGTGAAACGCTTTCGCGTTTTTCGTGCGCCGCT
TCA-3'

(SEQ ID NO: 25)
3'-CAAAAGCGTAAATAGCACTTTGCGAAAGCGCAAAAAGCACGCGGCGA
AGU-5'
```

Each substrate comprises at least one overhang. The overhang is typically a nucleotide overhang. There may be an overhang at one or both ends of each substrate. If there is an overhang at both ends of a substrate, each overhang is typically on different strand of the double stranded polynucleotide portion and each strand typically comprises a nucleoside that is not present in the template polynucleotide. Overhangs are preferably located at the 5' end of a strand of the double stranded portion.

Each substrate preferably comprises only one overhang. The only one overhang is preferably at the 5' end of one strand of the double stranded portion. This is exemplified below.

The overhang may be at least 3, at least 4, at least 5, at least 6 or at least 7 nucleotides in length. The overhang is preferably 4 nucleotides in length. The overhang may comprise any of the nucleotides discussed above.

Each substrate comprises at least one nucleotide in the same strand as the overhang which comprises a nucleoside that is not present in the template polynucleotide. Such nucleotide(s) may be present in one or both strands of the substrates as discussed above. Each substrate may comprise any number of nucleotides which comprise a nucleoside that is not present in the template polynucleotide, such as 2, 3, 4, 5, 6, 7, 8, 9, 10 or more. If a substrate comprises more than one nucleotide that is not present in the template polynucleotide, those nucleotides are typically the same, but may be different.

If the template polynucleotide comprises deoxyadenosine (dA), thymidine (dT), deoxyguanosine (dG) and deoxycytidine (dC) but not deoxyuridine (dU), the nucleoside that is not present in the template polynucleotide is preferably deoxyuridine (dU).

In a preferred embodiment, one strand of the double stranded portion comprises the sequence shown in SEQ ID NO: 24 and the other strand of the double stranded portion comprises the sequence shown in SEQ ID NO: 25 (see above). In SEQ ID NO: 25, the dA in the dC and dA dinucleotide at the 3' end had been replaced with dU. The overhang is at the 5' end of SEQ ID NO: 25, i.e. attached to the U.

In a most preferred embodiment, one strand of the substrate comprises the sequence shown in SEQ ID NO: 24 and the other strand of the substrate comprises the sequence shown in SEQ ID NO: 26 (see below). This substrate (shown below) may be used when the template polynucleotide comprises deoxyadenosine (dA), thymidine (dT), deoxyguanosine (dG) and deoxycytidine (dC), but not deoxyuridine (dU).

(SEQ ID NO: 24)
5'-GTTTTCGCATTTATCGTGAAACGCTTTCGCGTTTTTCGTGCGCCGCT
TCA-3'

(SEQ ID NO: 26)
3'-CAAAAGCGTAAATAGCACTTTGCGAAAGCGCAAAAAGCACGCGGCGA
AGUCTAG-5'

If the template polynucleotide comprises deoxyadenosine (dA), deoxyuridine (dU), deoxyguanosine (dG) and deoxycytidine (dC) but not thymidine (dT), the nucleoside that is not present in the template polynucleotide is preferably thymidine (dT).

The nucleoside that is not present in the template polynucleotide is preferably abasic, adenosine (A), uridine (U), 5-methyluridine (m⁵U), cytidine (C) or guanosine (G) or preferably comprises urea, 5, 6 dihydroxythymine, thymine glycol, 5-hydroxy-5 methylhydanton, uracil glycol, 6-hydroxy-5, 6-dihdrothimine, methyltartronylurea, 7, 8-dihydro-8-oxoguanine (8-oxoguanine), 8-oxoadenine, fapyguanine, methy-fapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer.

The at least one nucleotide is preferably 10 nucleotides or fewer from the overhang, such as 9, 8, 7, 6, 5, 4, 3, 2, 1 or 0 nucleotides from the overhang. In other words, the at least one nucleotide is preferably at any of positions A to K in the Example below. The at least one nucleotide is preferably 0 nucleotides from the overhang (i.e. is adjacent to the overhang). In other words, the at least one nucleotide is preferably at position K in the Example below.

ABCDEFGHIJKXXXX

XXXXXXXXXX

The at least one nucleotide may be the first nucleotide in the overhang. In other words, the at least one nucleotide may be at position A in the Example below.

XXXXXXXXXXAXXX

XXXXXXXXXX

All of the nucleotides in the overhang may comprise a nucleoside that is not present in the template polynucleotide. A person skilled in the art is capable of designing suitable substrates.

The method of the invention preferably comprises
(a) contacting the template polynucleotide with a MuA transposase and a population of double stranded MuA substrates each comprising (i) at least one overhang and (ii) at least one nucleotide in the same strand as the at least one overhang which comprises a nucleoside that is not present in the template polynucleotide such that the transposase fragments the template polynucleotide into fragments having an overhang at one or both ends and ligates a substrate strand without an overhang to an overhang at one or both ends of the double stranded fragments and thereby producing a plurality of fragment/substrate constructs;
(b) removing the overhangs from the constructs by selectively removing the at least one nucleotide and thereby producing a plurality of double stranded constructs comprising single stranded gaps; and
(c) repairing the single stranded gaps in the constructs and thereby producing a plurality of modified double stranded polynucleotides.

Preferred Substrates

In a preferred embodiment, each substrate comprises an overhang at one end and a leader sequence and/or a means for coupling to a membrane at the other. If a substrate comprises a leader sequence and a coupling means, each is typically located on a different strand of the double stranded portion. This results in the production of a plurality of modified double stranded polynucleotides which comprise the leader sequence and/or the means for coupling. Such polynucleotides have the advantages discussed above.

The leader sequence is typically a polynucleotide such as DNA or RNA, a modified polynucleotide (such as abasic DNA), PNA, LNA, PEG or a polypeptide. The leader is preferably a polynucleotide and is more preferably a single stranded polynucleotide. The leader sequence can be any of the polynucleotides discussed above. The single stranded leader sequence is most preferably a single strand of DNA. The leader sequence typically comprises nucleotides that are present in the template polynucleotide. The leader sequence typically does not comprise the nucleoside whose selective removal is used to remove the overhangs in accordance with the invention. The leader sequence can be any length, but is typically 27 to 150 nucleotides in length, such as from 50 to 150 nucleotides in length.

Means for coupling the modified double stranded polynucleotides to a membrane are discussed in more detail below.

Each substrate preferably comprises an overhang at one end and a hairpin loop at the other end. This results in the production of modified double stranded polynucleotides in step (c) which are linked by the hairpin loop at one or both ends. An example of this is shown in FIGS. 2, 7, 9 and 14. A person skilled in the art is capable of preparing hairpin loops using any of the nucleotides discussed above. The hairpin loop typically comprises the same nucleotides as in the template polynucleotide. The hairpin loop typically does not comprise the nucleoside whose selective removal is used to remove the overhangs in accordance with the invention.

Figure 3:
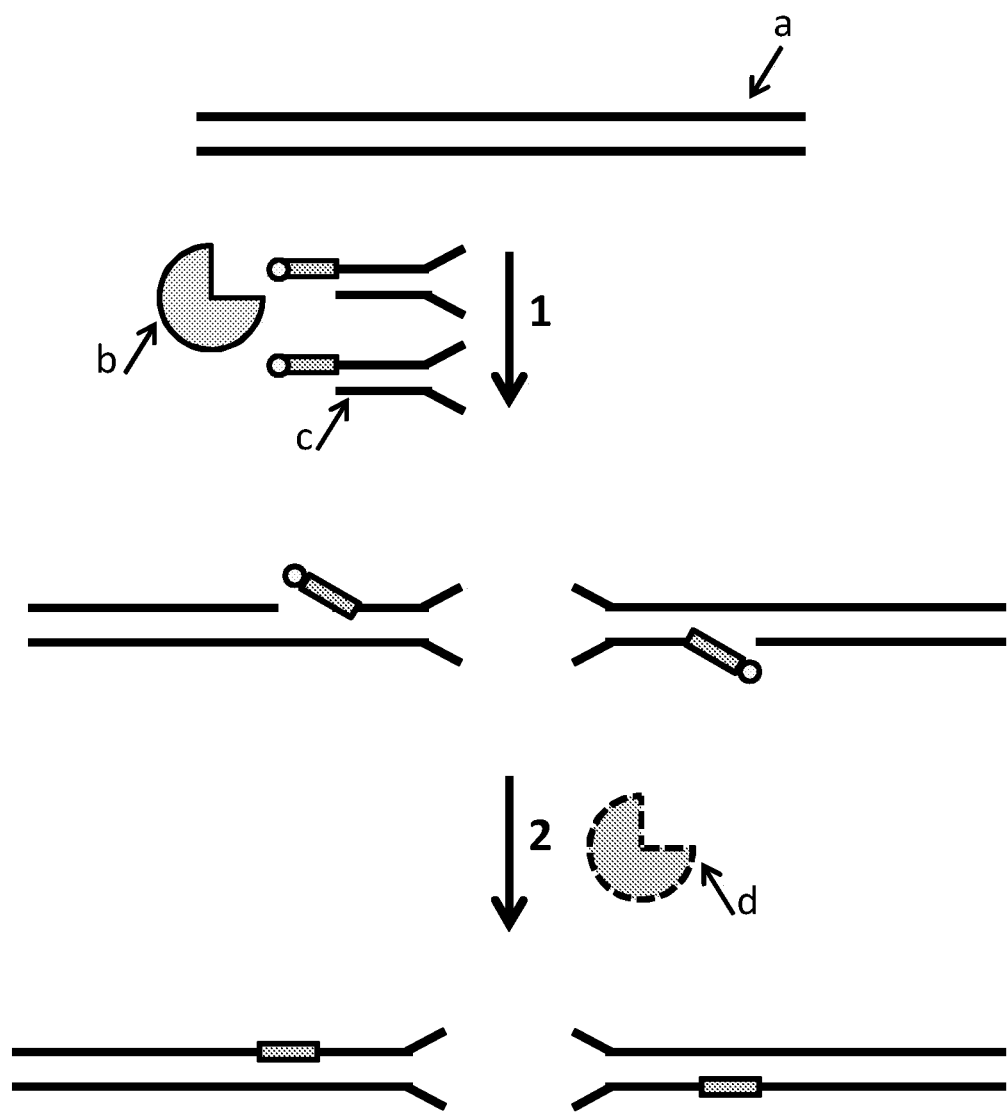
FIG. 3 shows a method of modifying a template double-stranded polynucleotide (a) by contacting the strand with a MuA transposase (b) and a population of Y-shaped MuA substrates (c). The Y-shaped MuA substrates each contain a 5'phosphate (labelled as a circle) and five universal nucleotides (labelled as a rectangle). The MuA transposase fragments the template double-stranded polynucleotide and inserts the Y-shaped MuA substrate at each side of the point of fragmentation (Step 1). The nick which is left in the fragmented double-stranded construct is then repaired using a DNA ligase (d), which ligates the strand containing the universal nucleotides to the double stranded construct (Step 2).
Figure 4:
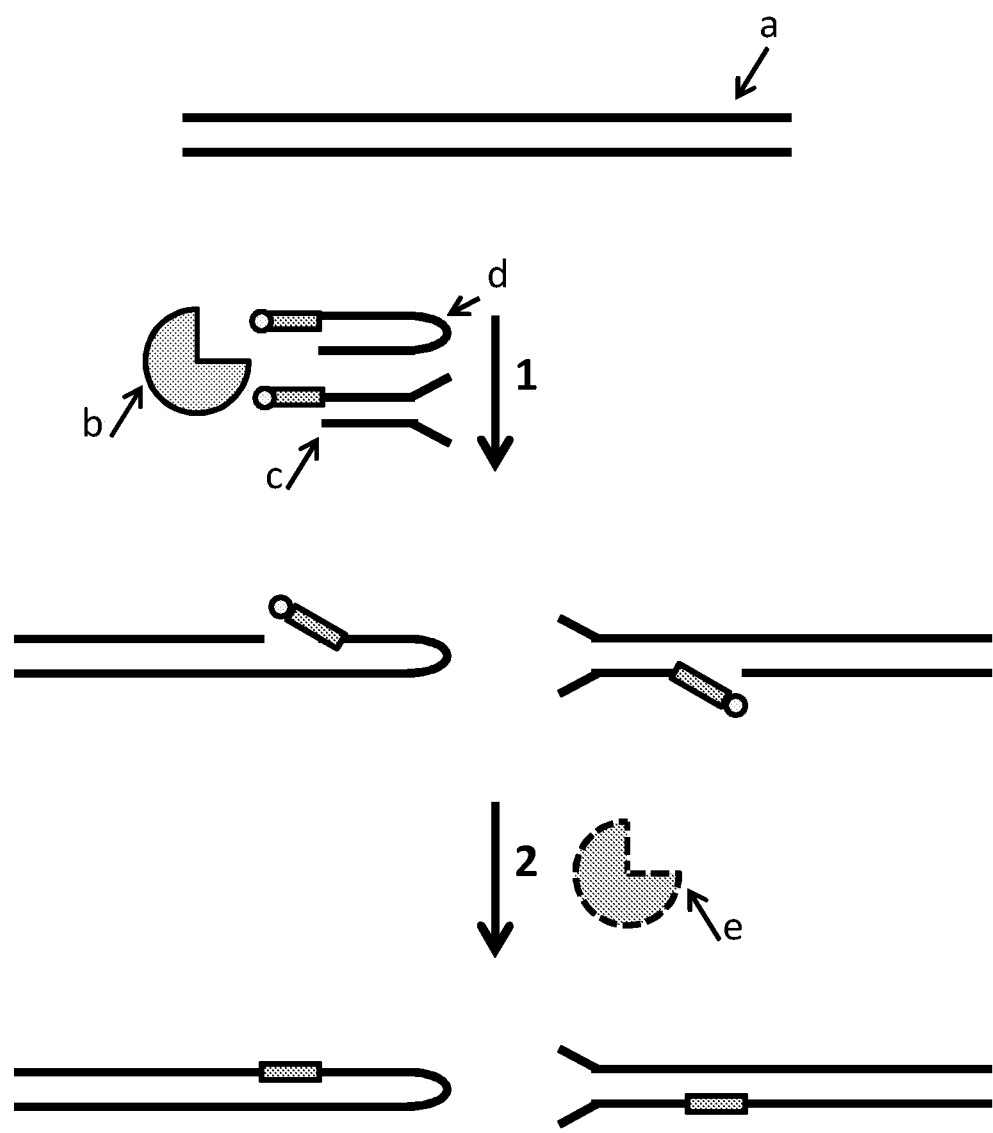
FIG. 4 shows a method of modifying a template double-stranded polynucleotide (a) by contacting the strand with a MuA transposase (b) and a population of double-stranded hairpin MuA substrates (d) and Y-shaped MuA substrates (c). Both types of MuA substrate each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nick which is left in the fragmented double-stranded construct is then repaired using a DNA ligase (e), which ligates the strand containing the universal nucleotides to the double stranded construct (Step 2).
Figure 10:
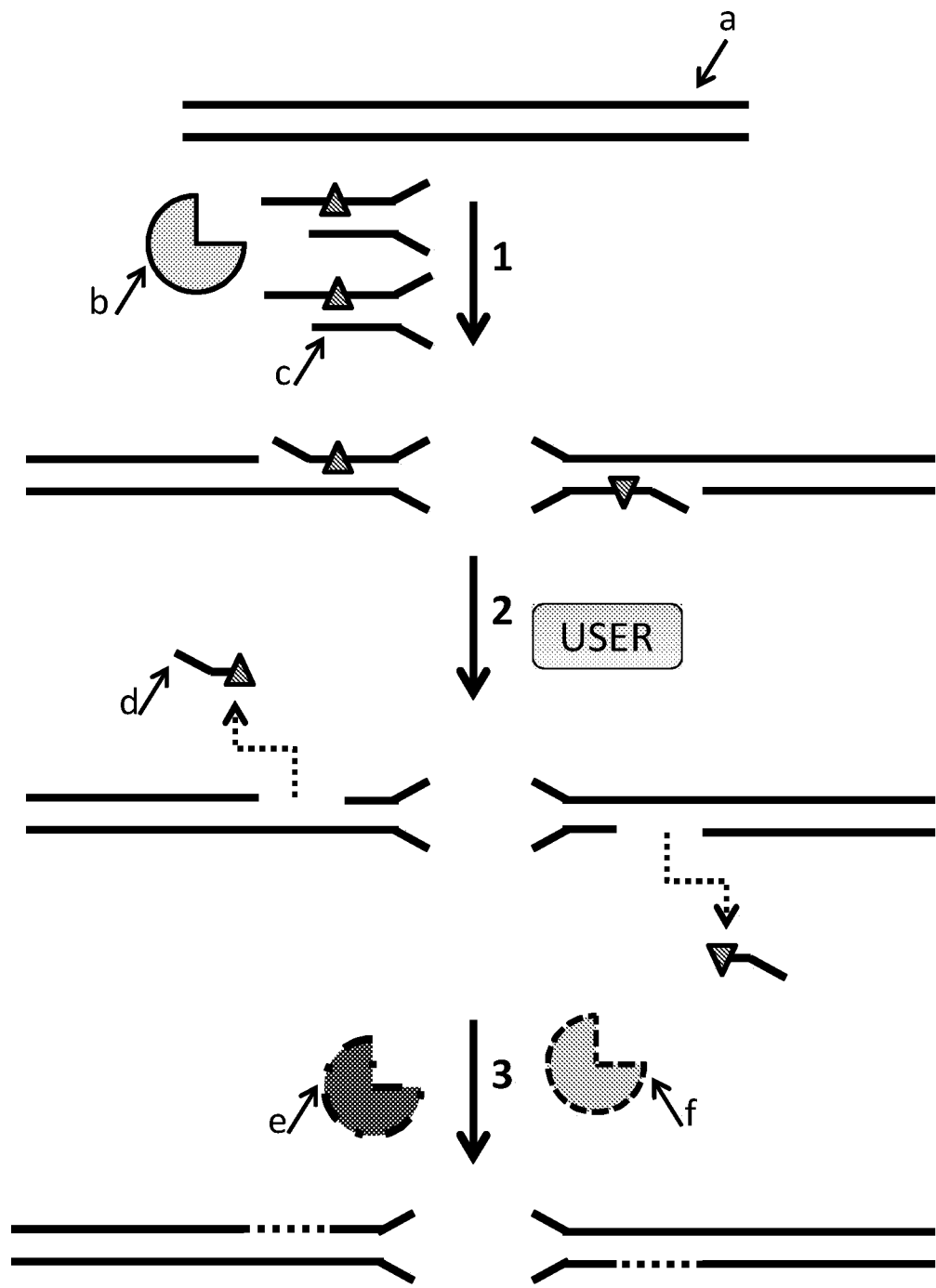
FIG. 10 shows a method of modifying a template double-stranded polynucleotide (a) by contacting the strand with a MuA transposase (b) and a population of Y-shaped MuA substrates (c). The Y-shaped MuA substrate contains a single nucleoside that is not present in the template polynucleotide labelled as a triangle. The MuA transposase fragments the template double-stranded polynucleotide and inserts the Y-shaped MuA substrate at each side of the point of fragmentation (Step 1). The Uracil-Specific Excision Reagent (USER™) then generates a single nucleotide gap at the location of the single nucleoside that is not present in the template polynucleotide (triangle) which allows the removal of the DNA fragment which contains the single nucleoside that is not present in the template polynucleotide (d) (Step 2). The single stranded DNA gap which is left in the fragmented double-stranded construct is then repaired using a DNA polymerase (e), which fills in the gap with the appropriate complementary nucleotides, and a DNA ligase (f), which ligates the newly synthesised strand to the double stranded construct comprising a single-stranded gap (Step 3).
Figure 11:
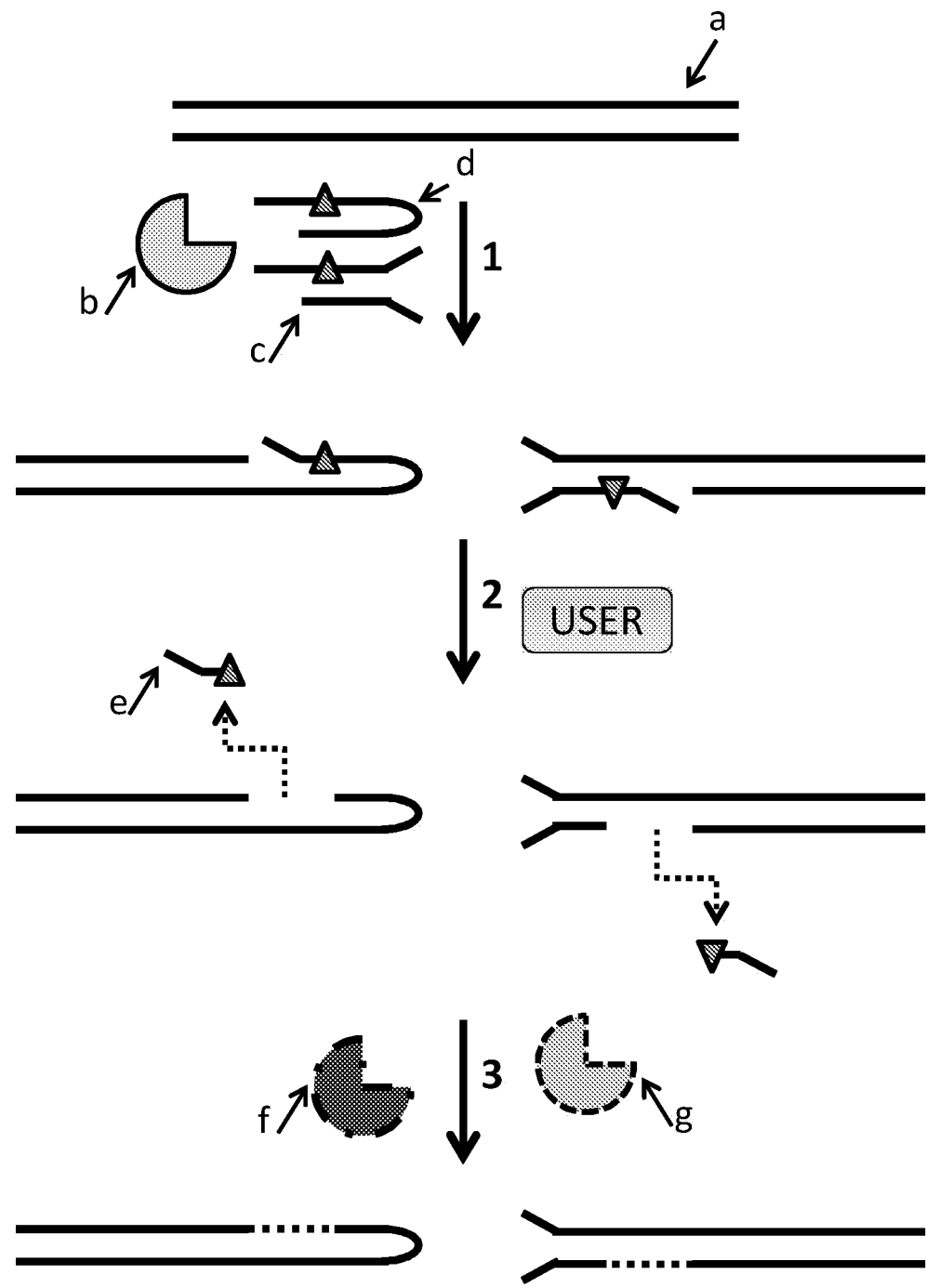
FIG. 11 shows a method of modifying a template double-stranded polynucleotide (a) by contacting the strand with a MuA transposase (b) and a population of double-stranded hairpin MuA substrates (d) and Y-shaped MuA substrates (c). Both types of MuA substrate contain a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of any single nucleosides that are not present in the template polynucleotide (triangle) which allows the removal of the DNA fragments which contain the single nucleoside that is not present in the template polynucleotide (e) (Step 2). The single stranded DNA gap which is left in the fragmented double-stranded construct is then repaired using a DNA polymerase (f), which fills in the gap with the appropriate complementary nucleotides, and a DNA ligase (g), which ligates the newly synthesised strand to the double stranded construct comprising a single-stranded gap (Step 3).

Alternatively, each substrate is preferably a Y substrate with an overhang at one end and a region that is not complementary at the other end. The non-complementary region gives the substrate its Y shape since the two strands typically do not hybridise to each other unlike the double stranded portion. The use of Y substrates results in the production of modified double stranded polynucleotides in step (c) which have the non-complementary region at one or both ends. An example of this is shown in FIGS. 3 and 10. The non-complementary region may comprise a leader sequence in one strand and a coupling means in other strand as discussed above.

Figure 5:
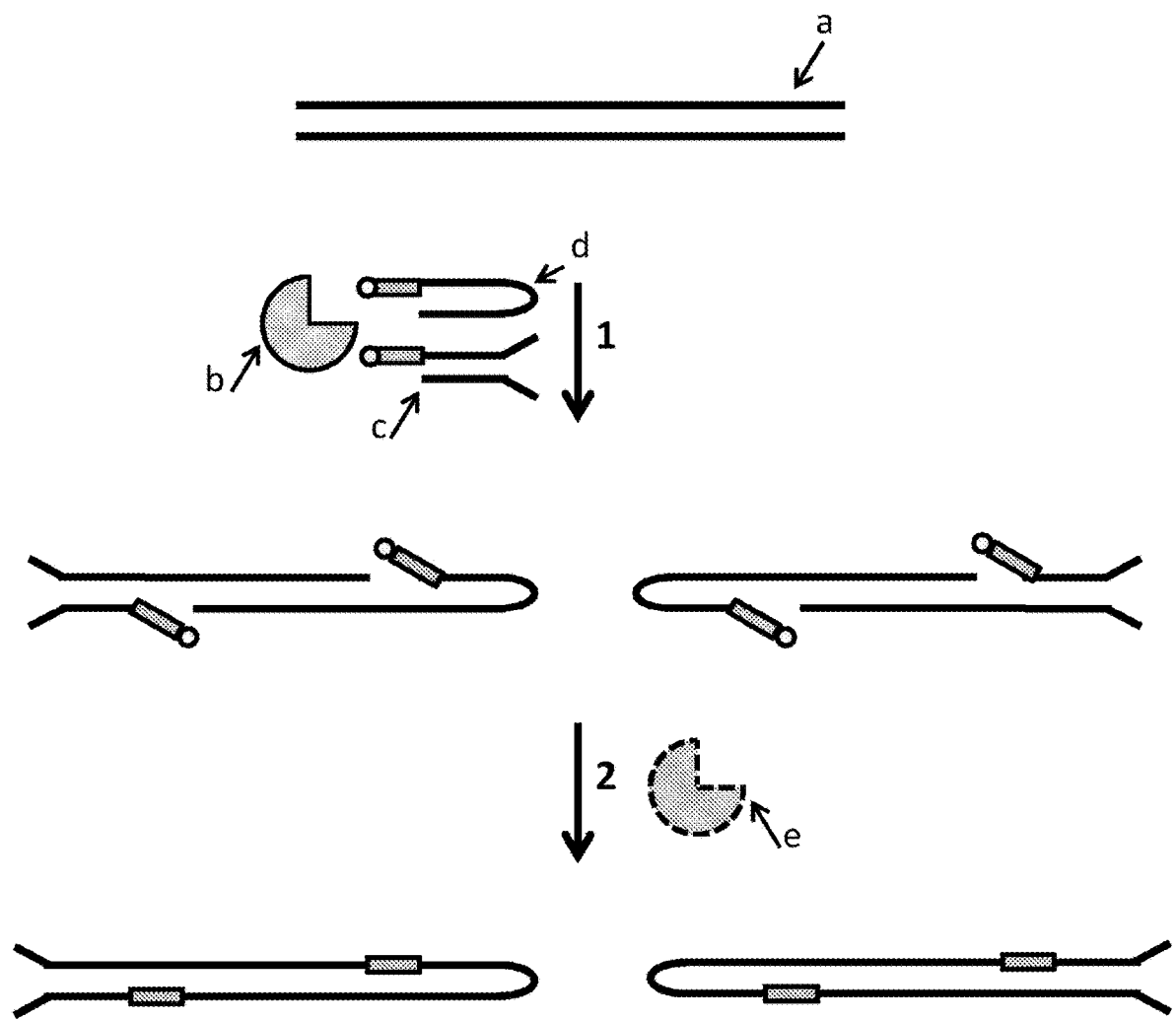
FIG. 5 shows a method of modifying a template double-stranded polynucleotide (a) by contacting the strand with a MuA transposase (b) and a population of double-stranded hairpin MuA substrates (d) and Y-shaped MuA substrates (c). Both types of MuA substrate each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nicks which are left in the fragmented double-stranded construct are then repaired using a DNA ligase (e), which ligates the strand containing the universal nucleotides to the double stranded construct (Step 2).
Figure 12:
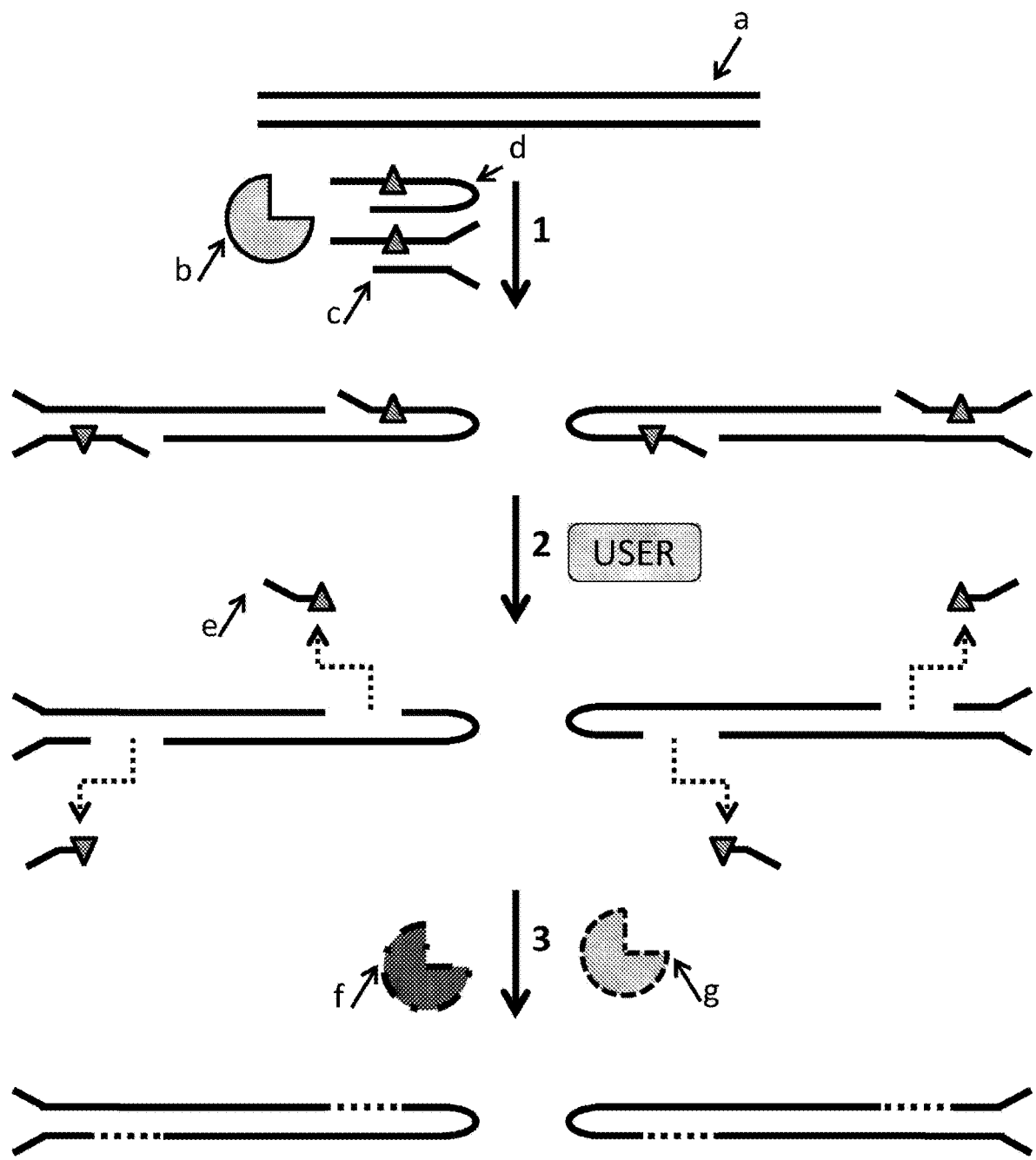
FIG. 12 shows a method of modifying a template double-stranded polynucleotide (a) by contacting the strand with a MuA transposase (b) and a population of double-stranded hairpin MuA substrates (d) and Y-shaped MuA substrates (c). Both types of MuA substrate contain a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of any single nucleosides that are not present in the template polynucleotide (triangle) which allows the removal of the DNA fragments which contain the single nucleoside that is not present in the template polynucleotide (e) (Step 2). The single stranded DNA gaps which are left in the fragmented double-stranded construct are then repaired using a DNA polymerase (f), which fills in the gaps with the appropriate complementary nucleotides, and a DNA ligase (g), which ligates the newly synthesised strand to the double stranded construct comprising a single-stranded gap (Step 3).

Alternatively, in a preferred embodiment, a proportion of the substrates in the population comprise an overhang at one end and a hairpin loop at the other end and a proportion of the substrates in the population are Y substrates with an overhang at one end and a region that is not complementary at the other end. This results in at least some of the modified double stranded polynucleotides produced in step (c) having the hairpin loop at one end and the non-complementary region at the other end. An example of this is shown in FIGS. 5 and 12.

Figure 6:
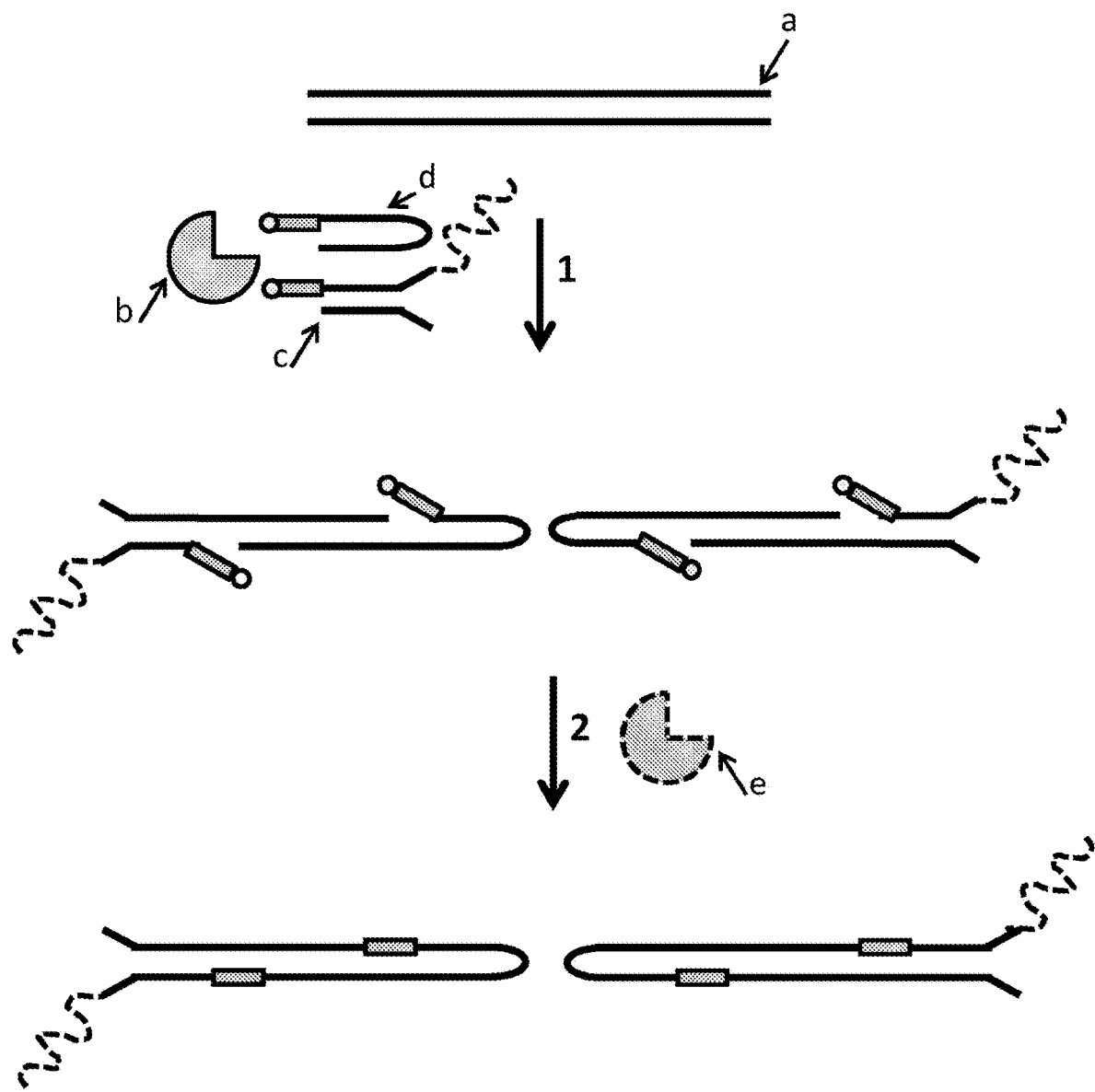
FIG. 6 shows a method of modifying a template double-stranded polynucleotide (a) by contacting the strand with a MuA transposase (b) and a population of double-stranded hairpin MuA substrates (d) and Y-shaped MuA substrates (c). The Y-shaped MuA substrate has an additional polyT leader sequence (show as a dashed wiggly line). Both types of MuA substrate each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nicks which are left in the fragmented double-stranded construct are then repaired using a DNA ligase (e), which ligates the strand containing the universal nucleotides to the double stranded construct (Step 2).
Figure 7:
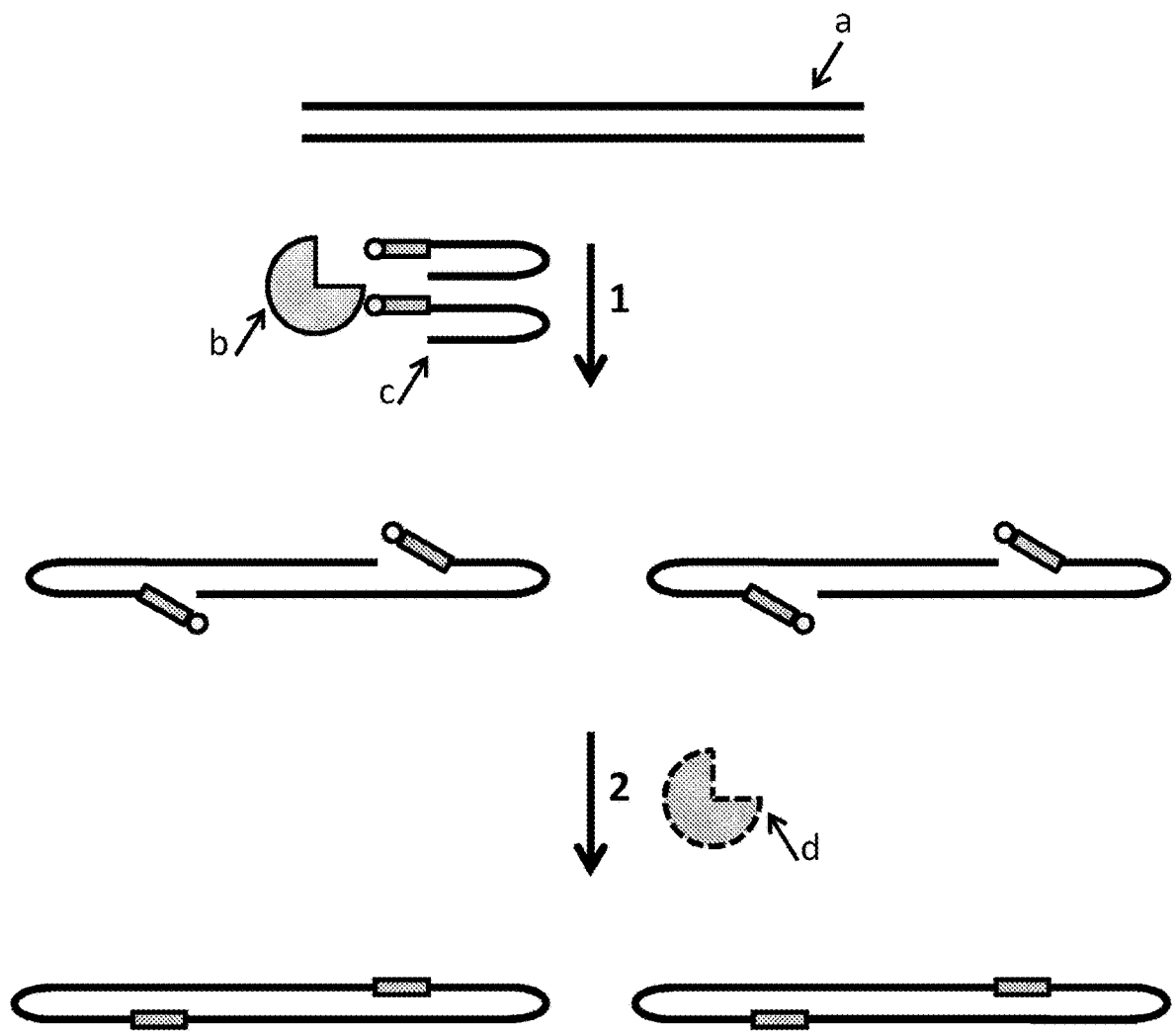
FIG. 7 shows a method of modifying a template double-stranded polynucleotide (a) by contacting the strand with a MuA transposase (b) and a population of double-stranded hairpin MuA substrates (c). The hairpin MuA substrates each contain a 5'phosphate (labelled as a circle) and five universal nucleotides (labelled as a rectangle). The MuA transposase fragments the template double-stranded polynucleotide and inserts the MuA substrates at each side of the point of fragmentation (Step 1). The nicks which are left in the fragmented double-stranded construct are then repaired using a DNA ligase (d), which ligates the strand containing the universal nucleotides to the double stranded construct (Step 2).
Figure 8:
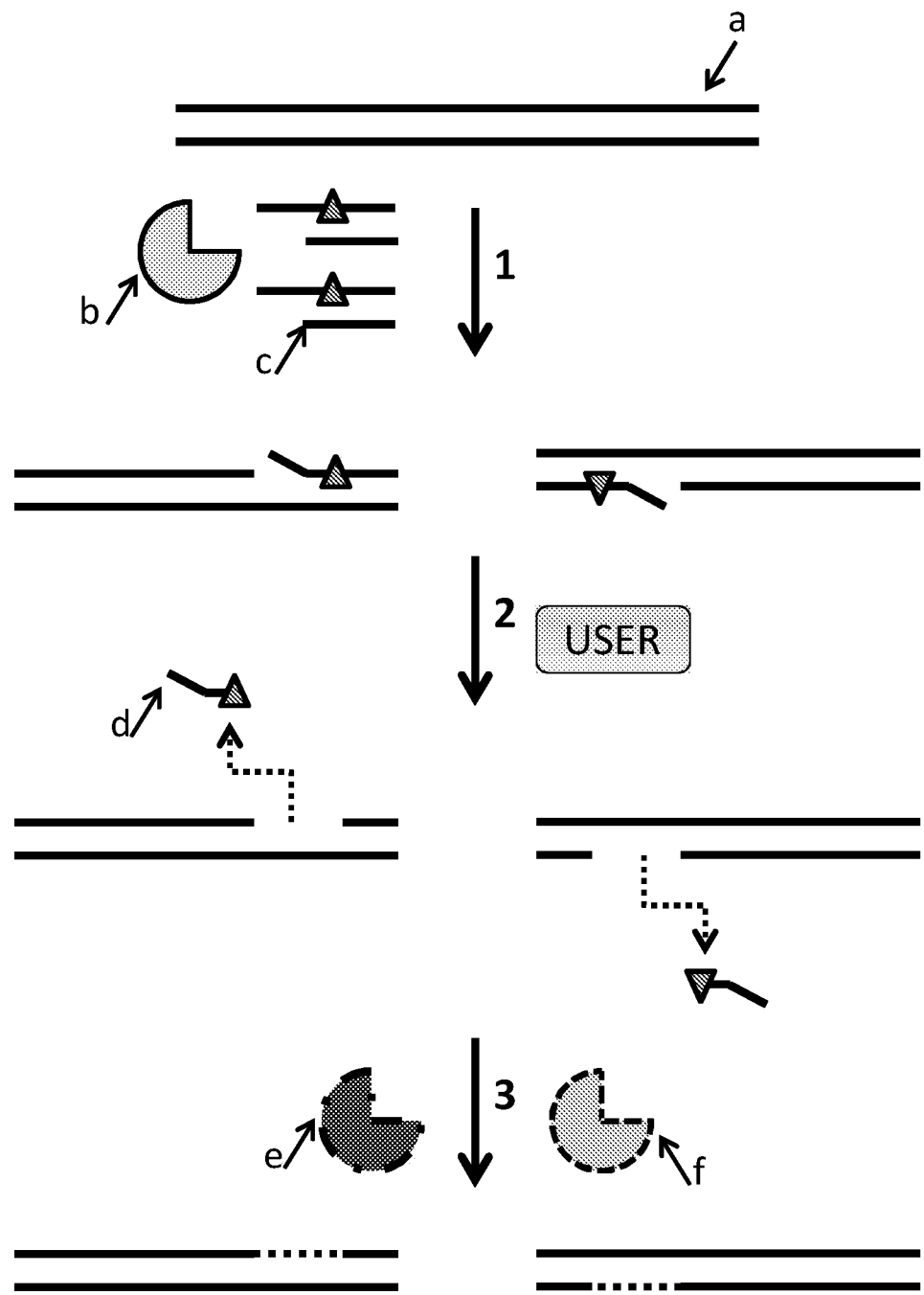
FIG. 8 shows a method of modifying a template double-stranded polynucleotide (a) by contacting the strand with a MuA transposase (b) and a population of double-stranded MuA substrates (c). The double stranded MuA substrate contains a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of the single nucleoside that is not present in the template polynucleotide (triangle) which allows the removal of the DNA fragment which contains the single nucleoside that is not present in the template polynucleotide (d) (Step 2). The single stranded DNA gap which is left in the fragmented double-stranded construct is then repaired using a DNA polymerase (e), which fills in the gap with the appropriate complementary nucleotides, and a DNA ligase (f), which ligates the newly synthesised strand to the double stranded construct comprising a single-stranded gap (Step 3).
Figure 9:
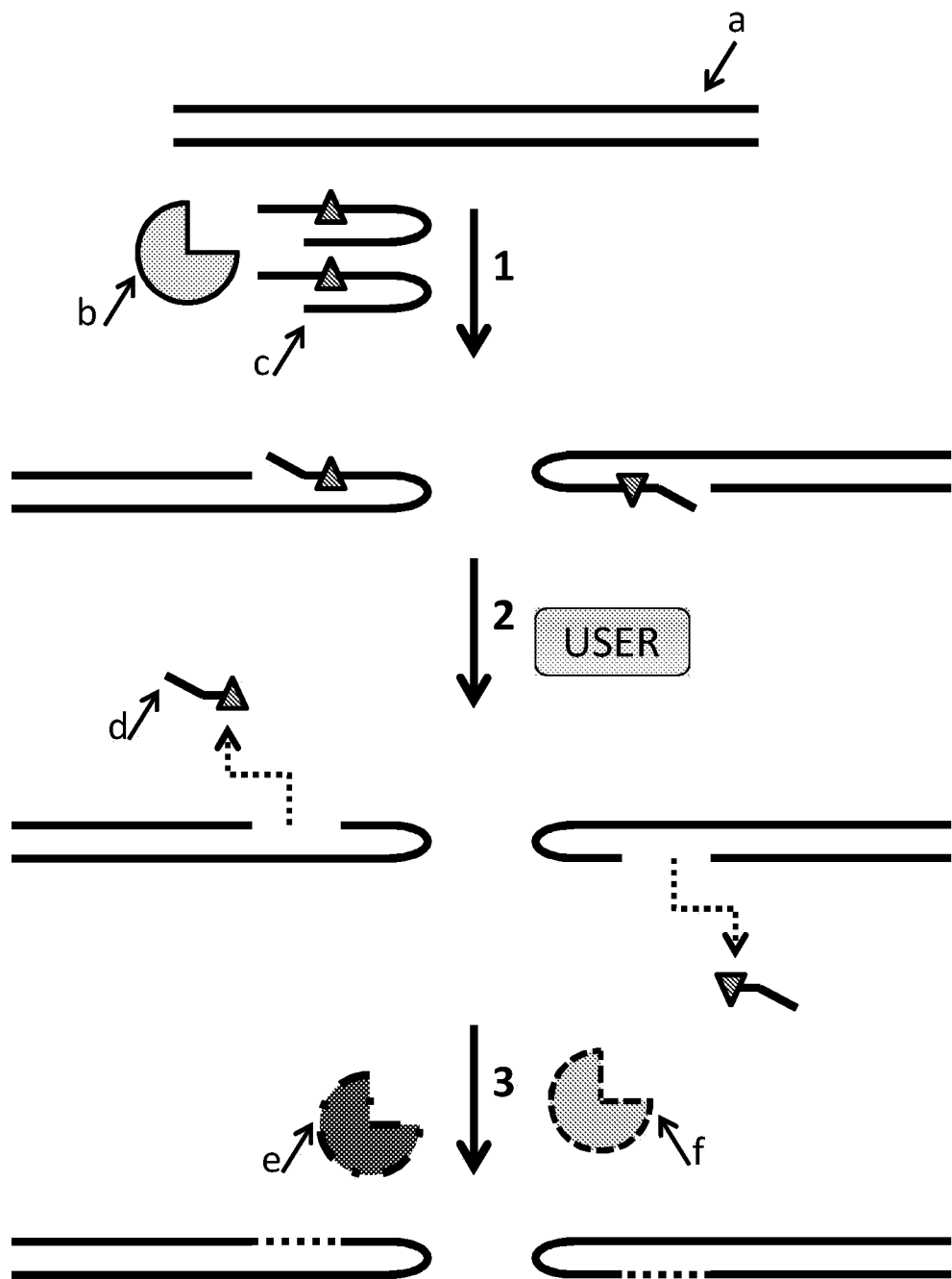
FIG. 9 shows a method of modifying a template double-stranded polynucleotide (a) by contacting the strand with a MuA transposase (b) and a population of double-stranded hairpin MuA substrates (c). The hairpin MuA substrate contains a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of the single nucleoside that is not present in the template polynucleotide (triangle) which allows the removal of the DNA fragment which contains the single nucleoside that is not present in the template polynucleotide (d) (Step 2). The single stranded DNA gap which is left in the fragmented double-stranded construct is then repaired using a DNA polymerase (e), which fills in the gap with the appropriate complementary nucleotides, and a DNA ligase (f), which ligates the newly synthesised strand to the double stranded construct comprising a single-stranded gap (Step 3).
Figure 13:
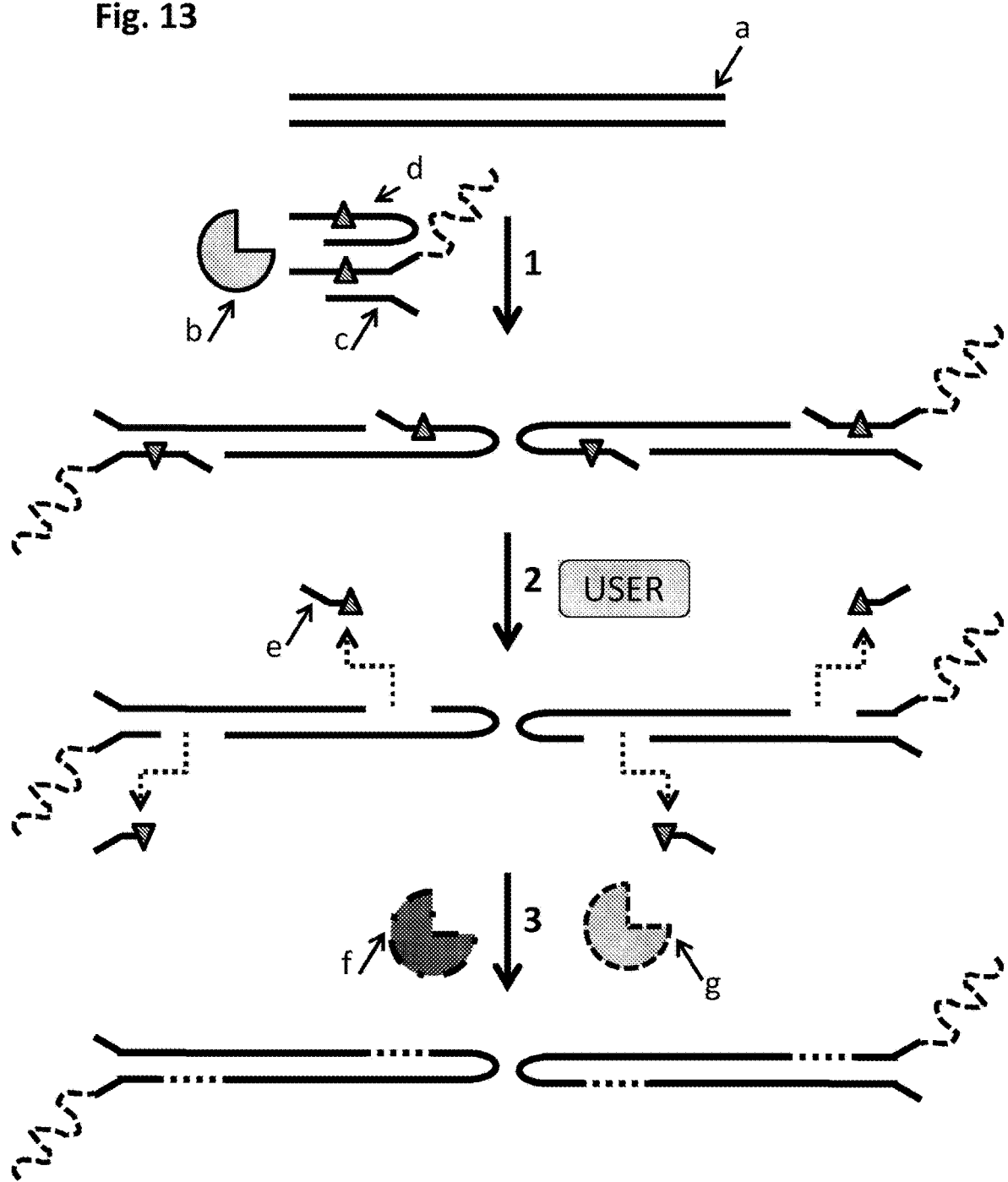
FIG. 13 shows a method of modifying a template double-stranded polynucleotide (a) by contacting the strand with a MuA transposase (b) and a population of double-stranded hairpin MuA substrates (d) and Y-shaped MuA substrates (c). The Y-shaped MuA substrate has an additional polyT leader sequence (show as a dashed wiggly line). Both types of MuA substrate contain a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of any single nucleosides that are not present in the template polynucleotide (triangle) which allows the removal of the DNA fragments which contain the single nucleoside that is not present in the template polynucleotide (e) (Step 2). The single stranded DNA gaps which are left in the fragmented double-stranded construct are then repaired using a DNA polymerase (f), which fills in the gaps with the appropriate complementary nucleotides, and a DNA ligase (g), which ligates the newly synthesised strand to the double stranded construct comprising a single-stranded gap (Step 3).
Figure 14:
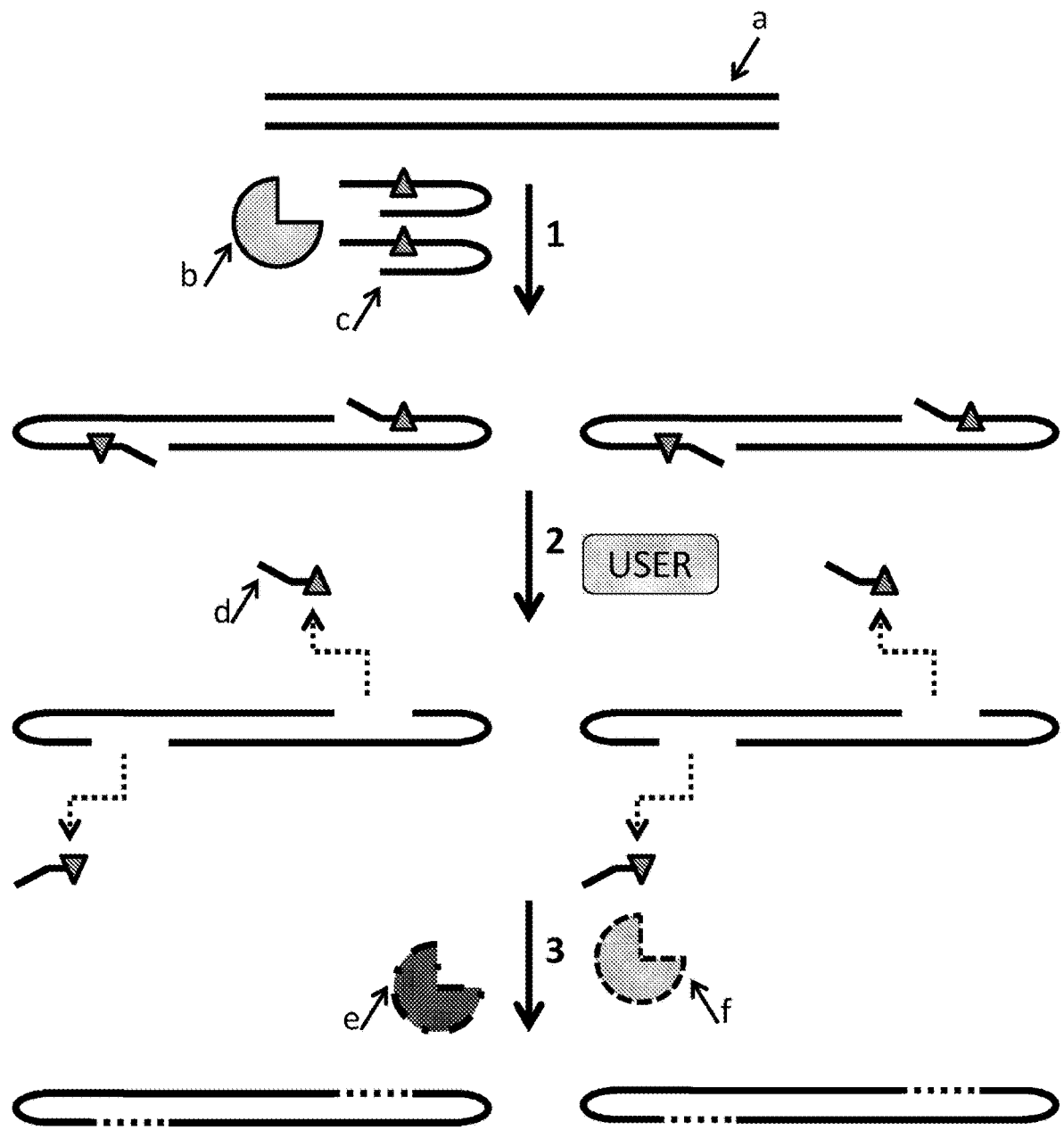
FIG. 14 shows a method of modifying a template double-stranded polynucleotide (a) by contacting the strand with a MuA transposase (b) and a population of double-stranded hairpin MuA substrates (c). The hairpin MuA substrate contains a single nucleoside that is not present in the template polynucleotide labelled as a triangle. The MuA transposase fragments the template double-stranded polynucleotide and inserts the MuA substrates at each side of the point of fragmentation (Step 1). The Uracil-Specific Excision Reagent (USER™) then generates a single nucleotide gap at the location of any single nucleosides that are not present in the template polynucleotide (triangle) which allows the removal of the DNA fragments which contain the single nucleoside that is not present in the template polynucleotide (d) (Step 2). The single stranded DNA gaps which are left in the fragmented double-stranded construct are then repaired using a DNA polymerase (f), which fills in the gaps with the appropriate complementary nucleotides, and a DNA ligase (g), which ligates the newly synthesised strand to the double stranded construct comprising a single-stranded gap (Step 3).

Alternatively, in a preferred embodiment, a proportion of the substrates in the population comprise an overhang at one end and a hairpin loop at the other end and a proportion of the substrates in the population comprise an overhang at one end and a leader sequence or coupling means at the other end. This results in at least some of the modified double stranded polynucleotides produced in step (c) having the hairpin loop at one end and the leader sequence or coupling means at the other end. An example of this is shown in FIGS. 6 and 13 (where the leader sequence is shown as a dashed wiggly line).

In the most preferred embodiment, a proportion of the substrates in the population comprise an overhang at one end and a hairpin loop at the other end and a proportion of the substrates in the population comprise an overhang at one end and a leader sequence and a coupling means at the other end. This results in at least some of the modified double stranded polynucleotides produced in step (c) having the hairpin loop at one end and the leader sequence and coupling means at the other end. These modified double stranded polynucleotides are particularly useful for characterisation because they can be coupled to the membrane in which the nanopore is located, have a leader sequence which facilitates the threading of the polynucleotides into the nanopore and both strands can be characterised around the hairpin loop.

In all of the embodiments above, the proportion of one type of substrate may be any proportion, such as at least about 5%, at least about 10%, at least about 20%, at least about 30%, at least about 40%, at least about 50%, at least about 60%, at least about 70%, at least about 80%, at least about 90% or at least about 95%. The remaining proportion of substrates in the population is typically the other type of substrate. For instance, the population may comprise about 40% of the substrates comprising a hairpin loop and about 60% of the Y substrates. The proportion of both types of substrate is preferably about 50%.

Each substrate may comprise a selectable binding moiety. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridize) to a surface coated with homologous sequences. Alternatively, selectable nucleic acid sequences specifically bind to a surface coated with nucleic acid binding proteins.

Ligating the Overhangs

In those embodiments in which the MuA substrates comprise overhangs of universal nucleotides, the method comprises ligating the overhangs to the fragments in the constructs. This may be done using any method of ligating nucleotides known in the art. For instance, it may be done using a ligase, such as a DNA ligase. Alternatively, if the overhangs comprise a reactive group, the reactive group may be used to ligate the overhangs to the fragments in the constructs. For instance, a nucleotide comprising a complementary reactive group may be attached to the fragments and the two reactive groups may be reacted together to ligate the overhangs to the fragments. Click chemistry may be used as discussed above.

Selective Removal

Methods are known in the art for selectively removing the nucleotide(s) which comprise(s) a nucleoside that is not present in the template polynucleotide from the ligated constructs. Nucleotides are selectively removed if they are removed (or excised) from the ligated constructs, but the other nucleotides in the ligated constructs (i.e. those comprising different nucleosides) are not removed (or excised).

Nucleotides comprising deoxyuridine (dU) may be selectively removed using Uracil-Specific Excision Reagent (USER®), which is a mixture of Uracil DNA glycosylase (UDG) and the DNA glycosylase-lyase Endonuclease VIII.

Selective removal of the nucleotide(s) which comprise(s) a nucleoside that is not present in the template polynucleotide from the ligated constructs removes the overhang(s) from the constructs as shown in the Figures. Removal of the overhangs results in a plurality of double stranded constructs comprising single stranded gaps as shown in the FIGS. 8 to 14.

Repairing the Gaps

Methods are known in the art for repairing the single stranded gaps in the double stranded constructs. For instance, the gaps can be repaired using a polymerase and a ligase, such as DNA polymerase and a DNA ligase. Alternatively, the gaps can be repaired using random oligonucleotides of sufficient length to bring the gaps and a ligase.

Separating Hairpin Loops

As discussed above, the method of the invention may produce a plurality of modified double stranded polynucleotides whose strands are linked by a hairpin loop at one end. In such embodiments, the method preferably further comprises (d) separating the two strands of at least one modified double stranded polynucleotide to produce at least one single stranded polynucleotide comprising one strand of the modified double stranded polynucleotide linked to the other strand of the modified double stranded polynucleotide. The two strands may be separated in any way. The two strands are preferably separated by contacting the modified double stranded polynucleotide with a polynucleotide binding protein as discussed below.

Products of the Invention

The invention also provides a population of double stranded MuA substrates for modifying a template polynucleotide, wherein each substrate comprises at least one overhang of universal nucleotides. The invention also provides a population of double stranded MuA substrates for modifying a template polynucleotide, wherein each substrate comprises (i) at least one overhang and (ii) at least one nucleotide in the same strand as the at least one overhang which comprises a nucleoside that is not present in the template polynucleotide. The substrates may be any of those described above. The substrates preferably comprise a double stranded portion as defined above. The double stranded portion preferably comprises SEQ ID NOS: 24-25 as discussed above. The double stranded portion more preferably comprises SEQ ID NO: 24 and SEQ ID NO: 26 as discussed above. Preferred populations of the invention are those in which:

each substrate comprises an overhang at one end and a hairpin loop at the other end;

each substrate is preferably a Y substrate with an overhang at one end and a region that is not complementary at the other end;

a proportion of the substrates in the population comprise an overhang at one end and a hairpin loop at the other end and a proportion of the substrates in the population are Y substrates with an overhang at one end and a region that is not complementary at the other end;

a proportion of the substrates in the population comprise an overhang at one end and a hairpin loop at the other end and a proportion of the substrates in the population comprise an overhang at one end and a leader sequence or coupling means at the other end; and a proportion of the substrates in the population comprise an overhang at one end and a hairpin loop at the other end and a proportion of the substrates in the population comprise an overhang at one end and a leader sequence and a coupling means at the other end.

The proportion values given above in connection the method of the invention are equally applicable to the populations of the invention.

The invention also provides a plurality of polynucleotides modified using the method of the invention. The plurality of polynucleotides may be in any of the forms discussed above. Preferred pluralities are those which comprise:

double stranded polynucleotides which are linked by a hairpin loop at one or both ends;

double stranded polynucleotides which have a non-complementary region at one or both ends;

double stranded polynucleotides which have a hairpin loop at one end and a non-complementary region at the other end.

double stranded polynucleotides which have a hairpin loop at one end and a leader sequence or coupling means at the other end;

double stranded polynucleotides which have a hairpin loop at one end and a leader sequence and coupling means at the other end.

The population or plurality may be isolated, substantially isolated, purified or substantially purified. A population or plurality is isolated or purified if it is completely free of any other components, such as the template polynucleotide, lipids or pores. A population or plurality is substantially isolated if it is mixed with carriers or diluents which will not interfere with its intended use. For instance, a population or plurality is substantially isolated or substantially purified if it is present in a form that comprises less than 10%, less than 5%, less than 2% or less than 1% of other components, such as lipids or pores.

Characterisation Method of the Invention

The invention also provides a method of characterising at least one polynucleotide modified using a method of the invention. The method comprises (a) contacting the modified polynucleotide with a transmembrane pore such that at least one strand of the polynucleotide moves through the pore. The method also comprises (b) taking one or more measurements as the at least one strand moves with respect to the pore wherein the measurements are indicative of one or more characteristics of the at least one strand and thereby characterising the modified polynucleotide. If the modified polynucleotide comprises a hairpin loop, the method preferably comprises (a) contacting the modified polynucleotide with a transmembrane pore such that both strands of the polynucleotide move through the pore and (b) taking one or more measurements as both strands move with respect to the pore wherein the measurements are indicative of one or more characteristics of both strands and thereby characterising the modified polynucleotide.

This method is preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the polynucleotide moves with respect to the pore is used to determine the sequence of the modified polynucleotide. This is strand sequencing.

The invention also provides a method of characterising a template polynucleotide. In step (a), the template polynucleotide is modified using the method of the invention. The method then comprises (b) contacting each modified polynucleotide with a transmembrane pore such that at least one strand of each polynucleotide moves through the pore. The method also comprises (c) taking one or more measurements as the at least one strand of each polynucleotide moves with respect to the pore wherein the measurements are indicative of one or more characteristics of the at least one strand of each polynucleotide and thereby characterising the template polynucleotide. If the modified polynucleotides comprise a hairpin loop, the method preferably comprises (b) contacting each modified polynucleotide with a transmembrane pore such that both strands of each polynucleotide move through the pore and (c) taking one or more measurements as both strands of each polynucleotide move with respect to the pore wherein the measurements are indicative of one or more characteristics of both strands of each polynucleotide and thereby characterising the template polynucleotide.

Steps (b) and (c) are preferably carried out with a potential applied across the pore as described above. In some instances, the current passing through the pore as the at least one strand of each polynucleotide moves with respect to the pore is used to determine the sequence of each modified polynucleotide. This is strand sequencing. The sequence of the template polynucleotide may then be reconstructed. In particular, the method preferably further comprises d) aligning the sequences of the plurality of modified polynucleotides to produce the sequence of the template polynucleotide and thereby sequencing the template polynucleotide. Suitable methods are disclosed in Baker, M., Nature Methods, 2012, 9, 4, 333-337 and Flicek, P. and Birney E., Nature Methods Supplement, 2009, 6, 11, S6-S12.

The whole or only part of the modified or template polynucleotide may be characterised, for instance sequenced, using this method. The length of the template polynucleotide is discussed above.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The modified polynucleotide(s) may be coupled to the membrane. This may be done using any known method. If the membrane is an amphiphilic layer, such as a lipid bilayer (as discussed in detail above), the modified polynucleotide(s) are preferably coupled to the membrane via a polypeptide present in the membrane or a hydrophobic anchor present in the membrane. The hydrophobic anchor is preferably a lipid, fatty acid, sterol, carbon nanotube or amino acid.

The modified polynucleotide(s) may be coupled directly to the membrane. The modified polynucleotide(s) are preferably coupled to the membrane via a linker. Preferred linkers include, but are not limited to, polymers, such as polynucleotides, polyethylene glycols (PEGs) and polypeptides. If a modified polynucleotide is coupled directly to the membrane, then some data will be lost as the characterising run cannot continue to the end of the polynucleotide due to the distance between the membrane and the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the pore. If the coupling is transient, then when the coupled end randomly becomes free of the bilayer, then the polynucleotide can be processed to completion. Chemical groups that form stable or transient links with the membrane are discussed in more detail below. The modified polynucleotide(s) may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the modified polynucleotide(s) are coupled to an amphiphilic layer. Coupling of polynucleotides to synthetic lipid bilayers has been carried out previously with various different tethering strategies. These are summarised in Table 1 below.

TABLE 1

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behaviour of giant vesicles with anchored DNA molecules." *Biophys J* 92(12): 4356-68 |
| Cholesterol | Transient | Pfeiffer, I. and F. Hook (2004). "Bivalent cholesterol- based coupling of oligonucleotides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of the DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an reverse primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOS: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropath |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the construct. The variant preferably comprises one or more reactive cysteine residues that facilitate attachment to the construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application No. PCT/GB09/001690 (published as WO 2010/004273), PCT/GB09/001679 (published as WO 2010/004265), PCT/GB10/000133 (published as WO 2010/086603) or PCT/GB10/000132 (published as WO 2010/086602).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The pore may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the modified polynucleotide(s) or template polynucleotide. The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the/each modified polynucleotide with a transmembrane pore such that at least one strand of the/each polynucleotide moves through the pore; and (b) measuring the current passing through the pore as at least one strand of the/each polynucleotide moves with respect to the pore wherein the current is indicative of one or more characteristics of the at least one strand of the/each polynucleotide and thereby characterising the modified/template polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the/each polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method preferably further comprises contacting the/ each modified polynucleotide with a polynucleotide binding protein such that the protein controls the movement of the at least one strand of the/each polynucleotide through the pore. If the modified polynucleotide(s) comprise a hairpin loop, the method preferably further comprises contacting the/each modified polynucleotide with a polynucleotide binding protein such that the protein controls the movement of both strands of the/each polynucleotide through the pore.

More preferably, the method comprises (a) contacting the/each modified polynucleotide with a transmembrane pore and a polynucleotide binding protein such that at least one strand of the/each polynucleotide moves through the pore and the protein controls the movement of the at least one strand of the/each polynucleotide through the pore and (b) measuring the current passing through the pore as the at least one strand of the/each polynucleotide moves with respect to the pore wherein the current is indicative of one or more characteristics of the at least one strand of the/each polynucleotide and thereby characterising the modified/ template polynucleotide. If the modified polynucleotide(s) comprise a hairpin loop, the method more preferable comprises (a) contacting the/each modified polynucleotide with a transmembrane pore and a polynucleotide binding protein such that both strands of the/each polynucleotide moves through the pore and the protein controls the movement of both strands of the/each polynucleotide through the pore and (b) measuring the current passing through the pore as both strands of the/each polynucleotide moves with respect to the pore wherein the current is indicative of one or more characteristics of both strands of the/each polynucleotide and thereby characterising the modified/template polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 20), TraI Eco (SEQ ID NO: 21), XPD Mbu (SEQ ID NO: 22) or a variant thereof.

A variant of SEQ ID NOS: 9, 11, 13, 15, 17, 18, 19, 20, 21, 22 or 23 is an enzyme that has an amino acid sequence which varies from that of SEQ ID NOS: 9, 11, 13, 15, 17, 18, 19, 20, 21, 22 or 23 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature.

Over the entire length of the amino acid sequence of SEQ ID NOS: 9, 11, 13, 15, 17, 18, 19, 20, 21, 22 or 23, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOS: 9, 11, 13, 15, 17, 18, 19, 20, 21, 22 or 23 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and SEQ ID NO: 4 above. The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

The method of characterising a modified or a template polynucleotide preferably involves contacting the polynucleotide with a pore and a polynucleotide binding protein derived from a helicase. Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the bilayer. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the bilayer.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

The method is typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Kits

The present invention also provides a kit for modifying a template polynucleotide. The kit comprises (a) a population of MuA substrates of the invention and (b) a MuA transposase. Any of the embodiments discussed above with reference to the methods and products of the invention equally apply to the kits.

The kit may further comprise the components of a membrane, such as the components of an amphiphilic layer or a lipid bilayer. The kit may further comprise the components of a transmembrane pore. The kit may further comprise a polynucleotide binding protein. Suitable membranes, pores and polynucleotide binding proteins are discussed above.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention.

Example 1

This example shows that the MuA transposase was able to insert MuA substrates which contained at least one nucleoside which was not present in the template polynucleotide into a template double-stranded polynucleotide. In this example the one nucleotide which was not present in the template was a dUMP.

Materials and Methods 1.1 Anneal of DNA Strands to Form the MuA Substrates

Figure 15:
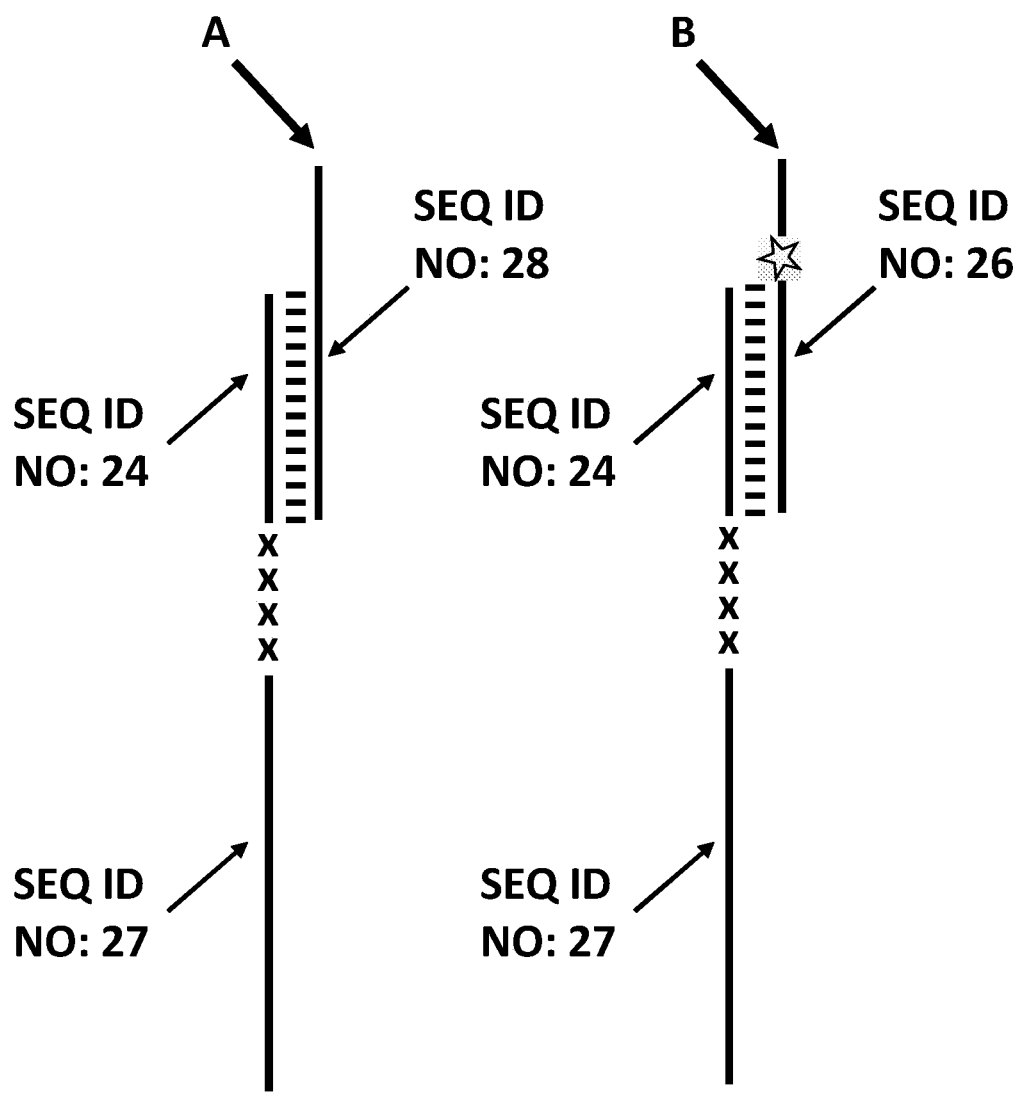
FIG. 15 shows the DNA substrate designs for the two MuA substrates used in Example 1 (MuA substrate 1 is labelled A and MuA substrate 2 is labelled B). The dUMP in SEQ ID NO: 26 is highlighted as a star and the C3 spacers are shown as x's.

MuA substrate 1 and 2 were prepared as shown in Table 4 below. The construct A and B sample mixtures were then heated to 95° C. for 2 minutes and then cooled to 16° C. at a rate of 2° C. per minute. This allowed SEQ ID NO: 27 which was attached to SEQ ID NO: 24 by four C3 spacer units to anneal to either SEQ ID NO: 28 (MuA substrate 1) or SEQ ID NO: 26 (MuA substrate 2). The DNA substrate designs of the two MuA substrates formed are shown in FIG. 15.

TABLE 4

| Reagent | MuA substrate 1 | MuA substrate 2 | Final Concentrations |
|---|---|---|---|
| Water | 12 uL | 12 uL | |
| 0.25M NaCl, 50 mM Tris pH 7.5 | 4 uL | 4 uL | 50 mM NaCl, 10 mM Tris |
| SEQ ID NO: 27 attached to SEQ ID NO: 24 by four C3 spacer units (100 uM) | 2 uL | 2 uL | 10 uM |
| SEQ ID NO: 28 (100 uM) | 2 uL | | 10 uM |
| SEQ ID NO: 26 (100 uM) | | 2 uL | 10 uM |
| Total | 20 uL | 20 uL | |

1.2 Fragmentation of the DNA Template Using the MuA Transposase

Figure 16:
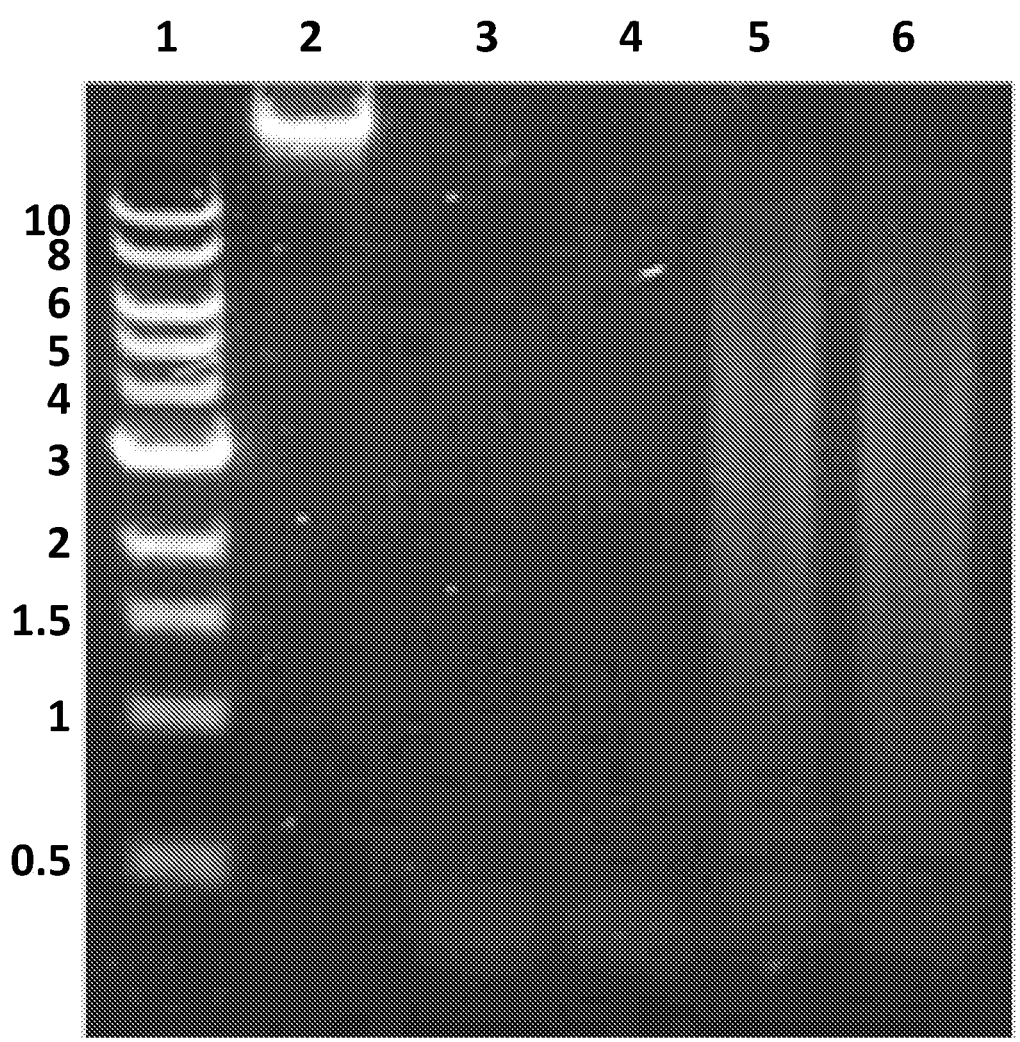
FIG. 16 shows the lanes in the gel related to the following samples—lane 1=appropriate DNA ladder (Units of the DNA markers is kb), lane 2 corresponded to sample 1 (a control showing the band produced by unmodified SEQ ID NO: 29), lane 3 corresponded to sample 2 (the wild-type MuA substrate (MuA substrate 1, SEQ ID NO: 27 attached to SEQ ID NO: 24 by four C3 spacer units, hybridised to SEQ ID NO: 28) which did not contain at least one nucleoside which was not present in the template polynucleotide (SEQ ID NO: 29)), lane 4 corresponded to sample 3 (the MuA substrate which contained a dUMP (MuA substrate 2, SEQ ID NO: 27 attached to SEQ ID NO: 24 by four C3 spacer units, hybridised to SEQ ID NO: 26) which was not present in the template polynucleotide (SEQ ID NO: 29)), lane 5 corresponded to sample 4 (the broad band on the gel indicated that the MuA transposase was able to insert the wild-type MuA substrate (SEQ ID NO: 27 attached to SEQ ID NO: 24 by four C3 spacer units, hybridised to SEQ ID NO: 28) into the template polynucleotide (SEQ ID NO: 29)), lane 6 corresponded to sample 5 (the broad band on the gel indicated that the MuA transposase was able to insert the MuA substrate which contained a dUMP (SEQ ID NO: 27 attached to SEQ ID NO: 24 by four C3 spacer units, hybridised to SEQ ID NO: 26) into the template polynucleotide (SEQ ID NO: 29)). Lanes 3 and 4 produced a faint band at the bottom of the gel as they were run as additional controls.

Samples 1-5 were prepared as shown in Table 5 below. The samples were then incubated at 30° C. for 1 hour and heat inactivated at 75° C. for 10 minutes. An aliquot (1 μL) of each of samples 1-5 was run on a 12000 Agilent chip and the remainder on a 0.8% TAE agarose gel (60 minutes at 100 V, see FIG. 16). The lanes in the gel related to the following samples—lane 1=appropriate DNA ladder, lane 2 corresponded to sample 1 (a control showing the band produced by unmodified SEQ ID NO: 29), lane 3 corresponded to sample 2 (the wild-type MuA substrate (MuA substrate 1, SEQ ID NO: 27 attached to SEQ ID NO: 24 by four C3 spacer units, hybridised to SEQ ID NO: 28) which did not contain at least one nucleoside which was not present in the template polynucleotide (SEQ ID NO: 29)), lane 4 corresponded to sample 3 (the MuA substrate which contained a dUMP (MuA substrate 2, SEQ ID NO: 27 attached to SEQ ID NO: 24 by four C3 spacer units, hybridised to SEQ ID NO: 26) which was not present in the template polynucleotide (SEQ ID NO: 29)), lane 5 corresponded to sample 4 (the broad band on the gel indicated that the MuA transposase was able to insert the wild-type MuA substrate (SEQ ID NO: 27 attached to SEQ ID NO: 24 by four C3 spacer units, hybridised to SEQ ID NO: 28) into the template polynucleotide (SEQ ID NO: 29)), lane 6 corresponded to sample 5 (the broad band on the gel indicated that the MuA transposase was able to insert the MuA substrate which contained a dUMP (SEQ ID NO: 27 attached to SEQ ID NO: 24 by four C3 spacer units, hybridised to SEQ ID NO: 26) into the template polynucleotide (SEQ ID NO: 29)). Lanes 3 and 4 produced a faint band at the bottom of the gel as they were run as additional controls. FIG. 16 shows that MuA transposase was able to insert MuA substrates which contained at least one nucleoside which was not present in the template polynucleotide (MuA substrate 2).

TABLE 5

| Reagent | Sample 1 | Sample 2 | Sample 3 | Sample 4 | Sample 5 | Final Concentrations |
|---|---|---|---|---|---|---|
| Water | 5.5 uL | 6 uL | 6 uL | 2.5 uL | 2.5 uL | |
| Lambda DNA (100 ng/uL) | 2.5 uL | | | 2.5 uL | 2.5 uL | 250 ng |
| MuA substrate 1 (1 uM) | | 2 uL | | 2 uL | | 200 nM |
| MuA substrate 2 (1 uM) | | | 2 uL | | 2 uL | 200 nM |
| 5x Finnzymes reaction buffer | 2 uL | 2 uL | 2 uL | 2 uL | 2 uL | 1x |
| MuA (4 uM, Thermo, catalogue No. F-750C) | | | | 1 uL | 1 uL | 400 nM |
| Total | 10 uL | 10 uL | 10 uL | 10 uL | 10 uL | |

Example 2

Figure 17:
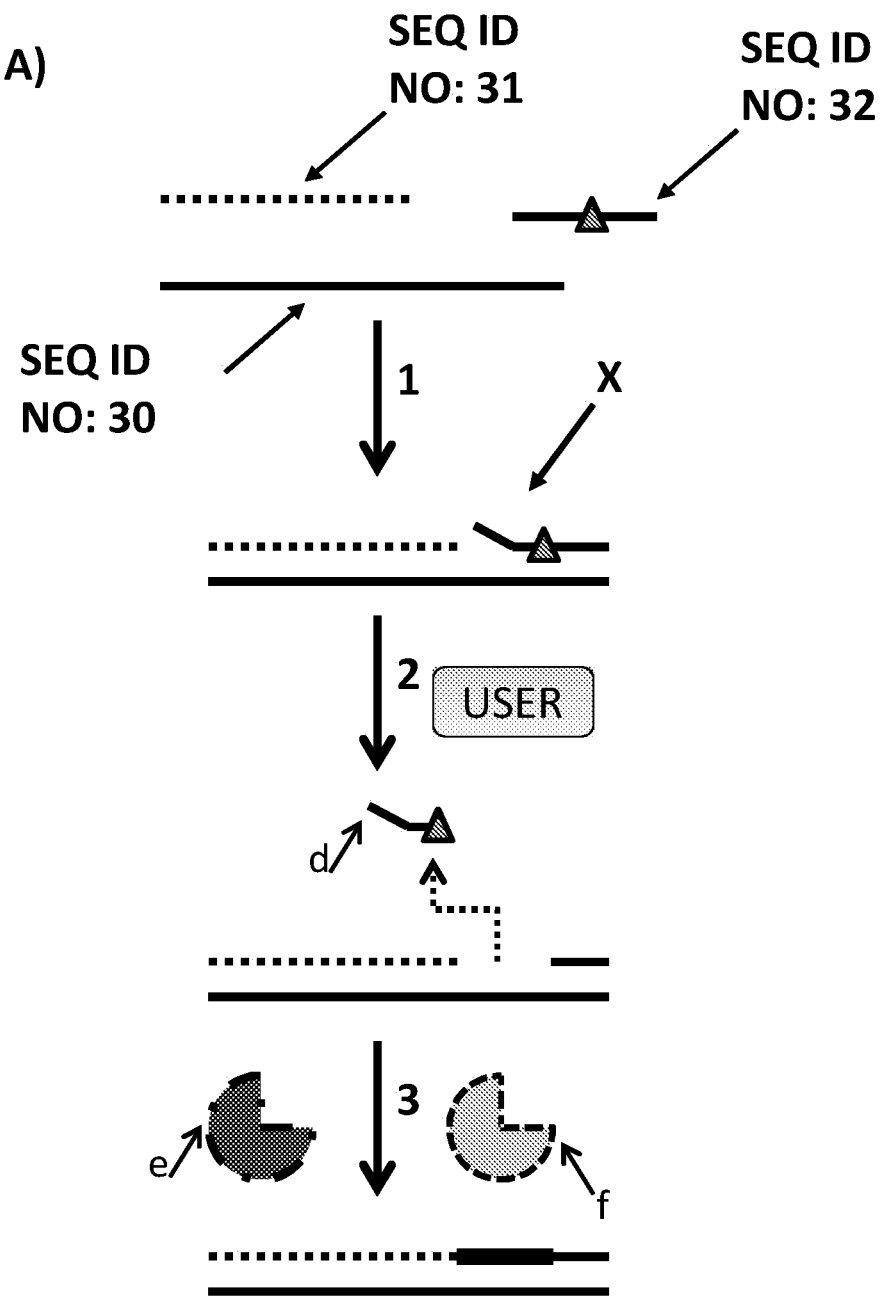
FIG. 17 section A) shows the sample preparation process described in Example 2. In step 1 ssDNA fragments were annealed in order to form a model construct (X). Step 2 shows the removal of the dUMP from construct X (labelled as a triangle) using USER™. Finally, in step 3 the gap in construct x was repaired using a DNA polymerase and ligase, to produce a ds-DNA polynucleotide. Section B) shows the control strand, where SEQ ID NO: 30 annealed to SEQ ID NO: 33 its complementary strand.
Figure 17:
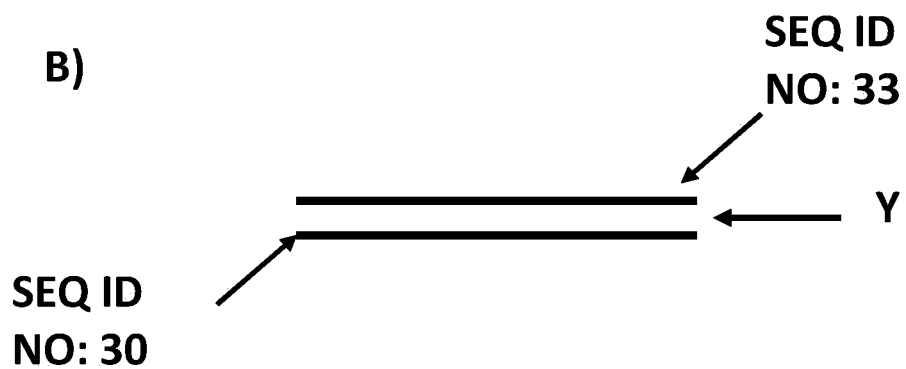

This example describes the sample preparation process described in FIG. 17 section A). In step 1 ssDNA fragments were annealed in order to form a model construct (X). In step 2 the dUMP (labelled as a triangle) was removed using USER™. Finally, in step 3 the gap in construct x was repaired using a DNA polymerase and ligase, to produce a modified ds-DNA polynucleotide. FIG. 17 section B shows construct Y the ds DNA control.

Materials and Methods

2.1 Anneal of DNA Strands to Form Construct X and Y

Constructs X and Y were prepared as shown in Table 6 below. The sample mixtures which contained the DNA to form constructs X and Y were then heated to 95° C. for 2 minutes and then cooled to 16° C. at a rate of 2° C. per minute. This allowed SEQ ID NO: 30 to anneal to either SEQ ID NO: 31 and 32 (construct X) or SEQ ID NO: 33 (construct Y, the control). The DNA substrate designs of the two constructs formed are shown in FIGS. 17 A (after Step 1) and B.

TABLE 6

| Reagent | Construct X | Construct Y | Final Concentrations |
|---|---|---|---|
| Water | 0.5 uL | 3 uL | |
| 0.25M NaCl, 50 mM Tris pH 7.5 | 2 uL | 2 uL | 50 mM, 10 mM |
| SEQ ID NO: 30 (100 uM) | 2.5 uL | 2.5 uL | 25 uM |
| SEQ ID NO: 31 (100 uM) | 2.5 uL | | 25 uM |
| SEQ ID NO: 32 (100 uM) | 2.5 uL | | 25 uM |
| SEQ ID NO: 33 (100 uM) | | 2.5 uL | 25 uM |
| Total | 10 uL | 10 uL | |

2.2 USER Digest of Construct X

An aliquot of the construct X solution that was annealed in the previous step was then treated with USER™ digest in order to remove the dUMP from SEQ ID NO: 32. See Table 7 below for appropriate volumes and concentrations. The sample was then incubated at 37° C. for 30 minutes before it was cooled in an ice block.

TABLE 7

| Reagent | Construct X | Final Concentrations |
|---|---|---|
| Water | 22.8 uL | |
| Construct X (25 uM) | 1.2 uL | 1 uM (30 pmol) |
| 10x DNA ligase buffer | 3 uL | 1x |
| USER (1 U/uL) | 3 uL | 3 U |
| Total | 30 uL | |

2.3 Repair of Single-Stranded Gap in the Double-Stranded DNA Construct

The construct X sample produced after treatment with USER™ was then aliquoted out into three batches of 10 μL. One batch was treated with DNA polymerase only (3 in Table 8), the second was treated with DNA polymerase and ligase (4 in Table 8) and the third was not incubated with either enzyme as a control (2 in Table 8). An additional control experiment (1 in Table 8) was also run where the ds construct Y was incubated in buffer only (in the absence of both polymerase and ligase). Samples 1-4 of Table 8 were incubated for 30 minutes at 16° C. and then EDTA (0.5 M, 5 μL) was added to each sample. A PCR purification kit was then used to purify each sample, which was eluted in 20 μL.

TABLE 8

| Reagent | 1 | 2 | 3 | 4 | Final Concentrations |
|---|---|---|---|---|---|
| Water | 17.2 uL | 7.6 uL | 7.1 uL | 6.6 uL | |
| Construct X sample from Table 7 (1 uM) | | 10 uL | 10 uL | 10 uL | 0.5 uM |
| Construct Y sample from Table 7 (25 uM) | 0.4 uL | | | | 0.5 uM |
| 10x DNA ligase buffer | 2 uL | 2 uL | 2 uL | 2 uL | 1x |
| dNTPs (10 mM) | 0.4 uL | 0.4 uL | 0.4 uL | 0.4 uL | 200 uM |
| T4 DNAP exo(−) | | | 0.5 uL | 0.5 uL | |
| Quick Ligase (T4 DNA ligase) | | | | 0.5 uL | 1x |
| Total | 20 uL | 20 uL | 20 uL | 20 uL | |

2.4 Digestion of DNA Samples

Aliquots (8.5 μL) of samples 1-4 in Table 8 were then subjected to either T7 digestion conditions or a control incubation in buffer in the absence of enzyme (see Table 9 below). The samples were incubated at 37° C. for 5 minutes and then EDTA was added to each sample (0.5 M, 5 μL). Finally, all eight samples (a-h) were run on an Agilent 1000 chip (See FIG. 18).

TABLE 9

| Reagent | a | b | c | d | e | f | g | h | Final Concentration |
|---|---|---|---|---|---|---|---|---|---|
| Water | 0.5 uL | | 0.5 uL | | 0.5 uL | | 0.5 uL | | |
| 1 from Table 8 (0.5 uM) | 8.5 uL | 8.5 uL | | | | | | | 0.4 uM |
| 2 from Table 8 (0.5 uM) | | | 8.5 uL | 8.5 uL | | | | | |
| 3 from Table 8 (0.5 uM) | | | | | 8.5 uL | 8.5 uL | | | |
| 4 from Table 8 (0.5 uM) | | | | | | | 8.5 uL | 8.5 uL | |

TABLE 9-continued

| Reagent | a | b | c | d | e | f | g | h | Final Concentration |
|---|---|---|---|---|---|---|---|---|---|
| 10x NEBuffer 4 | 1 uL | 1 uL | 1 uL | 1 uL | 1 uL | 1 uL | 1 uL | 1 uL | 1x |
| T7 |  | 0.5 uL |  | 0.5 uL |  | 0.5 uL |  | 0.5 uL | 1x |
| Total | 10 uL | 10 uL | 10 uL | 10 uL | 10 uL | 10 uL | 10 uL | 10 uL |  |

Figure 18:
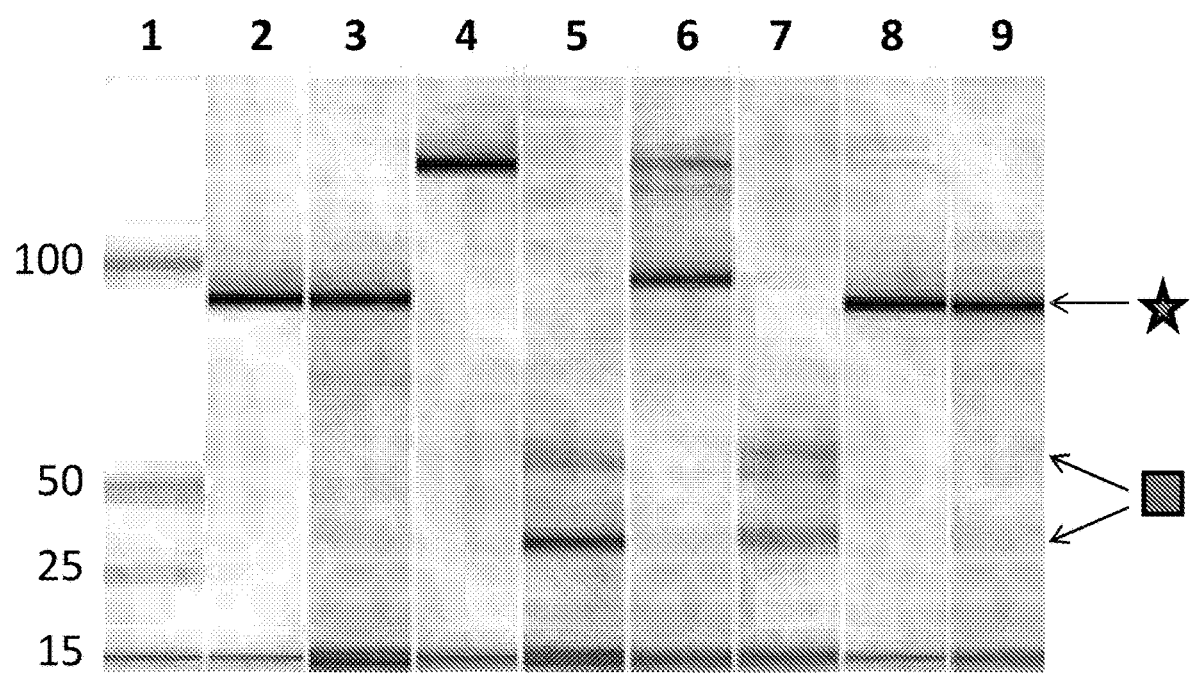
FIG. 18 shows an Agilent 1000 chip which had the following samples contained in lanes 1-9–lane 1=appropriate DNA ladder, lane 2=control sample a (contained construct Y, no digestion), lane 3=control sample b (contained construct Y after digestion), lane 4=control sample c (contained construct X which had not been exposed to polymerase or ligase, no digestion), lane 5=control sample d (contained construct X which had not been exposed to polymerase or ligase after digestion), lane 6=control sample e (contained construct X which had been exposed to polymerase only, no digestion), lane 7=control sample f (contained construct X which had been exposed to polymerase only, after digestion), lane 8=control sample g (contained construct X which had been exposed to polymerase and ligase, no digestion), lane 9=control sample h (contained construct X which had not been exposed to polymerase and ligase, after digestion). The band marked with a star corresponded to undigested dsDNA constructs and the bands marked with a square corresponded to digested DNA.

FIG. 18 shows that construct Y had not been digested by the T7 enzyme because it was a ds DNA construct with no single-stranded DNA gaps (FIG. 18 lane 3). Construct X was susceptible to digestion when it had not been exposed to either DNA polymerase or DNA ligase (see col. 5 of FIG. 18) or when construct X had only been exposed to DNA polymerase (T7 enzyme) (col. 7 of FIG. 18). When construct X had been treated with both DNA polymerase, to fill in the gap in the upper strand, and then ligase, to join the short fragments of DNA together, it was not susceptible to digestion by T7 enzyme (col. 9 of FIG. 18). Therefore, but treating construct X with USER, then DNA polymerase and ligase, it was possible to fill in the single-stranded DNA gap and form a complementary strand of DNA (SEQ ID NO: 33) to the DNA template (SEQ ID NO: 30).

Example 3

Figure 19:
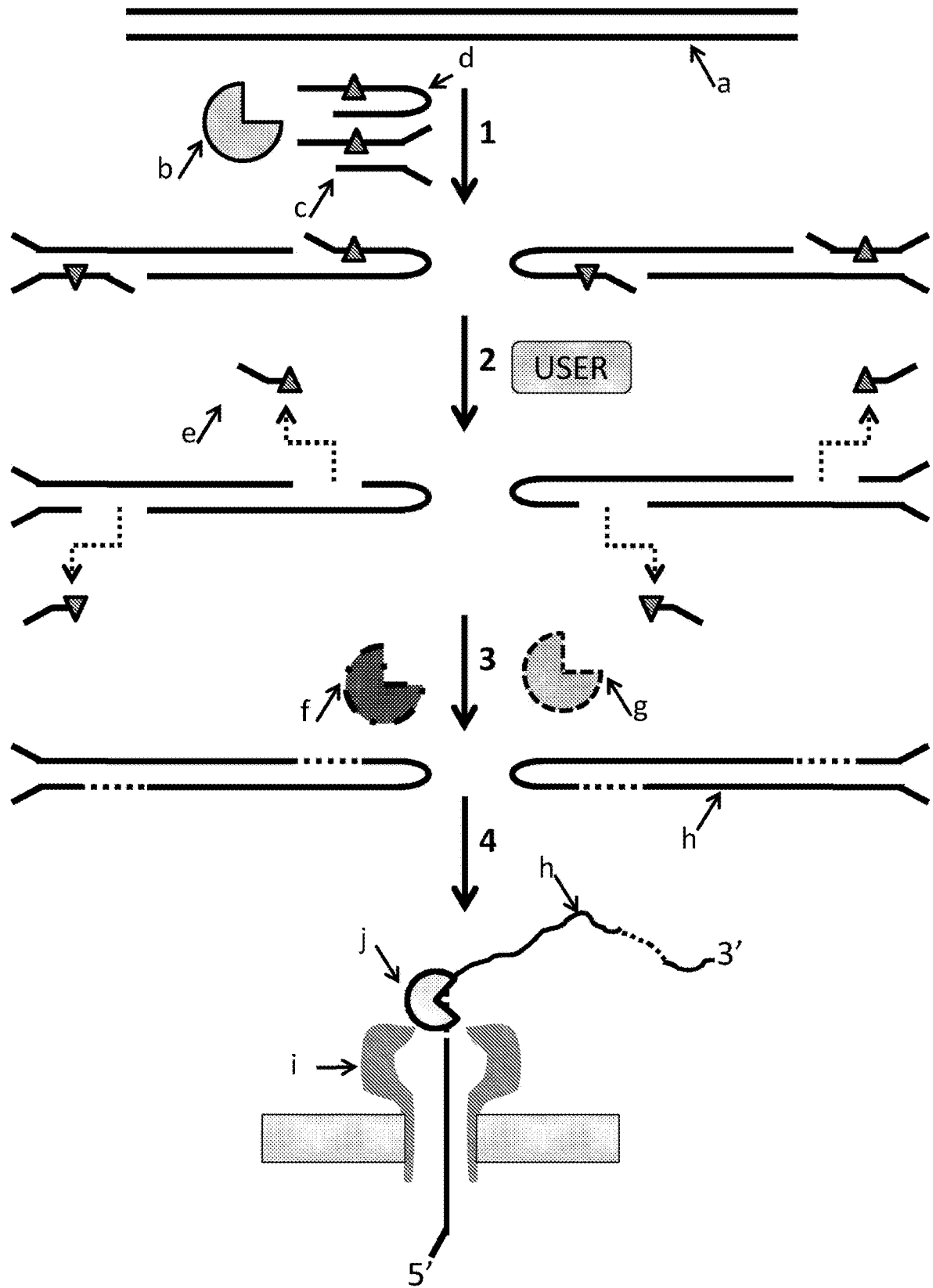
FIG. 19 shows a cartoon representation of the sample preparation procedure used in example 3. In step 1 the double-stranded Lambda DNA (SEQ ID NO: 29, labelled a) was contacted with a MuA transposase (b) and a population of double-stranded hairpin MuA substrates (d) and Y-shaped MuA substrates (c). Both types of MuA substrate contained a single dUMP labelled as a triangle. The MuA transposase fragmented the lambda DNA into 5-10 kB fragments and inserted the MuA substrates at each side of the point of fragmentation (Step 1). The Uracil-Specific Excision Reagent (USER™) then generated a single nucleotide gap at the location of any dUMPs (triangle) which allowed the removal of the DNA fragments which contained the dUMP (e) (Step 2). The single stranded DNA gaps which were left in the fragmented double-stranded construct were then repaired using a DNA polymerase (f), which filled in the gaps with the appropriate complementary nucleotides, and a DNA ligase (g), which ligates the newly synthesised strand to the double stranded construct comprising a single-stranded gap (Step 3). In step 4, the resultant Lambda DNA construct (h) then translocated through a nanopore (i) under the control of a helicase enzyme (j).

This example describes the sample preparation process described in FIG. 19 which was used to fragment Lambda DNA into ~5-10 kB fragments. The fragments which were produced by the sample prep were then passed through a nanopore, with their movement controlled by a helicase enzyme. Markers which were present in the Y-shaped MuA substrates and the hairpin MuA substrates (iSpC3 spacers) that were inserted into the double-stranded Lambda DNA (SEQ ID NO: 29 shows the template strand sequence only) were identified by characteristic current blockades. The observance of the characteristic blocks showed that the sample preparation procedure had been successful.

Figure 20:
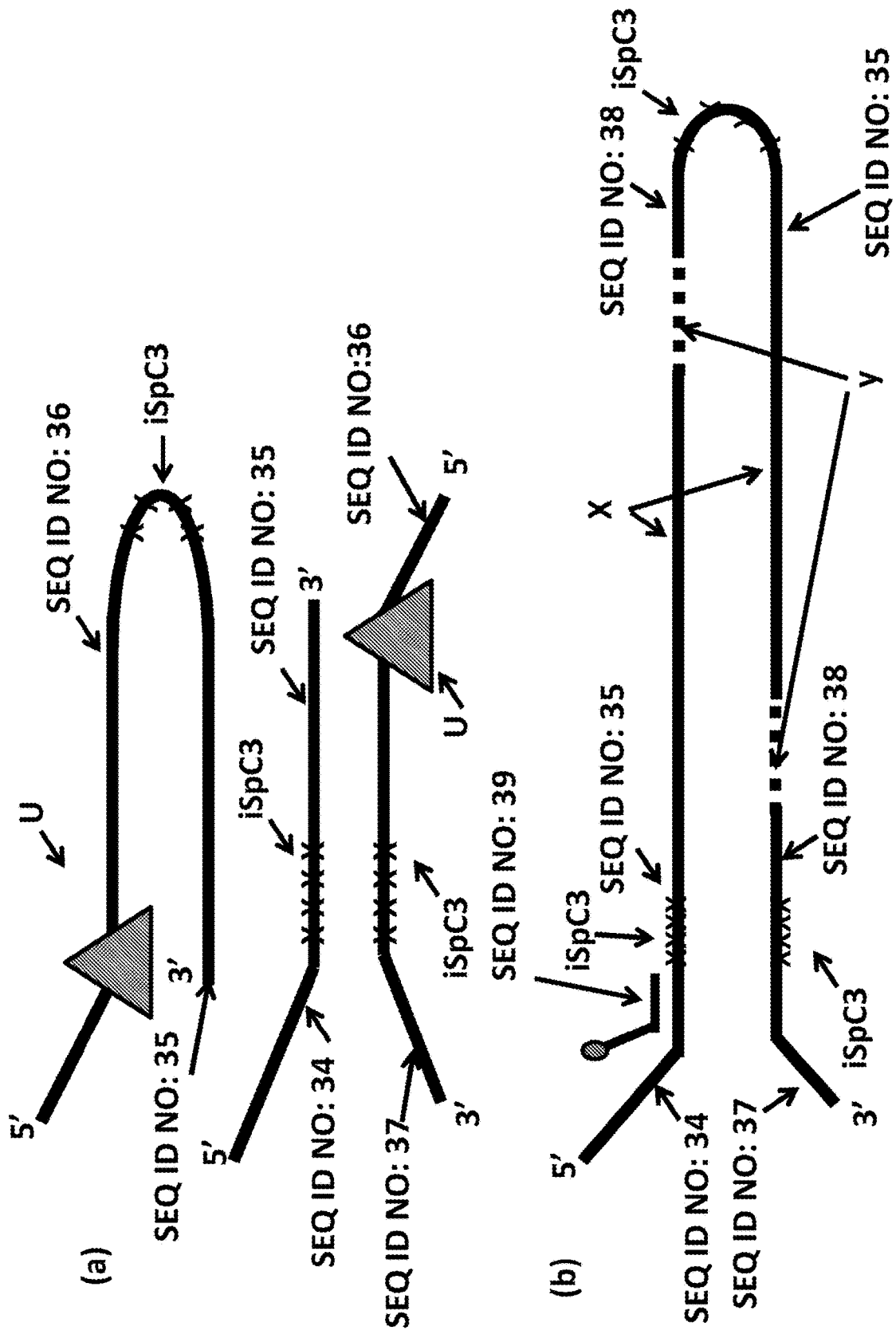
FIG. 20 (*a*) shows the hairpin and Y-shaped MuA substrate designs used in Example 3. The dUMP in SEQ ID NO: 36 is highlighted as a triangle and the iSpC3 spacers are shown as x's.

Materials and Methods 3.1 Anneal of DNA Strands to Form Y-Shaped and Hairpin MuA Substrates The Y-shaped and hairpin MuA substrates were prepared as shown in Table 10 below. The sample mixtures which contained the DNA to form the Y-shaped and hairpin MuA substrates were then heated to 95° C. for 2 minutes and then cooled to 16° C. at a rate of 2° C. per minute. This allowed SEQ ID NOS: 34 and 35 (where SEQ ID NO: 34 attached at its 3' end to the 5' end of SEQ ID NO: 35 by four iSpC3 spacer units) to anneal to SEQ ID NOS: 36 and 37 (where SEQ ID NO: 36 attached at its 3' end to the 5' end of SEQ ID NO: 37 by four iSpC3 spacer units) to form the Y-shaped MuA substrate and for SEQ ID NOS: 36 and 35 (where SEQ ID NO: 36 attached at its 3' end to the 5' end of SEQ ID NO: 35 by four iSpC3 spacer units) to form a hairpin loop MuA substrate. The DNA substrate designs of the two MuA substrates formed are shown in FIG. 20 (a).

TABLE 10

| Reagent | Y-shaped | Hairpin | Final Concentrations |
|---|---|---|---|
| Water | 12 uL | 14 uL |  |
| 0.5M NaCl | 2 uL | 2 uL | 50 mM |
| 0.1M Tris pH 7.5 | 2 uL | 2 uL | 10 mM |
| SEQ ID NO: 34 and 35 (where SEQ ID NO: 34 attached at its 3' end to the 5' end of SEQ ID NO: 35 by four iSpC3 spacer units) (100 uM) | 2 uL |  | 10 uM |
| SEQ ID NO: 36 and 37 (where SEQ ID NO: 36 attached at its 3' end to the 5' end of SEQ ID NO: 37 by four iSpC3 spacer units) (100 uM) | 2 uL |  | 10 uM |
| SEQ ID NO: 36 and 35 (where SEQ ID NO: 36 attached at its 3' end to the 5' end of SEQ ID NO: 35 by four iSpC3 spacer units) (100 uM) |  | 2 uL | 10 uM |
| Total | 20 uL | 20 uL |  |

3.2 Fragmentation of the DNA Template Using the MuA Transposase

Double-stranded Lambda DNA (SEQ ID NO: 29 shows the template strand only) was fragmented into approximately 5-10 kB length strands using a MuA transposase. The MuA transposase inserted the MuA substrates (the Y-shaped and the hairpin MuA substrates) which were annealed in section 3.1. The sample was prepared as shown in Table 11 below. The sample was then incubated at 30° C. for 1 hour and heat inactivated at 75° C. for 10 minutes. The sample was then further purified using a PCR Purification kit and eluted in 26 µL.

TABLE 11

| Reagent | Sample Volume 1 | Final Concentrations |
|---|---|---|
| Water | 17.7 uL |  |
| Lambda DNA (90 ng/uL) (SEQ ID NO: 29 shows the template strand sequence only) | 22.3 uL | 2 µg |
| Y-shaped MuA substrate (1 uM) | 8 uL | 100 nM |
| Hairpin MuA substrate (1 uM) | 8 uL | 100 nM |
| 5x Buffer (125 mM Tris (pH 8.0), 50 mM MgCl$_2$, 550 mM NaCl, 0.25% Triton X-100 and 50% Glycerol) | 16 uL | 1x |
| MuA (4 uM, Thermo, catalogue No. F-750C) | 8 uL | 400 nM |
| Total | 80 uL |  |

3.3 USER Digest of Fragmented Lambda DNA with Inserted MuA Substrates

Purified sample volume 1 from step 3.2 was then treated with USER™ digest in order to remove the dUMP from SEQ ID NO: 36. See Table 12 below for appropriate volumes and concentrations. The sample was then incubated at 37° C. for 30 minutes before it was cooled in an ice block.

TABLE 12

| Reagent | Sample Volume 2 | Final Concentrations |
|---|---|---|
| Sample Volume 1 | 26 uL | 8 pmol of U |
| 10x DNA ligase buffer | 3 uL | 1x |
| USER (1 U/uL) | 1 uL | 1 U |
| Total | 30 uL | |

3.4 Repair of Single-Stranded Gap in the Double-Stranded Lambda DNA Construct Fragments Sample Volume 2 produced after treatment with USER™ was then treated with DNA polymerase and ligase in order to close the single-stranded gap. Sample volume 3 (see table 13 below for appropriate volumes and concentrations) was incubated for 30 minutes at 16° C. and then EDTA (0.5 M, 10 µL) was added to sample volume 3. A PCR Purification kit was then used to purify each sample, which was eluted in 50 µL of water. An aliquot of the purified sample (1 µL) was run on an Agilent 12000 chip to quantify the sample and Tris-HCl and NaCl (pH 7.5) were added to the rest of the sample until the concentrations were 10 mM and 50 mM respectively. Finally, SEQ ID NO: 39 (3' end of the sequence had six iSp18 spacers attached to two thymine residues and a 3' cholesterol TEG, 0.5 µM) was annealed to the purified sample.

TABLE 13

| Reagent | Sample Volume 3 | Final Concentrations |
|---|---|---|
| Water | 6.2 uL | |
| Sample Volume 2 | 30 uL | |
| 10x DNA ligase buffer | 1 uL | 1x |
| dNTPs (10 mM) | 0.8 uL | 200 uM |
| T4 DNAP exo(−) (Lucigen) | 1 uL | |
| Ligase (NEB; M0202M) | 1 uL | 1x |
| Total | 40 uL | |

3.5 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which had the Y-shaped MuA substrates and the hairpin MuA substrates attached to either end of the fragments by the MuA transposase (see FIG. 20 (b) for an example construct)) and Trwc Cba (SEQ ID NO: 40, 1 µM) were pre-incubated together for 1 hour in buffer (50 mM CAPS, pH 10.0 (pH altered to pH 10.0 by addition of NaOH), 100 mM NaCl).

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (600 mM KCl, 25 mM KH2PO4, 75 mM Potassium Ferrocyanide (II), 25 mM Potassium ferricyanide (III), pH 8). After a single pore in the bilayer was achieved, then buffer (1 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MS(B1-G75S/G77S/L88N/Q126R)8 MspA (SEQ ID NO: 2 with mutations G75S/G77S/L88N/Q126R) and the experimental system was placed on a cooler plate set to 8° C. which gave a system temperature of ~15° C. $MgCl_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cba (SEQ ID NO: 40, 1 µM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

3.6 Results and Discussion

Figure 21:
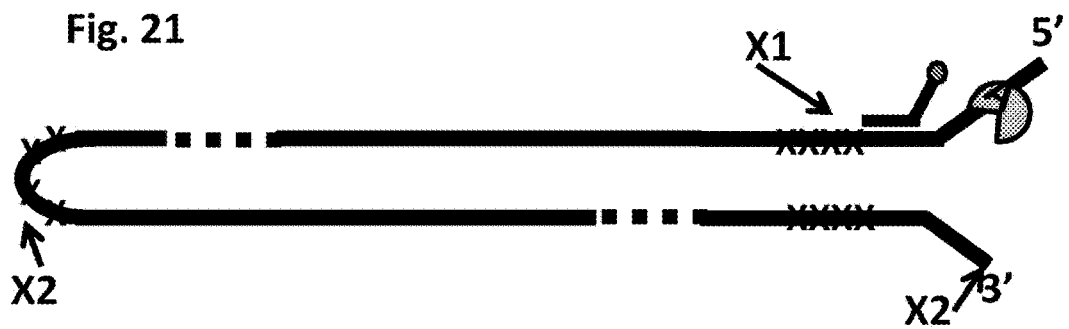
FIG. 21 shows example current traces (y-axis label=Current (pA), x-axis label=Time (s) for both upper and lower traces) of when a helicase (Trwc Cba (SEQ ID NO: 40, labelled A) controlled the translocation of the Lambda DNA construct (shown in FIG. 20 (*b*)) through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produced the spike in current labelled 1 and the second iSpC3 spacers labelled X2 produced the spike in current labelled 2. The lower trace shows a zoomed in region of the end of the helicase controlled DNA movement through the nanopore, the third iSpC3 spacer labelled X3 produced the spike in current labelled 3.
Figure 21:
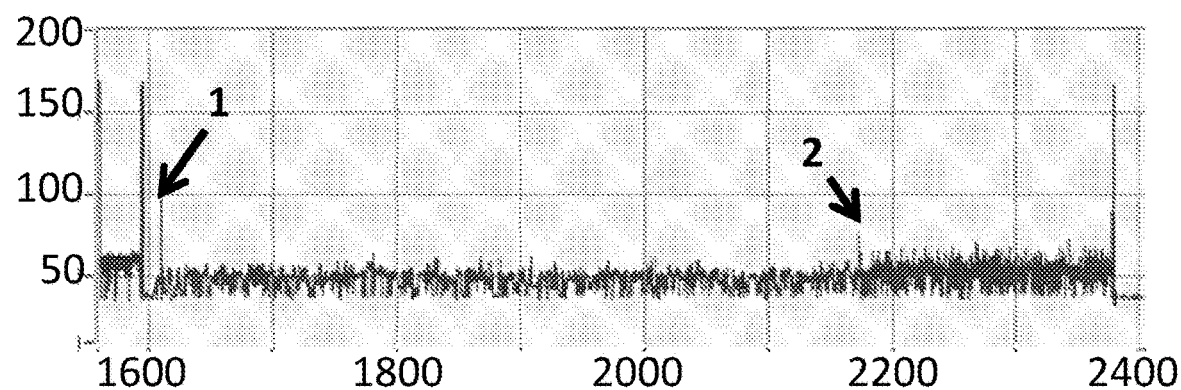
Figure 21:
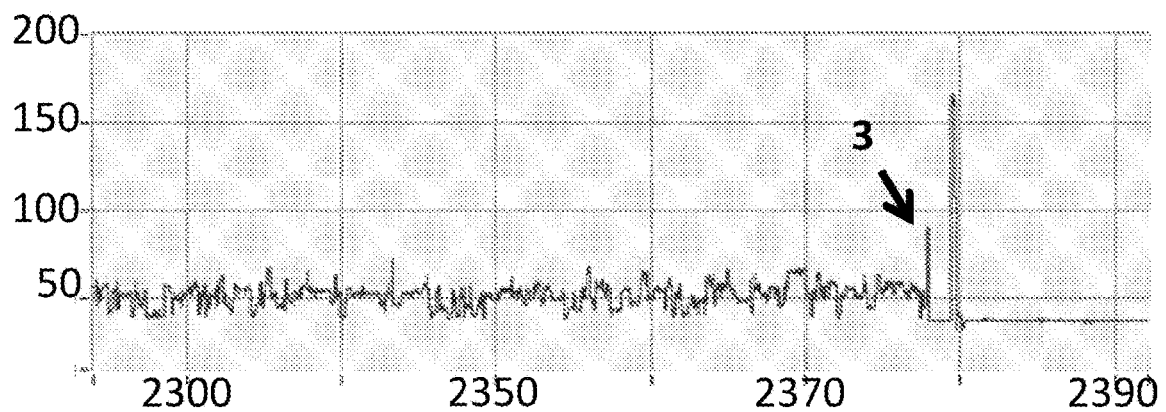

Helicase controlled DNA movement was observed for the Lambda DNA construct, an example of a helicase-controlled DNA movement is shown in FIG. 21. The iSpC3 spacers present in the Lambda DNA construct produced a characteristic block level highlighted by the numbers 1, 2 and 3 in FIG. 21. The Y-shaped MuA substrate had four iSpC3 spacers in either strand and the hairpin MuA substrate also had four iSpC3 spacers, each iSpC3 spacer allowed more current to flow as that region of the Lambda DNA construct translocated through the nanopore. If the sample preparation had occurred successfully then the iSpC3 spacer events would have been observed at the beginning of the Lambda DNA construct, in the middle (marking the transition between template and template complement sequences) and at the end. FIG. 21 clearly shows three instances of increased current flow which corresponded to the iSpC3 spacer regions. Therefore, the sample preparation procedure effectively introduced MuA substrates into the Lambda DNA and produced the Lambda DNA constructs shown in FIG. 20 (b).

Example 4

Figure 22:
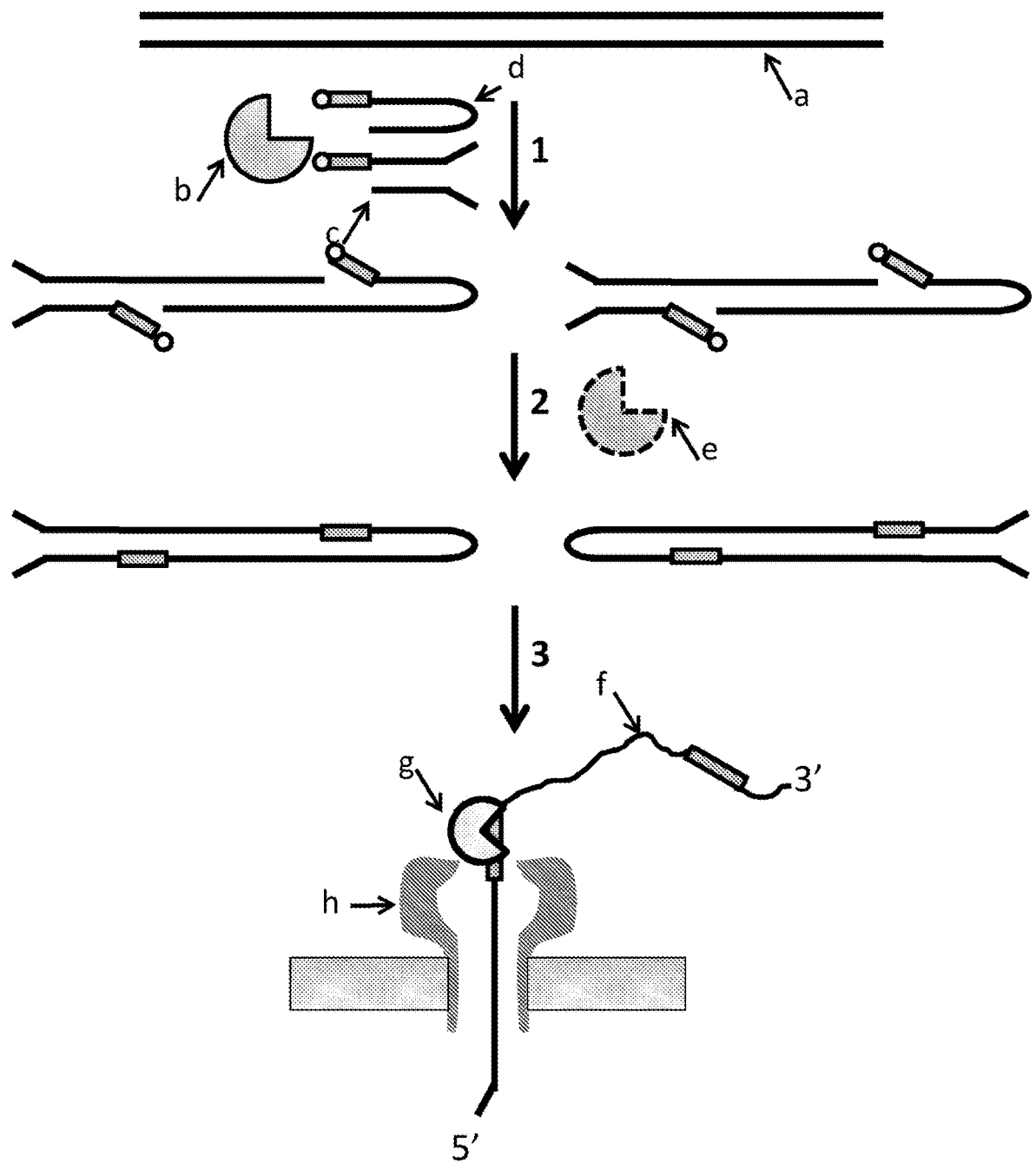
FIG. 22 shows a cartoon representation of the sample preparation procedure used in example 3. In step 1 the double-stranded Lambda DNA (SEQ ID NO: 29, labelled a) was contacted with a MuA transposase (b) and a population of double-stranded hairpin 2 MuA substrates (d) and Y-shaped 2 MuA substrates (c). Both types of MuA substrate contained a 5'phosphate (labelled as a circle) and five inosines (labelled as a rectangle). The MuA transposase fragmented the lambda DNA into 5-10 kB fragments and inserted the MuA substrates at each side of the point of fragmentation (Step 1). The nicks which wee left in the fragmented double-stranded construct wee then repaired using a DNA ligase (e), which ligated the strand that contained the inosines to the double stranded Lambda DNA construct (Step 2). In step 3, the resultant Lambda DNA construct (f) then translocated through a nanopore (h) under the control of a helicase enzyme (g).

This example describes an alternative sample preparation process illustrated in FIG. 22 which was used to fragment Lambda DNA into ~5-10 kB fragments. The fragments which were produced by the sample prep were then passed through a nanopore, with their movement controlled by a helicase enzyme. Markers which were present in the Y-shaped MuA substrates and the hairpin MuA substrates (iSpC3 spacers) that were inserted into the double-stranded Lambda DNA (SEQ ID NO: 29 shows the template strand sequence only) were identified by characteristic current blockades. The observance of the characteristic blockades showed that the sample preparation procedure had been successful.

Figure 23:
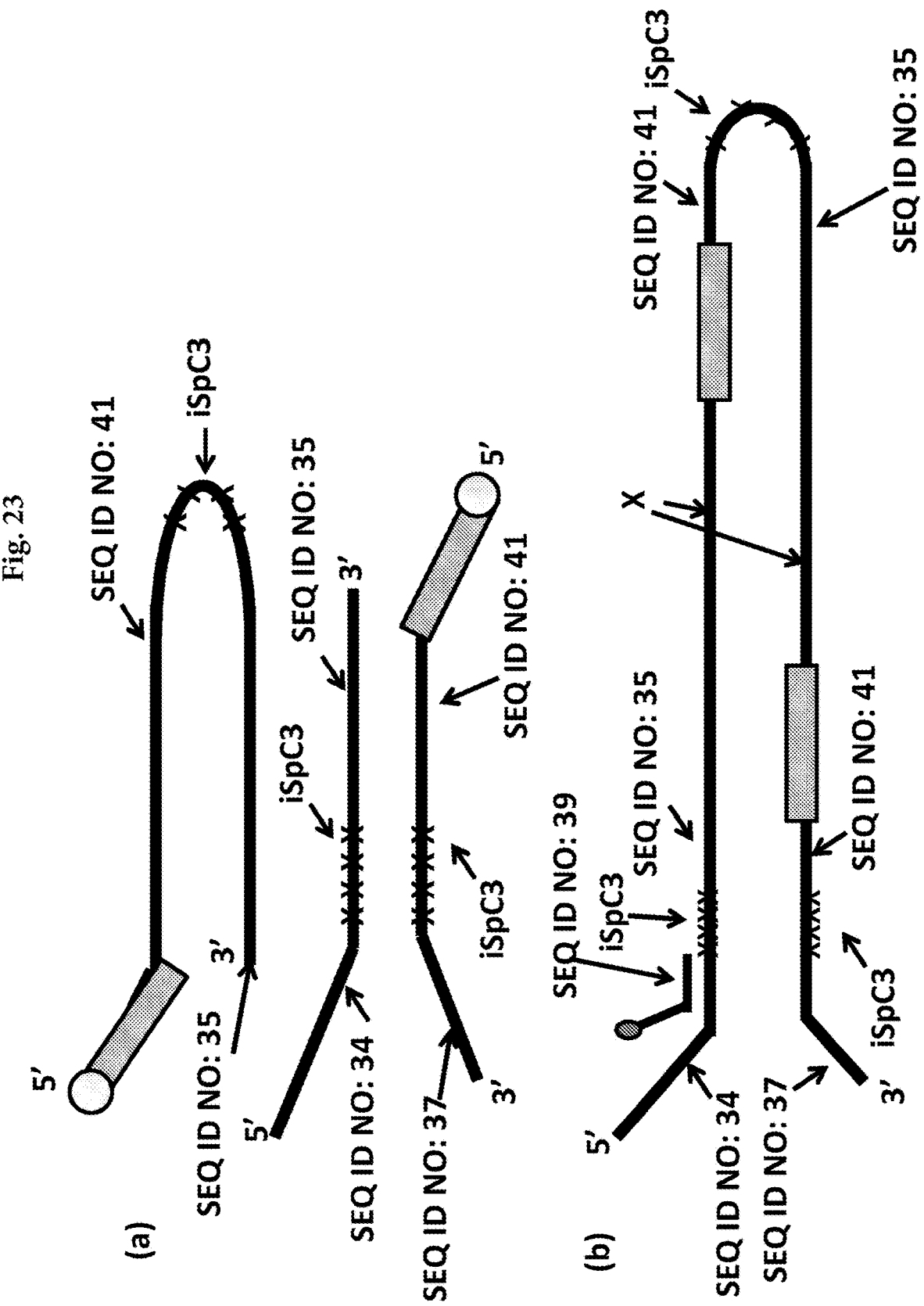
FIG. 23 (a) shows the hairpin 2 and Y-shaped 2 MuA substrate designs used in Example 4. The 5' phosphate is labelled as a circle, the inosines in SEQ ID NO: 41 are highlighted as a rectangle and the iSpC3 spacers are shown as x's.

Materials and Methods 4.1 Anneal of DNA Strands to Form Y-Shaped and Hairpin MuA Substrates The Y-shaped and hairpin MuA substrates were prepared as described in Example 3.1 above. Volumes, concentrations and sequences that were used in this example are detailed in table 14 below. The DNA substrate designs of the two constructs formed are shown in FIG. 23 (a).

TABLE 14

| Reagent | Y-shaped 2 | Hairpin 2 | Final Concentrations |
|---|---|---|---|
| Water | 12 uL | 14 uL | |
| 0.5M NaCl | 2 uL | 2 uL | 50 mM |
| 0.1M Tris pH 7.5 | 2 uL | 2 uL | 10 mM |
| SEQ ID NO: 34 and 35 (where SEQ ID NO: 34 is attached at its 3' end to the 5' end of SEQ ID NO: 35 by four iSpC3 spacer units) (100 uM) | 2 uL | | 10 uM |

TABLE 14-continued

| Reagent | Y-shaped 2 | Hairpin 2 | Final Concentrations |
|---|---|---|---|
| SEQ ID NO: 41 and 37 (where SEQ ID NO: 41 is attached at its 3' end to the 5' end of SEQ ID NO: 37 by four iSpC3 spacer units) (100 uM) | 2 uL | | 10 uM |
| SEQ ID NO: 41 and 35 (where SEQ ID NO: 41 is attached at its 3' end to the 5' end of SEQ ID NO: 35 by four iSpC3 pacer units) (100 uM) | | 2 uL | 10 uM |
| Total | 20 uL | 20 uL | |

4.2 Fragmentation of the DNA Template Using the MuA Transposase

Double-stranded Lambda DNA (SEQ ID NO: 29) was fragmented into approximately 5-10 kB length strands using a MuA transposase. The MuA transposase inserted the MuA substrates (the Y-shaped 2 and the hairpin 2 MuA substrates) which were annealed in section 4.1. The sample was prepared by an analogous procedure as that described in Section 3.2 and table 11 above except the MuA substrates used were the Y-shaped 2 and the hairpin 2 MuA substrates. In this case the purified sample X was eluted in a volume of 20 μL.

4.3 Nick Repair in the Double-Stranded Lambda DNA Construct Fragments

Once the Y-shaped 2 and the hairpin 2 MuA substrates had been inserted into the fragmented Lambda DNA it was necessary to repair the nick in the strand and join the inosines to the Lambda DNA fragment to produce a complete double-stranded Lambda DNA fragment. The reaction was assembled on ice as described in Table 15 below. The sample was incubated at 16° C. for 60 mins before EDTA (10 μL, 0.5 M) was added to the sample. The resultant sample mixture was purified and was eluted in 50 μL of water. An aliquot of the purified sample (1 μL) was run on an Agilent 12000 chip to quantify the sample and Tris-HCl and NaCl (pH 7.5) were added to the rest of the sample until the concentrations were 10 mM and 50 mM respectively. Finally, SEQ ID NO: 39 (3' end of the sequence had six iSp18 spacers attached to two thymine residues and a 3' cholesterol TEG, 0.5 μM) was annealed to the purified Lambda DNA construct.

TABLE 15

| Reagent | Sample Z | Final Concentrations |
|---|---|---|
| Sample X | 16 uL | |
| 2x DNA ligase buffer | 20 uL | 1x |
| Ligase (NEB; M0202M) | 4 uL | |
| Total | 40 uL | |

4.4 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which had the Y-shaped 2 and the hairpin 2 MuA substrates attached to either end of the fragments by the MuA transposase (see FIG. 23 (b) for an example construct)) and Trwc Cba (SEQ ID NO: 40, 1 μM) were pre-incubated together for 1 hour in buffer (50 mM CAPS, pH 10.0 (pH altered to pH 10.0 by addition of NaOH), 100 mM NaCl).

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (600 mM KCl, 25 mM KH2PO4, 75 mM Potassium Ferrocyanide (II), 25 mM Potassium ferricyanide (III), pH 8). After achieving a single pore in the bilayer, then buffer (3 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MS(B1-G75S/G77S/L88N/Q126R)8 MspA (SEQ ID NO: 2 with mutations G75S/G77S/L88N/Q126R) and the experimental system was placed on a cooler plate set to 8° C. which gave a system temperature of −15° C. $MgCl_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cba (SEQ ID NO: 40, 1 μM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

4.5 Results and Discussion

Figure 24:
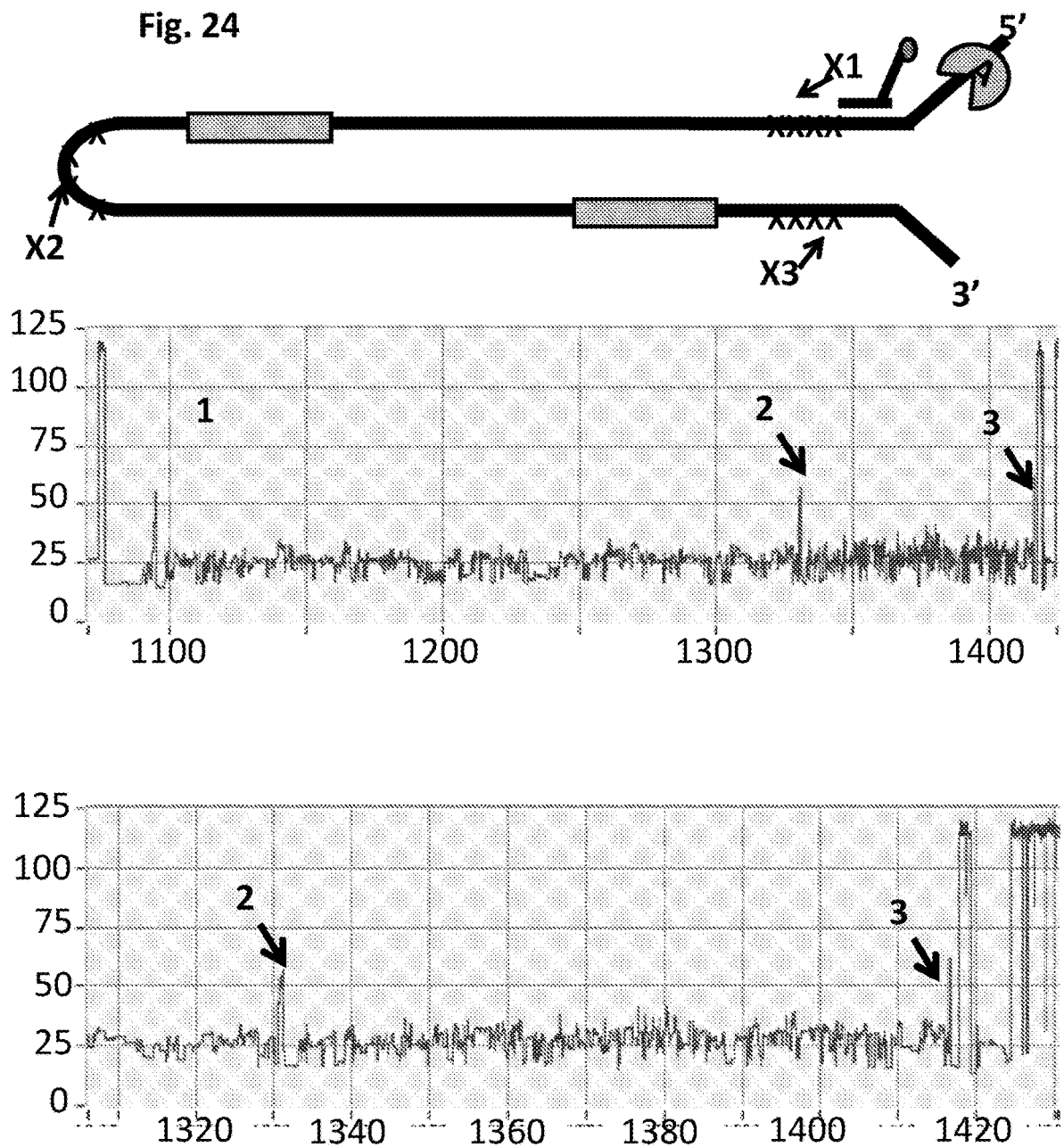
FIG. 24 shows example current traces (y-axis label=Current (pA), x-axis label=Time (s) for both upper and lower traces) of when a helicase (Trwc Cba (SEQ ID NO: 40, labelled A) controlled the translocation of the Lambda DNA construct through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produced the spike in current labelled 1, the second iSpC3 spacer labelled X2 produced the spike in current labelled 2 and the third iSpC3 spacer labelled X3 produced the spike in current labelled 3. The lower trace shows a zoomed in region of the second half of the helicase controlled DNA movement through the nanopore, the second iSpC3 spacer labelled X2 produced the spike in current labelled 2 and the third iSpC3 spacer labelled X3 produced the spike in current labelled 3.

Helicase controlled DNA movement was observed for the Lambda DNA construct, an example of a helicase-controlled DNA movement is shown in FIG. 24. The iSpC3 spacers present in the Lambda DNA construct produced a characteristic block level highlighted by numbers 1-3 in FIG. 24. The Y-shaped 2 MuA substrate had four iSpC3 spacers in either strand and the hairpin 2 MuA substrate also had four iSpC3 spacers, each iSpC3 spacer allowed more current to flow as that region of the Lambda DNA construct translocated through the nanopore. If the sample preparation had occurred successfully then the iSpC3 spacer events would have been observed at the beginning of the Lambda DNA construct, in the middle (making the transition between the template and template complement strands) and at the end. FIG. 24 clearly shows three instances of increased current flow which corresponded to the iSpC3 spacer regions. Therefore, the sample preparation procedure effectively introduced MuA substrates into the Lambda DNA and produced the Lambda DNA constructs shown in FIG. 23 (b). Owing to the use of the inosines in the Y-shaped 2 and the hairpin 2 MuA substrates, the steps in the sample preparation procedure were reduced as once the MuA substrates had been inserted all that was necessary was to close the nicks in the double-stranded DNA constructs.

The invention claimed is:

1. A method for modifying a template double stranded polynucleotide, comprising:
   (a) contacting the template polynucleotide with a MuA transposase and a population of double stranded MuA substrates each comprising (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby producing a plurality of fragment/substrate constructs;
   (b) removing the overhangs from the constructs by selectively removing the at least one nucleotide and thereby producing a plurality of double stranded constructs comprising single stranded gaps; and
   (c) repairing the single stranded gaps in the constructs and thereby producing a plurality of modified double stranded polynucleotides.

2. A method according to claim 1, wherein the template polynucleotide comprises the nucleosides deoxyadenosine (dA), deoxyuridine (dU) and/or thymidine (dT), deoxyguanosine (dG) and deoxycytidine (dC).

3. A method according to claim 1, wherein the nucleoside that is not present in the template polynucleotide is abasic, adenosine (A), uridine (U), 5-methyluridine (m5U), cytidine (C) or guanosine (G) or comprises urea, 5, 6 dihydroxythymine, thymine glycol, 5-hydroxy-5 methylhydanton, uracil glycol, 6-hydroxy-5, 6-dihdrothimine, methyltartronylurea, 7, 8-dihydro-8-oxoguanine (8-oxoguanine), 8-oxoadenine, fapy-guanine, methy-fapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer.

4. A method according to claim 1, wherein the at least one nucleotide is 10 nucleotides or fewer from the overhang.

5. A method according to claim 1, wherein the at least one nucleotide is the first nucleotide in the overhang.

6. A method according to claim 1, wherein all of the nucleotides in the overhang comprise a nucleoside that is not present in the template polynucleotide.

7. A method according to claim 1, wherein each substrate comprises an overhang at one end and a hairpin loop at the other end and wherein the two strands of the modified double stranded polynucleotides produced by the method are linked by the hairpin loop at one or both ends.

8. A method according to claim 1, wherein each substrate is a Y substrate with an overhang at one end and a region that is not complementary at the other end and wherein the modified double stranded polynucleotides produced by the method have the non-complementary region at one or both ends.

9. A method according to claim 1, wherein a proportion of the substrates in the population comprise an overhang at one end and a hairpin loop at the other end and a proportion of the substrates in the population are Y substrates with an overhang at one end and a region that is not complementary at the other end and wherein at least some of the modified double stranded polynucleotides produced by the method have the hairpin loop at one end and the non-complementary region at the other end.

10. A method according to claim 1, wherein the substrate comprises a selectable binding moiety.

11. A method according to claim 7, wherein the method further comprises separating the two strands of at least one modified double stranded polynucleotide to produce at least one single stranded polynucleotide comprising one strand of the modified double stranded polynucleotide linked to the other strand of the modified double stranded polynucleotide.

12. A method of characterising at least one polynucleotide modified using a method according to claim 1, comprising:
   a) contacting the modified polynucleotide with a transmembrane pore such that at least one strand of the polynucleotide moves through the pore; and
   b) taking one or more measurements as the at least one strand moves with respect to the pore wherein the measurements are indicative of one or more characteristics of the at least one strand and thereby characterising the modified polynucleotide.

13. A method of characterising a template polynucleotide, comprising:
   a) modifying the template polynucleotide using a method according to claim 1 to produce a plurality of modified polynucleotides;
   b) contacting each modified polynucleotide with a transmembrane pore such that at least one strand of each polynucleotide moves through the pore; and c) taking one or more measurements as the at least one strand of each polynucleotide moves with respect to the pore wherein the measurements are indicative of one or more characteristics of the at least one strand of each polynucleotide and thereby characterising the template polynucleotide.

14. A method according to claim 13, wherein the one or more characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified.

15. A method according to claim 13, wherein step (b) further comprises contacting each modified polynucleotide with a polynucleotide binding protein such that the protein controls the movement of the at least one strand of each polynucleotide through the pore.

16. A method according to claim 15, wherein the method comprises (a) contacting each modified polynucleotide with a transmembrane pore and a polynucleotide binding protein such that at least one strand of each polynucleotide moves through the pore and the protein controls the movement of the at least one strand of each polynucleotide through the pore; and (b) measuring the current passing through the pore as the at least one strand of each polynucleotide moves with respect to the pore wherein the current is indicative of one or more characteristics of the at least one strand of each polynucleotide and thereby characterising the template polynucleotide.

17. A method according to claim 15, wherein the polynucleotide binding protein is derived from a helicase.

\* \* \* \* \*

SEQUENCE LISTING

<160> NUMBER OF SEQ ID NOS: 41

<210> SEQ ID NO 1
<211> LENGTH: 558

```
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 1
atgggtctgg ataatgaact gagcctggtg gacggtcaag atcgtaccct gacggtgcaa      60
caatgggata ccttcctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                    558

<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 885
<212> TYPE: DNA
```

```
<213> ORGANISM: Artificial Sequence
<220> FEATURE:
<223> OTHER INFORMATION: alpha-hemolysin mutant E111N/K147N

<400> SEQUENCE: 3
atggcagatt ctgatattaa tattaaaacc ggtactacag atattggaag caatactaca      60
gtaaaaacag gtgatttagt cacttatgat aaagaaaatg gcatgcacaa aaagtatttt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaaaactata tgagtacttt aacttatgga     360
ttcaacggta atgttactgg tgatgataca ggaaaaattg gcggcttat tggtgcaaat      420
gtttcgattg gtcatacact gaactatgtt caacctgatt tcaaaacaat tttagagagc     480
ccaactgata aaaagtagg ctggaaagtg atatttaaca atatggtgaa tcaaaattgg      540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caatatagta gtaatatac gaacgagttc gtgatgatta ccaattgcat      780
tggacttcaa caaattggaa aggtaccaat actaaagata aatggacaga tcgttcttca     840
gaaagatata aatcgattg ggaaaagaa gaaatgacaa attaa                       885
```

<210> SEQ ID NO 4  
<211> LENGTH: 293  
<212> TYPE: PRT  
<213> ORGANISM: Artificial Sequence  
<220> FEATURE:  
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175
```

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

```
Thr Val Gln Gln Trp Asp Thr Phe Leu Asn Gly Val Phe Pro Leu Asp
             20                  25                  30

Arg Asn Arg Leu Thr Arg Glu Trp Phe His Ser Gly Arg Ala Lys Tyr
         35                  40                  45

Ile Val Ala Gly Pro Gly Ala Asp Glu Phe Glu Gly Thr Leu Glu Leu
     50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                 85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
             20                  25                  30

Asn Arg Leu Thr Arg Glu Trp Phe His Ser Gly Arg Ala Thr Tyr His
         35                  40                  45

Val Ala Gly Pro Gly Ala Asp Glu Phe Glu Gly Thr Leu Glu Leu Gly
     50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                 85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 8
<211> LENGTH: 1830
<212> TYPE: DNA
<213> ORGANISM: Bacillus subtilis

<400> SEQUENCE: 8

| | | | | | |
|---|---|---|---|---|---|
| atgaaacaca | tgccgcgtaa | aatgtatagc | tgcgcgtttg | aaaccacgac | caaagtggaa | 60 |
| gattgtcgcg | tttgggccta | tggctacatg | aacatcgaag | atcattctga | atacaaaatc | 120 |
| ggtaacagtc | tggatgaatt | tatggcatgg | gtgctgaaag | ttcaggcgga | tctgtacttc | 180 |
| cacaacctga | aatttgatgg | cgcattcatt | atcaactggc | tggaacgtaa | tggctttaaa | 240 |
| tggagcgcgg | atggtctgcc | gaacacgtat | aataccatta | tctctcgtat | gggccagtgg | 300 |
| tatatgattg | atatctgcct | gggctacaaa | ggtaaacgca | aaattcatac | cgtgatctat | 360 |
| gatagcctga | aaaactgcc | gtttccggtg | aagaaaattg | cgaaagattt | caaactgacg | 420 |
| gttctgaaag | gcgatattga | ttatcacaaa | gaacgtccgg | ttggttacaa | aatcaccccg | 480 |
| gaagaatacg | catacatcaa | aaacgatatc | cagatcatcg | cagaagcgct | gctgattcag | 540 |
| tttaaacagg | gcctggatcg | catgaccgcg | ggcagtgata | gcctgaaagg | tttcaaagat | 600 |
| atcatcacga | ccaaaaaatt | caaaaaagtg | ttcccgacgc | tgagcctggg | tctggataaa | 660 |
| gaagttcgtt | atgcctaccg | cggcggtttt | acctggctga | cgatcgtttt | caaagaaaaa | 720 |
| gaaattggcg | agggtatggt | gtttgatgtt | aatagtctgt | atccggcaca | gatgtacagc | 780 |
| cgcctgctgc | gtatggcgca | accgatcgtg | ttcgagggta | aatatgtttg | ggatgaagat | 840 |
| tacccgctgc | atattcagca | catccgttgt | gaatttgaac | tgaaagaagg | ctatattccg | 900 |
| accattcaga | tcaaacgtag | tcgcttctat | aagggtaacg | aatacctgaa | aagctctggc | 960 |
| ggtgaaatcg | cggatctgtg | gctgagtaac | gtggatctgg | aactgatgaa | agaacactac | 1020 |
| gatctgtaca | acgttgaata | catcagcggc | ctgaaattta | aagccacgac | cggtctgttc | 1080 |
| aaagatttca | tcgataaatg | gacctacatc | aaaacgacct | ctgaaggcgc | gattaaacag | 1140 |
| ctggccaaac | tgatgctgaa | cagcctgtat | ggcaaattcg | cctctaatcc | ggatgtgacc | 1200 |
| ggtaaagttc | cgtacctgaa | agaaaatggc | gcactgggtt | ttcgcctggg | cgaagaagaa | 1260 |
| acgaaagatc | cggtgtatac | cccgatgggt | gttttcatta | cggcctgggc | acgttacacg | 1320 |
| accatcaccg | cggcccaggc | atgctatgat | cgcattatct | actgtgatac | cgattctatt | 1380 |
| catctgacgg | gcaccgaaat | cccggatgtg | attaaagata | tcgttgatcc | gaaaaaactg | 1440 |
| ggttattggg | cccacgaaag | tacgtttaaa | cgtgcaaaat | acctgcgcca | gaaaacctac | 1500 |
| atccaggata | tctacatgaa | agaagtggat | ggcaaactgg | ttgaaggttc | tccggatgat | 1560 |
| tacaccgata | tcaaattcag | tgtgaaatgc | gccggcatga | cggataaaat | caaaaaagaa | 1620 |
| gtgaccttcg | aaaacttcaa | agttggtttc | agccgcaaaa | tgaaaccgaa | accggtgcag | 1680 |
| gttccgggcg | gtgtggttct | ggtggatgat | acgtttacca | ttaaatctgg | cggtagtgcg | 1740 |
| tggagccatc | gcagttcga | aaaaggcggt | ggctctggtg | gcggttctgg | cggtagtgcc | 1800 |
| tggagccacc | gcagtttga | aaaataataa | | | | 1830 |

<210> SEQ ID NO 9
<211> LENGTH: 608
<212> TYPE: PRT
<213> ORGANISM: Bacillus subtilis

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Ile Asp Lys Trp Thr
            355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400
```

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg cgaaccggga agtgttttat tgcaaaccgg ccgatgatta tctgccgcag   180
ccgggtgcgg tgctgattac cggtattacc ccgcaggaag cgcgcgcgaa aggtgaaaac   240
gaagcggcgt ttgccgcgcg cattcatagc ctgtttaccg tgccgaaaac ctgcattctg   300
ggctataaca atgtgcgctt cgatgatgaa gttacccgta atatctttta tcgtaacttt   360
tatgatccgt atgcgtggag ctggcagcat gataacagcc gttgggatct gctggatgtg   420
atgcgcgcgt gctatgcgct cgcccggaa ggcattaatt ggccggaaaa cgatgatggc   480
ctgccgagct tcgtctggaa acatctgacc aaagccaacg gcattgaaca tagcaatgcc   540
catgatgcga tggccgatgt ttatgcgacc attgcgatgg cgaaactggt taaaacccgt   600
cagccgcgcc tgtttgatta tctgtttacc caccgtaaca acacaaaact gatggcgctg   660
attgatgttc gcagatgaa accgctggtg catgtgagcg gcatgtttgg cgcctggcgc   720
ggcaacacca gctgggtggc cccgctggcc tggcacccgg aaaatcgtaa cgccgtgatt   780
atggttgatc tggccggtga tattagcccg ctgctggaac tggatagcga taccctgcgt   840
gaacgcctgt ataccgccaa aaccgatctg gcgataatg ccgccgtgcc ggtgaaactg   900
gttcacatta acaaatgccc ggtgctggcc caggcgaaca ccctgcgccc ggaagatgcg   960
```

```
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taagaaaaaa    1380
gtggcgctgc                                                            1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285
```

Asp Leu Gly Asp Asn Ala Ala Val Pro Val Lys Leu Val His Ile Asn
        290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
            485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc     60
atcgtcgaaa agcaccaacc ggatgtgatt ggcctgcagg agacaaaagt tcatgacgat    120
atgtttccgc tcgaagaggt ggcgaagctc ggctacaacg tgttttatca cgggcagaaa    180
ggccattatg gcgtggcgct gctgaccaaa gagacgccga ttgccgtgcg tcgcggcttt    240
cccggtgacg acgaagaggc gcagcggcgg attattatgg cggaaatccc ctcactgctg    300
ggtaatgtca ccgtgatcaa cggttacttc ccgcagggtg aaagccgcga ccatccgata    360
aaattcccgg caaaagcgca gttttatcag aatctgcaaa actacctgga accgaactc    420 aaacgtgata tccggtact gattatgggc gatatgaata tcagccctac agatctggat    480
atcggcattg cgaagaaaa ccgtaagcgc tggctgcgta ccggtaaatg ctctttcctg    540
ccggaagagc gcgaatggat ggacaggctg atgagctggg ggttggtcga taccttccgc    600
catgcgaatc cgcaaacagc agatcgtttc tcatggtttg attaccgctc aaaaggtttt    660
gacgataacc gtggtctgcg catcgacctg ctgctcgcca gccaaccgct ggcagaatgt    720
tgcgtagaaa ccggcatcga ctatgaaatc cgcagcatgg aaaaaccgtc cgatcacgcc    780
cccgtctggg cgaccttccg ccgc                                          804

<210> SEQ ID NO 13
<211> LENGTH: 268
<212> TYPE: PRT

<213> ORGANISM: Escherichia coli

<400> SEQUENCE: 13

```
Met Lys Phe Val Ser Phe Asn Ile Asn Gly Leu Arg Ala Arg Pro His
1               5                   10                  15
Gln Leu Glu Ala Ile Val Glu Lys His Gln Pro Asp Val Ile Gly Leu
            20                  25                  30
Gln Glu Thr Lys Val His Asp Asp Met Phe Pro Leu Glu Glu Val Ala
        35                  40                  45
Lys Leu Gly Tyr Asn Val Phe Tyr His Gly Gln Lys Gly His Tyr Gly
    50                  55                  60
Val Ala Leu Leu Thr Lys Glu Thr Pro Ile Ala Val Arg Arg Gly Phe
65                  70                  75                  80
Pro Gly Asp Asp Glu Glu Ala Gln Arg Arg Ile Ile Met Ala Glu Ile
                85                  90                  95
Pro Ser Leu Leu Gly Asn Val Thr Val Ile Asn Gly Tyr Phe Pro Gln
            100                 105                 110
Gly Glu Ser Arg Asp His Pro Ile Lys Phe Pro Ala Lys Ala Gln Phe
        115                 120                 125
Tyr Gln Asn Leu Gln Asn Tyr Leu Glu Thr Glu Leu Lys Arg Asp Asn
    130                 135                 140
Pro Val Leu Ile Met Gly Asp Met Asn Ile Ser Pro Thr Asp Leu Asp
145                 150                 155                 160
Ile Gly Ile Gly Glu Glu Asn Arg Lys Arg Trp Leu Arg Thr Gly Lys
                165                 170                 175
Cys Ser Phe Leu Pro Glu Glu Arg Glu Trp Met Asp Arg Leu Met Ser
            180                 185                 190
Trp Gly Leu Val Asp Thr Phe Arg His Ala Asn Pro Gln Thr Ala Asp
        195                 200                 205
Arg Phe Ser Trp Phe Asp Tyr Arg Ser Lys Gly Phe Asp Asp Asn Arg
    210                 215                 220
Gly Leu Arg Ile Asp Leu Leu Leu Ala Ser Gln Pro Leu Ala Glu Cys
225                 230                 235                 240
Cys Val Glu Thr Gly Ile Asp Tyr Glu Ile Arg Ser Met Glu Lys Pro
                245                 250                 255
Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120
ggcgactatg atgcggatgg cctgaccggc accgcgatcc tggttcgtgg tctggccgcc    180
ctgggtgcgg atgttcatcc gtttatcccg caccgcctgg aagaaggcta tggtgtcctg    240
atggaacgcg tcccggaaca tctggaagcc tcggacctgt ttctgaccgt tgactgcggc    300
attccaacc atgcggaact gcgcgaactg ctggaaaatg gcgtggaagt cattgttacc    360
gatcatcata cgccgggcaa aacgccgccc cgggtctgg tcgtgcatcc ggcgctgacg    420
ccggatctga agaaaaaacc gaccggcgca ggcgtggcgt ttctgctgct gtgggcactg    480
```

-continued

```
catgaacgcc tgggcctgcc gccgccgctg aatacgcgg acctggcagc cgttggcacc      540
attgccgacg ttgccccgct gtggggttgg aatcgtgcac tggtgaaaga aggtctggca      600
cgcatcccgg cttcatcttg ggtgggcctg cgtctgctgg ctgaagccgt gggctatacc      660
ggcaaagcgg tcgaagtcgc tttccgcatc gcgccgcgca tcaatgcggc ttcccgcctg      720
ggcgaagcgg aaaaagccct gcgcctgctg ctgacggatg atgcggcaga agctcaggcg      780
ctggtcggcg aactgcaccg tctgaacgcc gtcgtcaga ccctggaaga agcgatgctg       840
cgcaaactgc tgccgcaggc cgacccggaa gcgaaagcca tcgttctgct ggacccggaa      900
ggccatccgg tgttatggg tattgtggcc tctcgcatcc tggaagcgac cctgcgcccg       960
gtctttctgg tgcccaggg caaaggcacc gtgcgttcgc tggctccgat ttccgccgtc      1020
gaagcactgc gcagcgcgga agatctgctg ctgcgttatg gtggtcataa agaagcggcg     1080
ggtttcgcaa tggatgaagc gctgtttccg gcgttcaaag cacgcgttga agcgtatgcc     1140
gcacgtttcc cggatccggt tcgtgaagtg gcactgctgg atctgctgcc ggaaccgggc     1200
ctgctgccgc aggtgttccg tgaactggca ctgctggaac cgtatggtga aggtaacccg     1260
gaaccgctgt tcctg                                                      1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220
```

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg gaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420
aaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
tactttgcca actatgaccc gcgtatgaag cgtgaaggcc tgcattatgt cgtgattgag     600
cgggatgaaa agtacatggc gagttttgac gagatcgtgc ggagttcat cgaaaaaatg     660 gacgaggcac tggctgaaat tggttttgta tttggggagc aatggcgatc tggctctggt     720
tccggcagcg gttccgga                                                  738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

-continued

```
Arg Asn Gly Thr Ser Trp Met Asp Glu Ile Thr Thr Val Val Asp
130                 135                 140
Glu Ile His Leu Leu Asp Ser Lys Asn Arg Gly Pro Thr Leu Glu Val
145                 150                 155                 160
Thr Ile Thr Lys Leu Met Arg Leu Asn Pro Asp Val Gln Val Val Ala
                165                 170                 175
Leu Ser Ala Thr Val Gly Asn Ala Arg Glu Met Ala Asp Trp Leu Gly
            180                 185                 190
Ala Ala Leu Val Leu Ser Glu Trp Arg Pro Thr Asp Leu His Glu Gly
        195                 200                 205
Val Leu Phe Gly Asp Ala Ile Asn Phe Pro Gly Ser Gln Lys Lys Ile
210                 215                 220
Asp Arg Leu Glu Lys Asp Asp Ala Val Asn Leu Val Leu Asp Thr Ile
225                 230                 235                 240
Lys Ala Glu Gly Gln Cys Leu Val Phe Glu Ser Ser Arg Arg Asn Cys
                245                 250                 255
Ala Gly Phe Ala Lys Thr Ala Ser Ser Lys Val Ala Lys Ile Leu Asp
            260                 265                 270
Asn Asp Ile Met Ile Lys Leu Ala Gly Ile Ala Glu Glu Val Glu Ser
        275                 280                 285
Thr Gly Glu Thr Asp Thr Ala Ile Val Leu Ala Asn Cys Ile Arg Lys
290                 295                 300
Gly Val Ala Phe His His Ala Gly Leu Asn Ser Asn His Arg Lys Leu
305                 310                 315                 320
Val Glu Asn Gly Phe Arg Gln Asn Leu Ile Lys Val Ile Ser Ser Thr
                325                 330                 335
Pro Thr Leu Ala Ala Gly Leu Asn Leu Pro Ala Arg Arg Val Ile Ile
            340                 345                 350
Arg Ser Tyr Arg Arg Phe Asp Ser Asn Phe Gly Met Gln Pro Ile Pro
        355                 360                 365
Val Leu Glu Tyr Lys Gln Met Ala Gly Arg Ala Gly Arg Pro His Leu
370                 375                 380
Asp Pro Tyr Gly Glu Ser Val Leu Leu Ala Lys Thr Tyr Asp Glu Phe
385                 390                 395                 400
Ala Gln Leu Met Glu Asn Tyr Val Glu Ala Asp Ala Glu Asp Ile Trp
                405                 410                 415
Ser Lys Leu Gly Thr Glu Asn Ala Leu Arg Thr His Val Leu Ser Thr
            420                 425                 430
Ile Val Asn Gly Phe Ala Ser Thr Arg Gln Glu Leu Phe Asp Phe Phe
        435                 440                 445
Gly Ala Thr Phe Phe Ala Tyr Gln Gln Asp Lys Trp Met Leu Glu Glu
450                 455                 460
Val Ile Asn Asp Cys Leu Glu Phe Leu Ile Asp Lys Ala Met Val Ser
465                 470                 475                 480
Glu Thr Glu Asp Ile Glu Asp Ala Ser Lys Leu Phe Leu Arg Gly Thr
                485                 490                 495
Arg Leu Gly Ser Leu Val Ser Met Leu Tyr Ile Asp Pro Leu Ser Gly
            500                 505                 510
Ser Lys Ile Val Asp Gly Phe Lys Asp Ile Gly Lys Ser Thr Gly Gly
        515                 520                 525
Asn Met Gly Ser Leu Glu Asp Asp Lys Gly Asp Asp Ile Thr Val Thr
530                 535                 540
```

```
Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
                660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160
```

```
Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575
```

```
Gly Leu Leu Ala Leu His Arg Trp Ile Gly Ser Pro Glu Ala Lys
            580                 585                 590

Leu Ala Glu Asp Leu Lys Phe Glu Ser Gly Asp Val His Arg Met Val
            595                 600                 605

Glu Ser Ser Gly Trp Leu Leu Arg Cys Ile Trp Glu Ile Ser Lys His
        610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
            675                 680                 685

Glu Gly Ile Gly Ala Thr Leu Ala Asn Asn Ile Lys Ser Gln Leu Arg
            690                 695                 700

Lys Gly Gly
705

<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65              70                  75                  80

Ala Glu Glu Lys Tyr Arg Glu Phe Lys Glu Trp Lys Leu Gly Leu
            85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240
```

```
Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Glu Leu Ala Asp Trp Leu
    595                 600                 605

Met Tyr Ser Leu Ile Glu Leu Tyr Lys Leu Phe Glu Pro Lys Glu Glu
        610                 615                 620

Ile Leu Asn Tyr Leu Arg Asp Leu His Leu Arg Leu Arg His Gly Val
625                 630                 635                 640

Arg Glu Glu Leu Leu Gly Leu Val Arg Leu Pro Asn Ile Gly Arg Lys
                645                 650                 655
```

```
Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
    195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
    275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320
```

-continued

Gly Tyr Ile Glu Val Ile Ala Ala Thr Pro Thr Leu Ala Ala Gly Leu
              325                 330                 335

Asn Leu Pro Ala Arg Arg Val Ile Ile Arg Asp Tyr Asn Arg Phe Ala
              340                 345                 350

Ser Gly Leu Gly Met Val Pro Ile Pro Val Gly Glu Tyr His Gln Met
              355                 360                 365

Ala Gly Arg Ala Gly Arg Pro His Leu Asp Pro Tyr Gly Glu Ala Val
        370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
                420                 425                 430

Asp Gln Glu Ala Leu Ser Ser Phe Met Glu Arg Thr Phe Tyr Phe Phe
            435                 440                 445

Gln His Pro Lys Thr Arg Ser Leu Pro Arg Leu Val Ala Asp Ala Ile
        450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
                500                 505                 510

Thr Leu Ile Gly Leu Leu His Val Ile Cys Val Ser Pro Asp Met Gln
            515                 520                 525

Arg Leu Tyr Leu Lys Ala Ala Asp Thr Gln Leu Leu Arg Thr Phe Leu
        530                 535                 540

Phe Lys His Lys Asp Asp Leu Ile Leu Pro Leu Pro Phe Gly Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
        690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
            725                 730                 735

```
Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
            755                 760                 765

Ser Glu Lys Glu Asn Ser Ser Ser Asp Lys Thr Glu Glu Ile Pro Asp
        770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320
```

-continued

```
Thr Gln Ala Ile Ala Gly Leu Ser Glu Arg Lys Val Gln Phe Thr Tyr
                325                 330                 335
Thr Asp Val Leu Ala Arg Thr Val Gly Ile Leu Pro Pro Glu Asn Gly
            340                 345                 350
Val Ile Glu Arg Ala Arg Ala Gly Ile Asp Glu Ala Ile Ser Arg Glu
        355                 360                 365
Gln Leu Ile Pro Leu Asp Arg Glu Lys Gly Leu Phe Thr Ser Gly Ile
    370                 375                 380
His Val Leu Asp Glu Leu Ser Val Arg Ala Leu Ser Arg Asp Ile Met
385                 390                 395                 400
Lys Gln Asn Arg Val Thr Val His Pro Glu Lys Ser Val Pro Arg Thr
                405                 410                 415
Ala Gly Tyr Ser Asp Ala Val Ser Val Leu Ala Gln Asp Arg Pro Ser
            420                 425                 430
Leu Ala Ile Val Ser Gly Gln Gly Ala Ala Gly Gln Arg Glu Arg
        435                 440                 445
Val Ala Glu Leu Val Met Met Ala Arg Glu Gln Gly Arg Glu Val Gln
    450                 455                 460
Ile Ile Ala Ala Asp Arg Arg Ser Gln Met Asn Leu Lys Gln Asp Glu
465                 470                 475                 480
Arg Leu Ser Gly Glu Leu Ile Thr Gly Arg Arg Gln Leu Leu Glu Gly
                485                 490                 495
Met Ala Phe Thr Pro Gly Ser Thr Val Ile Val Asp Gln Gly Glu Lys
            500                 505                 510
Leu Ser Leu Lys Glu Thr Leu Thr Leu Leu Asp Gly Ala Ala Arg His
        515                 520                 525
Asn Val Gln Val Leu Ile Thr Asp Ser Gly Gln Arg Thr Gly Thr Gly
    530                 535                 540
Ser Ala Leu Met Ala Met Lys Asp Ala Gly Val Asn Thr Tyr Arg Trp
545                 550                 555                 560
Gln Gly Gly Glu Gln Arg Pro Ala Thr Ile Ile Ser Glu Pro Asp Arg
                565                 570                 575
Asn Val Arg Tyr Ala Arg Leu Ala Gly Asp Phe Ala Ala Ser Val Lys
            580                 585                 590
Ala Gly Glu Glu Ser Val Ala Gln Val Ser Gly Val Arg Glu Gln Ala
        595                 600                 605
Ile Leu Thr Gln Ala Ile Arg Ser Glu Leu Lys Thr Gln Gly Val Leu
    610                 615                 620
Gly His Pro Glu Val Thr Met Thr Ala Leu Ser Pro Val Trp Leu Asp
625                 630                 635                 640
Ser Arg Ser Arg Tyr Leu Arg Asp Met Tyr Arg Pro Gly Met Val Met
                645                 650                 655
Glu Gln Trp Asn Pro Glu Thr Arg Ser His Asp Arg Tyr Val Ile Asp
            660                 665                 670
Arg Val Thr Ala Gln Ser His Ser Leu Thr Leu Arg Asp Ala Gln Gly
        675                 680                 685
Glu Thr Gln Val Val Arg Ile Ser Ser Leu Asp Ser Ser Trp Ser Leu
    690                 695                 700
Phe Arg Pro Glu Lys Met Pro Val Ala Asp Gly Glu Arg Leu Arg Val
705                 710                 715                 720
Thr Gly Lys Ile Pro Gly Leu Arg Val Ser Gly Gly Asp Arg Leu Gln
                725                 730                 735
```

```
Val Ala Ser Val Ser Glu Asp Ala Met Thr Val Val Pro Gly Arg
                740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
                820                 825                 830

Phe Thr Val Val Ser Glu Gln Ile Lys Ala Arg Ala Gly Glu Thr Leu
                835                 840                 845

Leu Glu Thr Ala Ile Ser Leu Gln Lys Ala Gly Leu His Thr Pro Ala
850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
                900                 905                 910

Lys Arg Gly Asp Leu Leu Tyr Val Asp Val Ala Lys Gly Tyr Gly Thr
                915                 920                 925

Gly Leu Leu Val Ser Arg Ala Ser Tyr Glu Ala Glu Lys Ser Ile Leu
                930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
                980                 985                 990

Tyr Ala Gly Val Gly Lys Thr Thr  Gln Phe Arg Ala Val  Met Ser Ala
                995                 1000                1005

Val Asn Met Leu Pro Ala Ser  Glu Arg Pro Arg Val  Val Gly Leu
    1010                    1015                    1020

Gly Pro Thr His Arg Ala Val  Gly Glu Met Arg Ser  Ala Gly Val
    1025                    1030                    1035

Asp Ala Gln Thr Leu Ala Ser  Phe Leu His Asp Thr  Gln Leu Gln
    1040                    1045                    1050

Gln Arg Ser Gly Glu Thr Pro  Asp Phe Ser Asn Thr  Leu Phe Leu
    1055                    1060                    1065

Leu Asp Glu Ser Ser Met Val  Gly Asn Thr Glu Met  Ala Arg Ala
    1070                    1075                    1080

Tyr Ala Leu Ile Ala Ala Gly  Gly Gly Arg Ala Val  Ala Ser Gly
    1085                    1090                    1095

Asp Thr Asp Gln Leu Gln Ala  Ile Ala Pro Gly Gln  Ser Phe Arg
    1100                    1105                    1110

Leu Gln Gln Thr Arg Ser Ala  Ala Asp Val Val Ile  Met Lys Glu
    1115                    1120                    1125

Ile Val Arg Gln Thr Pro Glu  Leu Arg Glu Ala Val  Tyr Ser Leu
    1130                    1135                    1140
```

```
Ile Asn Arg Asp Val Glu Arg Ala Leu Ser Gly Leu Glu Ser Val
1145                1150                1155

Lys Pro Ser Gln Val Pro Arg Leu Glu Gly Ala Trp Ala Pro Glu
1160                1165                1170

His Ser Val Thr Glu Phe Ser His Ser Gln Glu Ala Lys Leu Ala
1175                1180                1185

Glu Ala Gln Gln Lys Ala Met Leu Lys Gly Glu Ala Phe Pro Asp
1190                1195                1200

Ile Pro Met Thr Leu Tyr Glu Ala Ile Val Arg Asp Tyr Thr Gly
1205                1210                1215

Arg Thr Pro Glu Ala Arg Glu Gln Thr Leu Ile Val Thr His Leu
1220                1225                1230

Asn Glu Asp Arg Arg Val Leu Asn Ser Met Ile His Asp Ala Arg
1235                1240                1245

Glu Lys Ala Gly Glu Leu Gly Lys Glu Gln Val Met Val Pro Val
1250                1255                1260

Leu Asn Thr Ala Asn Ile Arg Asp Gly Glu Leu Arg Arg Leu Ser
1265                1270                1275

Thr Trp Glu Lys Asn Pro Asp Ala Leu Ala Leu Val Asp Asn Val
1280                1285                1290

Tyr His Arg Ile Ala Gly Ile Ser Lys Asp Asp Gly Leu Ile Thr
1295                1300                1305

Leu Gln Asp Ala Glu Gly Asn Thr Arg Leu Ile Ser Pro Arg Glu
1310                1315                1320

Ala Val Ala Glu Gly Val Thr Leu Tyr Thr Pro Asp Lys Ile Arg
1325                1330                1335

Val Gly Thr Gly Asp Arg Met Arg Phe Thr Lys Ser Asp Arg Glu
1340                1345                1350

Arg Gly Tyr Val Ala Asn Ser Val Trp Thr Val Thr Ala Val Ser
1355                1360                1365

Gly Asp Ser Val Thr Leu Ser Asp Gly Gln Gln Thr Arg Val Ile
1370                1375                1380

Arg Pro Gly Gln Glu Arg Ala Glu Gln His Ile Asp Leu Ala Tyr
1385                1390                1395

Ala Ile Thr Ala His Gly Ala Gln Gly Ala Ser Glu Thr Phe Ala
1400                1405                1410

Ile Ala Leu Glu Gly Thr Glu Gly Asn Arg Lys Leu Met Ala Gly
1415                1420                1425

Phe Glu Ser Ala Tyr Val Ala Leu Ser Arg Met Lys Gln His Val
1430                1435                1440

Gln Val Tyr Thr Asp Asn Arg Gln Gly Trp Thr Asp Ala Ile Asn
1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530
```

```
Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile
1655                1660                1665

Val Arg Lys Met Ala Glu Asn Lys Pro Asp Leu Pro Asp Gly Lys
1670                1675                1680

Thr Glu Leu Ala Val Arg Asp Ile Ala Gly Gln Glu Arg Asp Arg
1685                1690                1695

Ser Ala Ile Ser Glu Arg Glu Thr Ala Leu Pro Glu Ser Val Leu
1700                1705                1710

Arg Glu Ser Gln Arg Glu Arg Glu Ala Val Arg Glu Val Ala Arg
1715                1720                1725

Glu Asn Leu Leu Gln Glu Arg Leu Gln Gln Met Glu Arg Asp Met
1730                1735                1740

Val Arg Asp Leu Gln Lys Glu Lys Thr Leu Gly Gly Asp
1745                1750                1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140
```

```
Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
            165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
        210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
            245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
        290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
            325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
        370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
            405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
        450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
            485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
        530                 535                 540

Phe Glu Ala Lys Arg Tyr Tyr Ser Lys Ile Glu Pro Leu Val Asn Val
545                 550                 555                 560
```

```
Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 24
<211> LENGTH: 50
<212> TYPE: DNA
<213> ORGANISM: Artificial Sequence
<220> FEATURE:
<223> OTHER INFORMATION: double stranded portion of a MuA substrate of
      the invention

<400> SEQUENCE: 24
gttttcgcat ttatcgtgaa acgctttcgc gtttttcgtg cgccgcttca          50

<210> SEQ ID NO 25
<211> LENGTH: 50
<212> TYPE: DNA
<213> ORGANISM: Artificial Sequence
<220> FEATURE:
<223> OTHER INFORMATION: double stranded portion of a MuA substrate of
      the invention
<220> FEATURE:
<221> NAME/KEY: misc_feature
<222> LOCATION: (1)..(1)
<223> OTHER INFORMATION: n is uridine

<400> SEQUENCE: 25
ngaagcggcg cacgaaaaac gcgaaagcgt tcacgataa atgcgaaaac          50

<210> SEQ ID NO 26
<211> LENGTH: 54
<212> TYPE: DNA
<213> ORGANISM: Artificial Sequence
<220> FEATURE:
<223> OTHER INFORMATION: overhang strand of the double stranded MuA
      substrate of the invention
<220> FEATURE:
<221> NAME/KEY: misc_feature
<222> LOCATION: (5)..(5)
<223> OTHER INFORMATION: n is uridine

<400> SEQUENCE: 26
gatcngaagc ggcgcacgaa aaacgcgaaa gcgtttcacg ataaatgcga aaac     54
```

<210> SEQ ID NO 27
<211> LENGTH: 77
<212> TYPE: DNA
<213> ORGANISM: Artificial Sequence
<220> FEATURE:
<223> OTHER INFORMATION: sequence used in example 1

<400> SEQUENCE: 27

```
tttttttttt tttttttttt tttttttttt tttttttttt tttttttttt ggttgtttct    60
gttggtgctg atattgc                                                   77
```

<210> SEQ ID NO 28
<211> LENGTH: 54
<212> TYPE: DNA
<213> ORGANISM: Artificial Sequence
<220> FEATURE:
<223> OTHER INFORMATION: sequence used in Example 1

<400> SEQUENCE: 28

```
gatctgaagc ggcgcacgaa aaacgcgaaa gcgtttcacg ataaatgcga aaac          54
```

<210> SEQ ID NO 29
<211> LENGTH: 48502
<212> TYPE: DNA
<213> ORGANISM: Enterobacteria phage lambda

<400> SEQUENCE: 29

```
gggcggcgac ctcgcgggtt ttcgctattt atgaaaattt tccggtttaa ggcgtttccg      60
ttcttcttcg tcataactta atgtttttat ttaaaatacc ctctgaaaag aaaggaaacg     120
acaggtgctg aaagcgaggc ttttttggcct ctgtcgtttc cttctctgt ttttgtccgt     180
ggaatgaaca atggaagtca acaaaaagca gctggctgac attttcggtg cgagtatccg     240
taccattcag aactggcagg aacagggaat gcccgttctg cgaggcggtg caagggtaa      300
tgaggtgctt tatgactctg ccgccgtcat aaaatggtat gccgaaaggg atgctgaaat     360
tgagaacgaa aagctgcgcc gggaggttga agaactgcgg caggccagcg aggcagatct     420
ccagccagga actattgagt acgaacgcca tcgacttacg cgtgcgcagg ccgacgcaca     480
ggaactgaag aatgccagag actccgctga agtggtggaa accgcattct gtactttcgt     540
gctgtcgcgg atcgcaggtg aaattgccag tattctcgac gggctccccc tgtcggtgca     600
gcggcgtttt ccggaactgg aaaaccgaca tgttgatttc ctgaaacggg atatcatcaa     660
agccatgaac aaaagcagccg cgctggatga actgataccg gggttgctga gtgaatatat     720
cgaacagtca ggttaacagg ctgcggcatt ttgtccgcgc cgggcttcgc tcactgttca     780
ggccggagcc acagaccgcc gttgaatggg cggatgctaa ttactatctc ccgaaagaat     840
ccgcatacca ggaagggcgc tgggaaacac tgcccttca gcgggccatc atgaatgcga     900
tgggcagcga ctacatccgt gaggtgaatg tggtgaagtc tgcccgtgtc ggttattcca     960
aaatgctgct gggtgtttat gcctacttta tagagcataa gcagcgcaac acccttatct    1020
ggttgccgac ggatggtgat gccgagaact ttatgaaaac ccacgttgag ccgactattc    1080
gtgatattcc gtcgctgctg gcgctggccc cgtggtatgg caaaaagcac cgggataaca    1140
cgctcaccat gaagcgtttc actaatgggc gtggcttctg gtgcctgggc ggtaaagcgg    1200
caaaaaacta ccgtgaaaag tcggtggatg tggcgggtta tgatgaactt gctgcttttg    1260
atgatgatat tgaacaggaa ggctctccga cgttcctggg tgacaagcgt attgaaggct    1320
```

-continued

```
cggtctggcc aaagtccatc cgtggctcca cgccaaaagt gagaggcacc tgtcagattg      1380
agcgtgcagc cagtgaatcc ccgcattta tgcgttttca tgttgcctgc ccgcattgcg       1440
gggaggagca gtatcttaaa tttggcgaca aagagacgcc gtttggcctc aaatggacgc      1500
cggatgaccc ctccagcgtg ttttatctct gcgagcataa tgcctgcgtc atccgccagc     1560
aggagctgga ctttactgat gcccgttata tctgcgaaaa gaccgggatc tggacccgtg     1620
atggcattct ctggttttcg tcatccggtg aagagattga gccacctgac agtgtgacct     1680
ttcacatctg gacagcgtac agcccgttca ccacctgggt gcagattgtc aaagactgga     1740
tgaaaacgaa aggggatacg ggaaaacgta aaccttcgt aaacaccacg ctcggtgaga      1800
cgtgggaggc gaaaattggc gaacgtccgg atgctgaagt gatggcagag cggaaagagc     1860
attattcagc gcccgttcct gaccgtgtgg cttacctgac cgccggtatc gactcccagc     1920
tggaccgcta cgaaatgcgc gtatggggat ggggccggg tgaggaaagc tggctgattg      1980
accggcagat tattatgggc cgccacgacg atgaacagac gctgctgcgt gtggatgagg     2040
ccatcaataa aacctatacc cgccggaatg gtgcagaaat gtcgatatcc cgtatctgct     2100
gggatactgg cgggattgac ccgaccattg tgtatgaacg ctcgaaaaaa catgggctgt     2160
tccgggtgat cccattaaa ggggcatccg tctacgaaaa gccggtggcc agcatgccac     2220
gtaagcgaaa caaaacgggg gtttaccta ccgaaatcgg tacgatacc gcgaaagagc       2280
agatttataa ccgcttcaca ctgacgccgg aaggggatga accgcttccc ggtgccgttc     2340
acttcccgaa taacccggat attttgatc tgaccgaagc gcagcagctg actgctgaag       2400
agcaggtcga aaatgggtg gatggcagga aaaaatact gtgggacagc aaaaagcgac       2460
gcaatgaggc actcgactgc ttcgtttatg cgctggcggc gctgcgcatc agtatttccc     2520
gctggcagct ggatctcagt gcgctgctgg cgagcctgca ggaagaggat ggtgcagcaa     2580
ccaacaagaa aacactggca gattacgccc gtgccttatc cggagaggat gaatgacgcg     2640
acaggaagaa cttgccgctg cccgtgcggc actgcatgac ctgatgacag gtaaacgggt     2700
ggcaacagta cagaaagacg gacgaagggt ggagtttacg gccacttccg tgtctgacct     2760
gaaaaaatat attgcagagc tggaagtgca gaccggcatg acacagcgac gcaggggacc     2820
tgcaggattt tatgtatgaa aacgcccacc attcccaccc ttctggggcc ggacggcatg     2880
acatcgctgc gcgaatatgc cggttatcac ggcggtggca gcggatttgg agggcagttg     2940
cggtcgtgga acccaccgag tgaaagtgtg gatgcagccc tgttgcccaa ctttacccgt     3000
ggcaatgccc gcgcagacga tctggtacgc aataacggct atgccgccaa cgccatccag     3060
ctgcatcagg atcatatcgt cgggtctttt ttccggctca gtcatcgccc aagctggcgc     3120
tatctgggca tcggggagga agaagcccgt gccttttccc gcgaggttga agcggcatgg     3180
aaagagtttg ccgaggatga ctgctgctgc attgacgttg agcgaaaacg cacgtttacc     3240
atgatgattc gggaaggtgt ggccatgcac gcctttaacg tgaactgtt cgttcaggcc     3300
acctgggata ccagttcgtc gcggcttttc cggacacagt tccggatggt cagcccgaag     3360
cgcatcagca acccgaacaa taccggcgac agccggaact gccgtgccgg tgtgcagatt     3420
aatgacagcg gtgcggcgct gggatattac gtcagcgagg acgggtatcc tggctggatg     3480
ccgcagaaat ggacatggat accccgtgag ttacccggcg ggcgcgcctc gttcattcac     3540
gttttttgaac ccgtggagga cgggcagact cgcggtgcaa atgtgtttta cagcgtgatg     3600
gagcagatga agatgctcga cacgctgcag aacacgcagc tgcagagcgc cattgtgaag     3660
gcgatgtatg ccgccaccat tgagagtgag ctggatacgc agtcagcgat ggatttatt     3720
```

```
ctgggcgcga acagtcagga gcagcgggaa aggctgaccg gctggattgg tgaaattgcc    3780
gcgtattacg ccgcagcgcc ggtccggctg ggaggcgcaa aagtaccgca cctgatgccg    3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020
tttatggggc ggcgaaaatt cgtcgcatcc cgtcaggcga ccagatgtt tctgtgctgg    4080
ctggaagagg ccatcgttcg ccgcgtggtg acgttacctt caaaagcgcg cttcagtttt    4140
caggaagccc gcagtgcctg ggggaactgc gactggatag gctccggtcg tatggccatc    4200
gatggtctga agaagttca ggaagcggtg atgctgatag aagccggact gagtacctac    4260
gagaaagagt gcgcaaaacg cggtgacgac tatcaggaaa ttttttgccca gcaggtccgt    4320
gaaacgatgg agcgccgtgc agccggtctt aaaccgcccg cctgggcggc tgcagcattt    4380
gaatccgggc tgcgacaatc aacagaggag gagaagagtg acagcagagc tgcgtaatct    4440
cccgcatatt gccagcatgg cctttaatga ccgctgatg cttgaacccg cctatgcgcg    4500
ggttttcttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg gcattctgct    4800
cgatatggac acgcccggcg ggatggtggc gggggcattt gactgcgctg acatcatcgc    4860
ccgtgtgcgt gacataaaac cggtatgggc gcttgccaac gacatgaact gcagtgcagg    4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
aatcacgctg atttacagcg gcagccataa ggtggatggc aaccccctaca gccatcttcc    5100
ggatgacgtc cgggagacac tgcagtcccg gatggacgca accgccaga tgtttgcgca    5160
gaaggtgtcg gcatataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atgggatcc tcaactgtga    5520
ggaggctcac ggacgcgaag aacaggcacg cgtgctggca gaaaccccg gtatgaccgt    5580
gaaaacggcc cgccgcattc tggccgcagc accacagagt gcacaggcgc gcagtgacac    5640
tgcgctggat cgtctgatgc aggggcacc ggcaccgctg gctgcaggta acccggcatc    5700
tgatgccgtt aacgatttgc tgaacacacc agtgtaaggg atgtttatga cgagcaaaga    5760
aacctttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg gcaccaccga cggtgctgcc gttggcattc ttgcggttgc    5940
tgctgaccag accagcacca cgctgacgtt ctacaagtcc ggcacgttcc gttatgagga    6000
tgtgctctgg ccggaggctg ccagcgacga gacgaaaaaa cggaccgcgt ttgccggaac    6060
```

```
ggcaatcagc atcgtttaac tttacccttc atcactaaag gccgcctgtg cggcttttt     6120
tacgggattt ttttatgtcg atgtacacaa ccgcccaact gctggcggca aatgagcaga    6180
aatttaagtt tgatccgctg tttctgcgtc tcttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga gagctggcc attgctcagg tcgaagagat gcaggcagtt tctgccgtgc     6540
ttaagggcaa atacaccatg accggtgaag ccttcgatcc ggttgaggtg gatatgggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
agaagctgga tacccgtcgt ggctctaatt ccgagctgga gacagcggtg aaagacctgg    6840
gcaaagcggt gtcctataag gggatgtatg gcgatgtggc catcgtcgtg tattccggac    6900
agtacgtgga aaacggcgtc aaaaagaact tcctgccgga caacacgatg gtgctgggga    6960
acactcaggc acgcggtctg cgcacctatg gctgcattca ggatgcggac gcacagcgcg    7020
aaggcattaa cgcctctgcc cgttacccga aaaactgggt gaccaccggc gatccggcgc    7080
gtgagttcac catgattcag tcagcaccgc tgatgctgct ggctgaccct gatgagttcg    7140
tgtccgtaca actggcgtaa tcatggccct tcggggccat tgtttctctg tggaggagtc    7200
catgacgaaa gatgaactga ttgcccgtct ccgctcgctg ggtgaacaac tgaaccgtga    7260
tgtcagcctg acggggacga agaagaact ggcgctccgt gtggcagagc tgaaagagga    7320
gcttgatgac acggatgaaa ctgccggtca ggacacccct ctcagccggg aaaatgtgct    7380
gaccggacat gaaaatgagg tgggatcagc gcagccggat accgtgattc tggatacgtc    7440
tgaactggtc acggtcgtgg cactggtgaa gctgcatact gatgcacttc acgccacgcg    7500
ggatgaacct gtggcatttg tgctgccggg aacggcgttt cgtgtctctg ccggtgtggc    7560
agccgaaatg acagagcgcg gcctggccag aatgcaataa cgggaggcgc tgtggctgat    7620
ttcgataacc tgttcgatgc tgccattgcc cgcgccgatg aaacgatacg cgggtacatg    7680
ggaacgtcag ccaccattac atccggtgag cagtcaggtg cggtgatacg tggtgttttt    7740
gatgaccctg aaaatatcag ctatgccgga cagggcgtgc gcgttgaagg ctccagcccg    7800
tccctgtttg tccggactga tgaggtgcgg cagctgcggc gtggagacac gctgaccatc    7860
ggtgaggaaa atttctgggt agatcgggtt tcgccggatg atggcggaag ttgtcatctc    7920
tggcttggac ggggcgtacc gcctgccgtt aaccgtcgcc gctgaaaggg ggatgtatgg    7980
ccataaaagg tcttgagcag gccgttgaaa acctcagccg tatcagcaaa acggcggtgc    8040
ctggtgccgc cgcaatggcc attaaccgcg ttgcttcatc cgcgatatcg cagtcggcgt    8100
cacaggttgc ccgtgagaca aaggtacgcc ggaaactggt aaaggaaagg gccaggctga    8160
aaagggccac ggtcaaaaat ccgcaggcca gaatcaaagt taaccggggg gatttgcccg    8220
taatcaagct gggtaatgcg cgggttgtcc tttcgcgccg caggcgtcgt aaaaaggggc    8280
agcgttcatc cctgaaaggt ggcggcagcg tgcttgtggt gggtaaccgt cgtattcccg    8340
gcgcgtttat tcagcaactg aaaaatggcc ggtggcatgt catgcagcgt gtggctggga    8400
aaaaccgtta ccccattgat gtggtgaaaa tcccgatggc ggtgccgctg accacggcgt    8460
```

```
ttaaacaaaa tattgagcgg atacggcgtg aacgtcttcc gaaagagctg ggctatgcgc      8520
tgcagcatca actgaggatg gtaataaagc gatgaaacat actgaactcc gtgcagccgt      8580
actggatgca ctggagaagc atgacaccgg ggcgacgttt tttgatggtc gccccgctgt      8640
ttttgatgag gcggattttc cggcagttgc cgtttatctc accggcgctg aatacacggg      8700
cgaagagctg gacagcgata cctggcaggc ggagctgcat atcgaagttt cctgcctgc       8760 tcaggtgccg gattcagagc tggatgcgtg gatggagtcc cggatttatc cggtgatgag      8820
cgatatcccg gcactgtcag atttgatcac cagtatggtg ccagcggct atgactaccg       8880 gcgcgacgat gatgcgggct tgtggagttc agccgatctg acttatgtca ttacctatga      8940
aatgtgagga cgctatgcct gtaccaaatc ctacaatgcc ggtgaaaggt gccgggacca      9000
ccctgtgggt ttataagggg agcggtgacc cttacgcgaa tccgcttca gacgttgact       9060 ggtcgcgtct ggcaaaagtt aaagacctga cgcccggcga actgaccgct gagtcctatg      9120
acgacagcta tctcgatgat gaagatgcag actggactgc gaccgggcag ggcagaaat       9180 ctgccggaga taccagcttc acgctggcgt ggatgcccgg agagcagggg cagcaggcgc      9240
tgctggcgtg gtttaatgaa ggcgataccc gtgcctataa aatccgcttc ccgaacggca      9300
cggtcgatgt gttccgtggc tgggtcagca gtatcggtaa ggcggtgacg gcgaaggaag      9360
tgatcacccg cacggtgaaa gtcaccaatg tgggacgtcc gtcgatggca gaagatcgca      9420
gcacggtaac agcggcaacc ggcatgaccg tgacgcctgc cagcacctcg gtggtgaaag      9480
ggcagagcac cacgctgacc gtggccttcc agccggaggg cgtaaccgac aagagctttc      9540
gtgcggtgtc tgcggataaa acaaaagcca ccgtgtcggt cagtggtatg accatcaccg      9600 tgaacgcgt tgctgcaggc aaggtcaaca ttccggttgt atccggtaat ggtgagtttg       9660
ctgcggttgc agaaattacc gtcaccgcca gttaatccgg agagtcagcg atgttcctga      9720
aaaccgaatc atttgaacat aacggtgtga ccgtcacgct ttctgaactg tcagccctgc      9780
agcgcattga gcatctcgcc ctgatgaaac ggcaggcaga acaggcggag tcagacagca      9840
accggaagtt tactgtggaa gacgccatca gaaccggcgc gtttctggtg gcgatgtccc      9900
tgtggcataa ccatccgcag aagacgcaga tgccgtccat gaatgaagcc gttaaacaga      9960
ttgagcagga agtgcttacc acctggccca cggaggcaat ttctcatgct gaaaacgtgg      10020
tgtaccggct gtctggtatg tatgagtttg tggtgaataa tgcccctgaa cagacagagg      10080
acgccgggcc cgcagagcct gtttctgcgg gaaagtgttc gacggtgagc tgagttttgc      10140
cctgaaactg gcgcgtgaga tggggcgacc cgactggcgt gccatgcttg ccgggatgtc      10200
atccacggag tatgccgact ggcaccgctt ttacagtacc cattattttc atgatgttct      10260
gctggatatg cacttttccg ggctgacgta caccgtgctc agcctgtttt tcagcgatcc      10320
ggatatgcat ccgctggatt tcagtctgct gaaccggcgc gaggctgacg aagagcctga      10380
agatgatgtg ctgatgcaga aagcggcagg gcttgccgga ggtgtccgct ttggcccgga      10440
cgggaatgaa gttatccccg cttccccgga tgtggcggac atgacggagg atgacgtaat      10500
gctgatgaca gtatcagaag ggatcgcagg aggagtccgg tatggctgaa ccggtaggcg      10560
atctggtcgt tgatttgagt ctggatgcgg ccagatttga cgagcagatg ccagagtca       10620 ggcgtcattt ttctggtacg gaaagtgatg cgaaaaaaac agcggcagtc gttgaacagt      10680
cgctgagccg acaggcgctg gctgcacaga aagcggggat ttccgtcggg cagtataaag      10740
ccgccatgcg tatgctgcct gcacagttca ccgacgtggc cacgcagctt gcaggcgggc      10800
```

```
aaagtccgtg gctgatcctg ctgcaacagg gggggcaggt gaaggactcc ttcggcggga   10860
tgatccccat gttcaggggg cttgccggtg cgatcaccct gccgatggtg ggggccacct   10920
cgctggcggt ggcgaccggt gcgctggcgt atgcctggta tcagggcaac tcaaccctgt   10980
ccgatttcaa caaaacgctg gtcctttccg gcaatcaggc gggactgacg gcagatcgta   11040
tgctggtcct gtccagagcc gggcaggcgg cagggctgac gtttaaccag accagcgagt   11100
cactcagcgc actggttaag gcggggtaa gcggtgaggc tcagattgcg tccatcagcc   11160
agagtgtggc gcgtttctcc tctgcatccg gcgtggaggt ggacaaggtc gctgaagcct   11220
tcgggaagct gaccacagac ccgacgtcgg ggctgacggc gatggctcgc cagttccata   11280
acgtgtcggc ggagcagatt gcgtatgttg ctcagttgca gcgttccggc gatgaagccg   11340
gggcattgca ggcggcgaac gaggccgcaa cgaaagggtt tgatgaccag acccgccgcc   11400
tgaaagagaa catgggcacg ctggagacct gggcagacag gactgcgcgg gcattcaaat   11460
ccatgtggga tgcggtgctg gatattggtc gtcctgatac cgcgcaggag atgctgatta   11520
aggcagaggc tgcgtataag aaagcagacg acatctggaa tctgcgcaag gatgattatt   11580
ttgttaacga tgaagcgcgg gcgcgttact gggatgatcg tgaaaaggcc cgtcttgcgc   11640
ttgaagccgc ccgaaagaag gctgagcagc agactcaaca ggacaaaaat gcgcagcagc   11700
agagcgatac cgaagcgtca cggctgaaat ataccgaaga ggcgcagaag gcttacgaac   11760
ggctgcagac gccgctggag aaatataccc ccgtcagga gaactgaac aaggcactga   11820 aagacgggaa aatcctgcag gcggattaca acacgctgat ggcggcggcg aaaaaggatt   11880
atgaagcgac gctgaaaaag ccgaaacagt ccagcgtgaa ggtgtctgcg ggcgatcgtc   11940
aggaagacag tgctcatgct gccctgctga cgcttcaggc agaactccgg acgctggaga   12000
agcatgccgg agcaaatgag aaaatcagcc agcagcgccg ggatttgtgg aaggcggaga   12060
gtcagttcgc ggtactggag gaggcggcgc aacgtcgcca gctgtctgca caggagaaat   12120
ccctgctggc gcataaagat gagacgctgg agtacaaacg ccagctggct gcacttggcg   12180
acaaggttac gtatcaggag cgcctgaacg cgctggcgca gcaggcggat aaattcgcac   12240
agcagcaacg ggcaaaacgg gccgccattg atgcgaaaag ccgggggctg actgaccggc   12300
aggcagaacg ggaagccacg gaacagcgcc tgaaggaaca gtatggcgat aatccgctgg   12360
cgctgaataa cgtcatgtca gagcagaaaa agacctgggc ggctgaagac cagcttcgcg   12420
ggaactggat ggcaggcctg aagtccggct ggagtgagtg ggaagagagc gccacggaca   12480
gtatgtcgca ggtaaaaagt gcagccacgc agacctttga tggtattgca cagaatatgg   12540
cggcgatgct gaccggcagt gagcagaact ggcgcagctt cacccgttcc gtgctgtcca   12600
tgatgacaga aattctgctt aagcaggcaa tggtggggat tgtcgggagt atcggcagcg   12660
ccattggcgg ggctgttggt ggcggcgcat ccgcgtcagg cggtacagcc attcaggccg   12720
ctgcggcgaa attccatttt gcaaccggag gatttacggg aaccggcggc aaatatgagc   12780
cagcggggat tgttcaccgt ggtgagtttg tcttcacgaa ggaggcaacc agccggattg   12840
gcgtggggaa tctttaccgg ctgatgcgcg gctatgccac cggcggttat gtcggtacac   12900
cgggcagcat ggcagacagc cggtcgcagg cgtccggacg gtttgagcag ataaccatg   12960 tggtgattaa caacgacggc acgaacgggc agataggtcc ggctgctctg aaggcggtgt   13020
atgacatggc ccgcaagggt gcccgtgatg aaattcagac acagatgcgt gatggtggcc   13080
tgttctccgg aggtgacga tgaagacctt ccgctgaaa gtgaacccg gtatggatgt   13140 ggcttcggtc ccttctgtaa gaaaggtgcg ctttggtgat ggctattctc agcgagcgcc   13200
```

-continued

```
tgccgggctg aatgccaacc tgaaaacgta cagcgtgacg ctttctgtcc cccgtgagga   13260
ggccacggta ctggagtcgt ttctggaaga gcacggggc tggaaatcct ttctgtggac    13320
gccgccttat gagtggcggc agataaaggt gacctgcgca aaatggtcgt cgcgggtcag   13380
tatgctgcgt gttgagttca gcgcagagtt tgaacaggtg gtgaactgat gcaggatatc   13440
cggcaggaaa cactgaatga atgcacccgt gcggagcagt cggccagcgt ggtgctctgg   13500
gaaatcgacc tgacagaggt cggtggagaa cgttattttt tctgtaatga gcagaacgaa   13560
aaaggtgagc cggtcacctg gcaggggcga cagtatcagc cgtatcccat tcaggggagc   13620
ggttttgaac tgaatggcaa aggcaccagt acgcgcccca cgctgacggt ttctaacctg   13680
tacggtatgg tcaccgggat ggcggaagat atgcagagtc tggtcggcgg aacggtggtc   13740
cggcgtaagg tttacgcccg ttttctggat gcggtgaact tcgtcaacgg aaacagttac   13800
gccgatccgg agcaggaggt gatcagccgc tggcgcattg agcagtgcag cgaactgagc   13860
gcggtgagtg cctcctttgt actgtccacg ccgacggaaa cggatggcgc tgttttttccg   13920 ggacgtatca tgctggccaa cacctgcacc tggacctatc gcggtgacga gtgcggttat   13980
agcggtccgg ctgtcgcgga tgaatatgac cagccaacgt ccgatatcac gaaggataaa   14040
tgcagcaaat gcctgagcgg ttgtaagttc cgcaataacg tcggcaactt tggcggcttc   14100
ctttccatta acaaactttc gcagtaaatc ccatgacaca gacagaatca gcgattctgg   14160
cgcacgcccg gcgatgtgcg ccagcggagt cgtgcggctt cgtggtaagc acgccggagg   14220
gggaaagata tttcccctgc gtgaatatct ccggtgagcc ggaggctatt tccgtatgtc   14280
gccggaagac tggctgcagg cagaaatgca gggtgagatt gtggcgctgg tccacagcca   14340
ccccggtggt ctgccctggc tgagtgaggc cgaccggcgg ctgcaggtgc agagtgattt   14400
gccgtggtgg ctggtctgcc gggggacgat tcataagttc cgctgtgtgc cgcatctcac   14460
cgggcggcgc tttgagcacg gtgtgacgga ctgttacaca ctgttccggg atgcttatca   14520
tctggcgggg attgagatgc cggacttca tcgtgaggat gactggtggc gtaacggcca    14580
gaatctctat ctggataatc tggaggcgac ggggctgtat caggtgccgt tgtcagcggc   14640
acagccgggc gatgtgctgc tgtgctgttt tggttcatca gtgccgaatc acgccgcaat   14700
ttactgcggc gacggcgagc tgctgcacca tattcctgaa caactgagca acgagagag    14760 gtacaccgac aaatggcagc gacgcacaca ctccctctgg cgtcaccggg catggcgcgc   14820
atctgccttt acggggattt acaacgattt ggtcgccgca tcgaccttcg tgtgaaaacg   14880
ggggctgaag ccatccgggc actggccaca cagctcccgg cgtttcgtca gaaactgagc   14940
gacggctggt atcaggtacg gattgccggg cgggacgtca gcacgtccgg gttaacggcg   15000
cagttacatg agactctgcc tgatggcgct gtaattcata ttgttcccag agtcgccggg   15060
gccaagtcag gtggcgtatt ccagattgtc ctgggggctg ccgccattgc cggatcattc   15120
tttaccgccg gagccaccct gcagcatgg ggggcagcca ttggggccgg tggtatgacc    15180
ggcatcctgt tttctctcgg tgccagtatg gtgctcggtg gtgtggcgca gatgctggca   15240
ccgaaagcca gaactccccg tatacagaca acggataacg gtaagcagaa cacctatttc   15300
tcctcactgg ataacatggt tgcccagggc aatgttctgc ctgttctgta cggggaaatg   15360
cgcgtggggt cacgcgtggt ttctcaggag atcagcacgg cagacgaagg ggacggtggt   15420
caggttgtgg tgattggtcg ctgatgcaaa atgtttatg tgaaaccgcc tgcgggcggt    15480
tttgtcattt atggagcgtg aggaatgggt aaaggaagca gtaaggggca taccccgcgc   15540
```

```
gaagcgaagg acaacctgaa gtccacgcag ttgctgagtg tgatcgatgc catcagcgaa   15600
gggccgattg aaggtccggt ggatggctta aaaagcgtgc tgctgaacag tacgccggtg   15660
ctggacactg aggggaatac caacatatcc ggtgtcacgg tggtgttccg ggctggtgag   15720
caggagcaga ctccgccgga gggatttgaa tcctccggct ccgagacggt gctgggtacg   15780
gaagtgaaat atgacacgcc gatcacccgc accattacgt ctgcaaacat cgaccgtctg   15840
cgctttacct tcggtgtaca ggcactggtg gaaaccacct caaagggtga caggaatccg   15900
tcggaagtcc gcctgctggt tcagatacaa cgtaacggtg gctgggtgac ggaaaaagac   15960
atcaccatta agggcaaaac cacctcgcag tatctggcct cggtggtgat gggtaacctg   16020
ccgccgcgcc cgtttaatat ccggatgcgc aggatgacgc cggacagcac cacagaccag   16080
ctgcagaaca aaacgctctg gtcgtcatac actgaaatca tcgatgtgaa acagtgctac   16140
ccgaacacgg cactggtcgg cgtgcaggtg gactcggagc agttcggcag ccagcaggtg   16200
agccgtaatt atcatctgcg cgggcgtatt ctgcaggtgc cgtcgaacta aacccgcag   16260 acgcggcaat acagcggtat ctgggacgga acgtttaaac cggcatacag caacaacatg   16320
gcctggtgtc tgtgggatat gctgacccat ccgcgctacg gcatggggaa acgtcttggt   16380
gcggcggatg tggataaatg ggcgctgtat gtcatcggcc agtactgcga ccagtcagtg   16440
ccggacggct ttggcggcac ggagccgcgc atcacctgta atgcgtacct gaccacacag   16500
cgtaaggcgt gggatgtgct cagcgatttc tgctcggcga tgcgctgtat gccggtatgg   16560
aacgggcaga cgctgacgtt cgtgcaggac cgaccgtcgg ataagacgtg gacctataac   16620
cgcagtaatg tggtgatgcc ggatgatggc gcgccgttcc gctacagctt cagcgccctg   16680
aaggaccgcc ataatgccgt tgaggtgaac tggattgacc cgaacaacgg ctgggagacg   16740
gcgacagagc ttgttgaaga tacgcaggcc attgcccgtt acgtcgtaa tgttacgaag   16800 atggatgcct ttggctgtac cagccggggg caggcacacc gcgccgggct gtggctgatt   16860
aaaacagaac tgctggaaac gcagaccgtg gatttcagcg tcggcgcaga agggcttcgc   16920
catgtaccgg gcgatgttat tgaaatctgc gatgatgact atgccggtat cagcaccggt   16980
ggtcgtgtgc tggcggtgaa cagccagacc cggacgctga cgctcgaccg tgaaatcacg   17040
ctgccatcct ccggtaccgc gctgataagc ctggttgacg gaagtggcaa tccggtcagc   17100
gtggaggttc agtccgtcac cgacggcgtg aaggtaaaag tgagccgtgt tcctgacggt   17160
gttgctgaat acagcgtatg ggagctgaag ctgccgacgc tgcgccagcg actgttccgc   17220
tgcgtgagta tccgtgagaa cgacgacggc acgtatgcca tcaccgccgt gcagcatgtg   17280
ccggaaaaag aggccatcgt ggataacggg gcgcactttg acggcgaaca gagtggcacg   17340
gtgaatggta tcacgccgcc agcggtgcag cacctgaccg cagaagtcac tgcagacagc   17400
ggggaatatc aggtgctggc gcgatgggac acaccgaagg tggtgaaggg cgtgagtttc   17460
ctgctccgtc tgaccgtaac agcggacgac ggcagtgagc ggctggtcag cacggcccgg   17520
acgacggaaa ccacataccg cttcacgcaa ctggcgctgg gaactacag gctgacagtc   17580 cgggcggtaa atgcgtgggg gcagcagggc gatccggcgt cggtatcgtt ccggattgcc   17640
gcaccggcag caccgtcgag gattgagctg acgccgggct attttcagat aaccgccacg   17700
ccgcatcttg ccgtttatga cccgacggta cagtttgagt tctggttctc ggaaaagcag   17760
attgcggata tcagacaggt tgaaaccagc acgcgttatc ttggtacggc gctgtactgg   17820
atagccgcca gtatcaatat caaaccgggc catgattatt actttatatt ccgcagtgtg   17880
aacaccgttg gcaaatcggc attcgtggag gccgtcggtc gggcgagcga tgatgcggaa   17940
```

```
ggttacctgg attttttcaa aggcaagata accgaatccc atctcggcaa ggagctgctg   18000
gaaaaagtcg agctgacgga ggataacgcc agcagactgg aggagttttc gaaagagtgg   18060
aaggatgcca gtgataagtg gaatgccatg tgggctgtca aaattgagca gaccaaagac   18120
ggcaaacatt atgtcgcggg tattggcctc agcatggagg acacggagga aggcaaactg   18180
agccagtttc tggttgccgc caatcgtatc gcatttattg acccggcaaa cgggaatgaa   18240
acgccgatgt ttgtggcgca gggcaaccag atattcatga cgacgtgtt cctgaagcgc    18300
ctgacggccc ccaccattac cagcggcggc aatcctccgg ccttttccct gacaccggac   18360
ggaaagctga ccgctaaaaa tgcggatatc agtggcagtg tgaatgcgaa ctccgggacg   18420
ctcagtaatg tgacgatagc tgaaaactgt acgataaacg gtacgctgag ggcggaaaaa   18480
atcgtcgggg acattgtaaa ggcggcgagc gcggcttttc cgcgccagcg tgaaagcagt   18540
gtggactggc cgtcaggtac ccgtactgtc accgtgaccg atgaccatcc ttttgatcgc   18600
cagatagtgg tgcttccgct gacgtttcgc ggaagtaagc gtactgtcag cggcaggaca   18660
acgtattcga tgtgttatct gaaagtactg atgaacggtg cggtgattta tgatggcgcg   18720
gcgaacgagg cggtacaggt gttctcccgt attgttgaca tgccagcggg tcggggaaac   18780
gtgatcctga cgttcacgct tacgtccaca cggcattcgg cagatattcc gccgtatacg   18840
tttgccagcg atgtgcaggt tatggtgatt aagaaacagg cgctgggcat cagcgtggtc   18900
tgagtgtgtt acagaggttc gtccgggaac gggcgtttta ttataaaaca gtgagaggtg   18960
aacgatgcgt aatgtgtgta ttgccgttgc tgtctttgcc gcacttgcgg tgacagtcac   19020
tccggcccgt gcggaaggtg acatggtac gtttacggtg ggctattttc aagtgaaacc    19080
gggtacattg ccgtcgttgt cgggcgggga taccggtgtg agtcatctga aagggattaa   19140
cgtgaagtac cgttatgagc tgacggacag tgtgggggtg atggcttccc tggggttcgc   19200
cgcgtcgaaa aagagcagca cagtgatgac cggggaggat acgtttcact atgagagcct   19260
gcgtggacgt tatgtgagcg tgatggccgg accggtttta caaatcagta agcaggtcag   19320
tgcgtacgcc atggccggag tggctcacag tcggtggtcc ggcagtacaa tggattaccg   19380
taagacggaa atcactcccg ggtatatgaa agagacgacc actgccaggg acgaaagtgc   19440
aatgcggcat acctcagtgg cgtggagtgc aggtatacag attaatccgg cagcgtccgt   19500
cgttgttgat attgcttatg aaggctccgg cagtggcgac tggcgtactg acggattcat   19560
cgttggggtc ggttataaat tctgattagc caggtaacac agtgttatga cagcccgccg   19620
gaaccggtgg gcttttttgt ggggtgaata tggcagtaaa gatttcagga gtcctgaaag   19680
acggcacagg aaaaccggta cagaactgca ccattcagct gaaagccaga cgtaacagca   19740
ccacggtggt ggtgaacacg gtgggctcag agaatccgga tgaagccggg cgttacagca   19800
tggatgtgga gtacggtcag tacagtgtca tcctgcaggt tgacggtttt ccaccatcgc   19860
acgccgggac catcaccgtg tatgaagatt cacaaccggg gacgctgaat gattttctct   19920
gtgccatgac ggaggatgat gcccggccgg aggtgctgcg tcgtcttgaa ctgatggtgg   19980
aagaggtggc gcgtaacgcg tccgtggtgg cacagagtac ggcagacgcg aagaaatcag   20040
ccggcgatgc cagtgcatca gctgctcagg tcgcggccct tgtgactgat gcaactgact   20100
cagcacgcgc cgccagcacg tccgccggac aggctgcatc gtcagctcag gaagcgtcct   20160
ccggcgcaga gcggcatca gcaaaggcca ctgaagcgga aaaagtgcc gcagccgcag    20220
agtcctcaaa aaacgcggcg ccaccagtg ccggtgcggc gaaaacgtca gaaacgaatg    20280
```

```
ctgcagcgtc acaacaatca gccgccacgt ctgcctccac cgcggccacg aaagcgtcag   20340
aggccgccac ttcagcacga gatgcggtgg cctcaaaaga ggcagcaaaa tcatcagaaa   20400
cgaacgcatc atcaagtgcc ggtcgtgcag cttcctcggc aacggcggca gaaaattctg   20460
ccagggcgga aaaacgtcc gagacgaatg ccaggtcatc tgaaacagca gcggaacgga    20520
gcgcctctgc cgcggcagac gcaaaaacag cggcggcggg gagtgcgtca acggcatcca   20580
cgaaggcgac agaggctgcg ggaagtgcgg tatcagcatc gcagagcaaa agtgcggcag   20640
aagcggcggc aatacgtgca aaaaattcgg caaaacgtgc agaagatata gcttcagctg   20700
tcgcgcttga ggatgcggac acaacgagaa aggggatagt gcagctcagc agtgcaacca   20760
acagcacgtc tgaaacgctt gctgcaacgc caaaggcggt taaggtggta atggatgaaa   20820
cgaacagaaa agcccactgg acagtccggc actgaccgga acgccaacag caccaaccgc   20880
gctcagggga acaaacaata cccagattgc gaacaccgct tttgtactgg ccgcgattgc   20940
agatgttatc gacgcgtcac ctgacgcact gaatacgctg aatgaactgg ccgcagcgct   21000
cgggaatgat ccagattttg ctaccaccat gactaacgcg cttgcgggta acaaccgaa    21060 gaatgcgaca ctgacggcgc tggcagggct ttccacggcg aaaaataaat taccgtattt   21120
tgcggaaaat gatgccgcca gcctgactga actgactcag gttggcaggg atattctggc   21180
aaaaaattcc gttgcagatg ttcttgaata ccttggggcc ggtgagaatt cggcctttcc   21240
ggcaggtgcg ccgatcccgt ggccatcaga tatcgttccg tctggctacg tcctgatgca   21300
ggggcaggcg tttgacaaat cagcctaccc aaaacttgct gtcgcgtatc catcgggtgt   21360
gcttcctgat atgcgaggct ggacaatcaa ggggaaaccc gccagcggtc gtgctgtatt   21420
gtctcaggaa caggatggaa ttaagtcgca cacccacagt gccagtgcat ccggtacgga   21480
tttggggacg aaaaccacat cgtcgtttga ttacggacg aaaacaacag gcagtttcga    21540
ttacggcacc aaatcgacga ataacacggg ggctcatgct cacagtctga gcggttcaac   21600
aggggccgcg ggtgctcatg cccacacaag tggtttaagg atgaacagtt ctggctggag   21660
tcagtatgga acagcaacca ttacaggaag tttatccaca gttaaaggaa ccagcacaca   21720
gggtattgct tatttatcga aaacggacag tcagggcagc cacagtcact cattgtccgg   21780
tacagccgtg agtgccggtg cacatgcgca tacagttggt attggtgcgc accagcatcc   21840
ggttgttatc ggtgctcatg cccattcttt cagtattggt tcacacggac acaccatcac   21900
cgttaacgct gcgggtaacg cggaaaacac cgtcaaaaac attgcattta actatattgt   21960
gaggcttgca taatggcatt cagaatgagt gaacaaccac ggaccataaa aatttataat   22020
ctgctggccg gaactaatga atttattggt gaaggtgacg catatattcc gcctcatacc   22080
ggtctgcctg caaacagtac cgatattgca ccgccagata ttccggctgg ctttgtggct   22140
gttttcaaca gtgatgaggc atcgtggcat ctcgttgaag accatcgggg taaaaccgtc   22200
tatgacgtgg cttccggcga cgcgttattt atttctgaac tcggtccgtt accggaaaat   22260
tttacctggt tatcgccggg agggaatat cagaagtgga acggcacagc ctgggtgaag    22320
gatacggaag cagaaaaact gttccggatc cgggaggcgg aagaaacaaa aaaagcctg    22380 atgcaggtag ccagtgagca tattgcgccg cttcaggatg ctgcagatct ggaaattgca   22440
acgaaggaag aaacctcgtt gctggaagcc tggaagaagt atcgggtgtt gctgaaccgt   22500
gttgatacat caactgcacc tgatattgag tggcctgctg tccctgttat ggagtaatcg   22560
ttttgtgata tgccgcagaa acgttgtatg aaataacgtt ctgcggttag ttagtatatt   22620
gtaaagctga gtattggttt atttggcgat tattatcttc aggagaataa tggaagttct   22680
```

```
atgactcaat tgttcatagt gtttacatca ccgccaattg cttttaagac tgaacgcatg  22740
aaatatggtt tttcgtcatg ttttgagtct gctgttgata tttctaaagt cggttttttt  22800
tcttcgtttt ctctaactat tttccatgaa atacatttt gattattatt tgaatcaatt   22860
ccaattacct gaagtctttc atctataatt ggcattgtat gtattggttt attggagtag  22920
atgcttgctt ttctgagcca tagctctgat atccaaatga agccataggc atttgttatt  22980
ttggctctgt cagctgcata acgccaaaaa atatatttat ctgcttgatc ttcaaatgtt  23040
gtattgatta aatcaattgg atggaattgt ttatcataaa aaattaatgt ttgaatgtga  23100
taaccgtcct ttaaaaaagt cgtttctgca agcttggctg tatagtcaac taactcttct  23160
gtcgaagtga tattttagg cttatctacc agttttagac gctctttaat atcttcagga   23220
attattttat tgtcatattg tatcatgcta aatgacaatt tgcttatgga gtaatctttt  23280
aattttaaat aagttattct cctggcttca tcaaataaag agtcgaatga tgttggcgaa  23340
atcacatcgt cacccattgg attgtttatt tgtatgccaa gagagttaca gcagttatac  23400
attctgccat agattatagc taaggcatgt aataattcgt aatcttttag cgtattagcg  23460
acccatcgtc tttctgattt aataatagat gattcagtta aatatgaagg taatttcttt  23520
tgtgcaagtc tgactaactt ttttataccha atgtttaaca tactttcatt tgtaataaac  23580
tcaatgtcat tttcttcaat gtaagatgaa ataagagtag cctttgcctc gctatacatt  23640
tctaaatcgc cttgttttc tatcgtattg cgagaatttt tagcccaagc cattaatgga   23700 tcattttcc attttcaat aacattattg ttataccaaa tgtcatatcc tataatctgg    23760
tttttgtttt tttgaataat aaatgttact gttcttgcgg tttggaggaa ttgattcaaa  23820
ttcaagcgaa ataattcagg gtcaaaatat gtatcaatgc agcatttgag caagtgcgat  23880
aaatctttaa gtcttctttc ccatggtttt ttagtcataa aactctccat tttgataggt  23940
tgcatgctag atgctgatat attttagagg tgataaaatt aactgcttaa ctgtcaatgt  24000
aatacaagtt gtttgatctt tgcaatgatt cttatcagaa accatatagt aaattagtta  24060
cacaggaaat ttttaatatt attattatca ttcattatgt attaaaatta gagttgtggc  24120
ttggctctgc taacacgttg ctcataggag atatggtaga gccgcagaca cgtcgtatgc  24180
aggaacgtgc tgcggctggc tggtgaactt ccgatagtgc gggtgttgaa tgatttccag  24240
ttgctaccga ttttacatat ttttttgcatg agagaatttg taccacctcc caccgaccat  24300
ctatgactgt acgccactgt ccctaggact gctatgtgcc ggagcggaca ttacaaacgt  24360
ccttctcggt gcatgccact gttgccaatg acctgcctag gaattggtta gcaagttact  24420
accggatttt gtaaaaacag ccctcctcat ataaaagta ttcgttcact tccgataagc   24480
gtcgtaattt tctatctttc atcatattct agatccctct gaaaaaatct tccgagtttg  24540
ctaggcactg atacataact cttttccaat aattggggaa gtcattcaaa tctataatag  24600
gtttcagatt tgcttcaata aattctgact gtagctgctg aaacgttgcg gttgaactat  24660
atttccttat aactttacg aaagagtttc tttgagtaat cacttcactc aagtgcttcc   24720
ctgcctccaa acgatacctg ttagcaatat ttaatagctt gaaatgatga agagctctgt  24780
gtttgtcttc ctgcctccag ttcgccgggc attcaacata aaaactgata gcacccggag  24840
ttccggaaac gaaatttgca tatacccatt gctcacgaaa aaaaatgtcc ttgtcgatat  24900
agggatgaat cgcttggtgt acctcatcta ctgcgaaaac ttgacctttc tctcccatat  24960
tgcagtcgcg gcacgatgga actaaattaa taggcatcac cgaaaattca ggataatgtg  25020
```

```
caataggaag aaaatgatct atatttttg tctgtcctat atcaccacaa aatggacatt    25080
tttcacctga tgaaacaagc atgtcatcgt aatatgttct agcgggtttg tttttatctc    25140
ggagattatt ttcataaagc ttttctaatt taacctttgt caggttacca actactaagg    25200
ttgtaggctc aagagggtgt gtcctgtcgt aggtaaataa ctgacctgtc gagcttaata    25260
ttctatattg ttgttctttc tgcaaaaaag tggggaagtg agtaatgaaa ttatttctaa    25320
catttatctg catcatacct tccgagcatt tattaagcat ttcgctataa gttctcgctg    25380
gaagaggtag ttttttcatt gtactttacc ttcatctctg ttcattatca tcgcttttaa    25440
aacggttcga ccttctaatc ctatctgacc attataattt tttagaatgg tttcataaga    25500
aagctctgaa tcaacggact gcgataataa gtggtggtat ccagaatttg tcacttcaag    25560
taaaaacacc tcacgagtta aaacacctaa gttctcaccg aatgtctcaa tatccggacg    25620
gataatattt attgcttctc ttgaccgtag gactttccac atgcaggatt ttggaacctc    25680
ttgcagtact actggggaat gagttgcaat tattgctaca ccattgcgtg catcgagtaa    25740
gtcgcttaat gttcgtaaaa aagcagagag caaaggtgga tgcagatgaa cctctggttc    25800
atcgaataaa actaatgact tttcgccaac gacatctact aatcttgtga tagtaaataa    25860
aacaattgca tgtccagagc tcattcgaag cagatatttc tggatattgt cataaaacaa    25920
tttagtgaat ttatcatcgt ccacttgaat ctgtggttca ttacgtctta actcttcata    25980
tttagaaatg aggctgatga gttccatatt tgaaaagttt tcatcactac ttagtttttt    26040
gatagcttca agccagagtt gtcttttct atctactctc atacaaccaa taaatgctga    26100
aatgaattct aagcggagat cgcctagtga ttttaaacta ttgctggcag cattcttgag    26160
tccaatataa aagtattgtg tacctttgc tgggtcaggt tgttctttag gaggagtaaa    26220
aggatcaaat gcactaaacg aaactgaaac aagcgatcga aaatatccct ttgggattct    26280
tgactcgata agtctattat tttcagagaa aaaatattca ttgttttctg ggttggtgat    26340
tgcaccaatc attccattca aaattgttgt tttaccacac ccattccgcc cgataaaagc    26400
atgaatgttc gtgctgggca tagaattaac cgtcacctca aaaggtatag ttaaatcact    26460
gaatccggga gcacttttc tattaaatga aaagtggaaa tctgacaatt ctggcaaacc    26520
atttaacaca cgtgcgaact gtccatgaat ttctgaaaga gttaccctc taagtaatga    26580
ggtgttaagg acgctttcat tttcaatgtc ggctaatcga tttggccata ctactaaatc    26640
ctgaatagct ttaagaaggt tatgtttaaa accatcgctt aatttgctga gattaacata    26700
gtagtcaatg ctttcaccta aggaaaaaaa catttcaggg agttgactga atttttatc    26760
tattaatgaa taagtgctta cttcttcttt ttgacctaca aaaccaattt taacatttcc    26820
gatatcgcat ttttcaccat gctcatcaaa gacagtaaga taaaacattg taacaaagga    26880
atagtcattc caaccatctg ctcgtaggaa tgccttattt ttttctactg caggaatata    26940
cccgcctctt tcaataacac taaactccaa catatagtaa cccttaattt tattaaaata    27000
accgcaattt atttggcggc aacacaggat ctctctttta agttactctc tattacatac    27060
gttttccatc taaaaattag tagtattgaa cttaacgggg catcgtattg tagttttcca    27120
tatttagctt tctgcttcct tttgataac ccactgttat tcatgttgca tggtgcactg    27180
tttataccaa cgatatagtc tattaatgca tatatagtat cgccgaacga ttagctcttc    27240
aggcttctga agaagcgttt caagtactaa taagccgata gatagccacg gacttcgtag    27300
ccatttttca taagtgttaa cttccgctcc tcgctcataa cagacattca ctacagttat    27360
ggcggaaagg tatgcatgct gggtgtgggg aagtcgtgaa agaaaagaag tcagctgcgt    27420
```

```
cgtttgacat cactgctatc ttcttactgg ttatgcaggt cgtagtgggt ggcacacaaa   27480
gctttgcact ggattgcgag gctttgtgct tctctggagt gcgacaggtt tgatgacaaa   27540
aaattagcgc aagaagacaa aaatcacctt gcgctaatgc tctgttacag gtcactaata   27600
ccatctaagt agttgattca tagtgactgc atatgttgtg ttttacagta ttatgtagtc   27660
tgttttttat gcaaaatcta atttaatata ttgatatttta tatcatttta cgtttctcgt   27720
tcagcttttt tatactaagt tggcattata aaaagcatt gcttatcaat ttgttgcaac   27780
gaacaggtca ctatcagtca aaataaaatc attatttgat ttcaattttg tcccactccc   27840
tgcctctgtc atcacgatac tgtgatgcca tggtgtccga cttatgcccg agaagatgtt   27900
gagcaaactt atcgcttatc tgcttctcat agagtcttgc agacaaactg cgcaactcgt   27960
gaaaggtagg cggatcccct tcgaaggaaa gacctgatgc ttttcgtgcg cgcataaaat   28020
accttgatac tgtgccggat gaaagcggtt cgcgacgagt agatgcaatt atggtttctc   28080
cgccaagaat ctctttgcat ttatcaagtg tttccttcat tgatattccg agagcatcaa   28140
tatgcaatgc tgttgggatg gcaatttta cgcctgtttt gctttgctcg acataaagat   28200
atccatctac gatatcagac cacttcattt cgcataaatc accaactcgt tgcccggtaa   28260
caacagccag ttccattgca agtctgagcc aacatggtga tgattctgct gcttgataaa   28320
ttttcaggta ttcgtcagcc gtaagtcttg atctccttac ctctgatttt gctgcgcgag   28380
tggcagcgac atggtttgtt gttatatggc cttcagctat tgcctctcgg aatgcatcgc   28440
tcagtgttga tctgattaac ttggctgacg ccgccttgcc ctcgtctatg tatccattga   28500
gcattgccgc aatttctttt gtggtgatgt cttcaagtgg agcatcaggc agaccctcc   28560 ttattgcttt aattttgctc atgtaattta tgagtgtctt ctgcttgatt cctctgctgg   28620
ccaggatttt ttcgtagcga tcaagccatg aatgtaacgt aacggaatta tcactgttga   28680
ttctcgctgt cagaggcttg tgtttgtgtc ctgaaaataa ctcaatgttg gcctgtatag   28740
cttcagtgat tgcgattcgc ctgtctctgc ctaatccaaa ctctttaccc gtccttgggt   28800
ccctgtagca gtaatatcca ttgtttctta tataaaggtt aggggtaaa tcccggcgct   28860 catgacttcg ccttcttccc atttctgatc ctcttcaaaa ggccacctgt tactggtcga   28920
tttaagtcaa cctttaccgc tgattcgtgg aacagatact ctcttccatc cttaaccgga   28980
ggtgggaata tcctgcattc ccgaacccat cgacgaactg tttcaaggct tcttggacgt   29040
cgctggcgtg cgttccactc ctgaagtgtc aagtacatcg caaagtctcc gcaattacac   29100
gcaagaaaaa accgccatca ggcggcttgg tgttctttca gttcttcaat tcgaatattg   29160
gttacgtctg catgtgctat ctgcgcccat atcatccagt ggtcgtagca gtcgttgatg   29220
ttctccgctt cgataactct gttgaatggc tctccattcc attctcctgt gactcggaag   29280
tgcatttatc atctccataa aacaaaaccc gccgtagcga gttcagataa aataaatccc   29340
cgcgagtgcg aggattgtta tgtaatattg ggtttaatca tctatatgtt ttgtacagag   29400
agggcaagta tcgtttccac cgtactcgtg ataataattt tgcacggtat cagtcatttc   29460
tcgcacattg cagaatgggg atttgtcttc attagactta taaaccttca tggaatattt   29520
gtatgccgac tctatatcta taccttcatc tacataaaca ccttcgtgat gtctgcatgg   29580
agacaagaca ccggatctgc acaacattga taacgcccaa tcttttttgct cagactctaa   29640 ctcattgata ctcattttata aactccttgc aatgtatgtc gtttcagcta aacggtatca   29700
gcaatgttta tgtaaagaaa cagtaagata atactcaacc cgatgtttga gtacggtcat   29760
```

-continued

```
catctgacac tacagactct ggcatcgctg tgaagacgac gcgaaattca gcattttcac    29820
aagcgttatc ttttacaaaa ccgatctcac tctcctttga tgcgaatgcc agcgtcagac    29880
atcatatgca gatactcacc tgcatcctga acccattgac ctccaacccc gtaatagcga    29940
tgcgtaatga tgtcgatagt tactaacggg tcttgttcga ttaactgccg cagaaactct    30000
tccaggtcac cagtgcagtg cttgataaca ggagtcttcc caggatggcg aacaacaaga    30060
aactggtttc cgtcttcacg gacttcgttg cttttccagtt tagcaatacg cttactccca    30120
tccgagataa caccttcgta atactcacgc tgctcgttga gttttgattt tgctgtttca    30180
agctcaacac gcagtttccc tactgttagc gcaatatcct cgttctcctg gtcgcggcgt    30240
ttgatgtatt gctggtttct ttcccgttca tccagcagtt ccagcacaat cgatggtgtt    30300
accaattcat ggaaaaggtc tgcgtcaaat ccccagtcgt catgcattgc ctgctctgcc    30360
gcttcacgca gtgcctgaga gttaatttcg ctcacttcga acctctctgt ttactgataa    30420
gttccagatc ctcctggcaa cttgcacaag tccgacaacc ctgaacgacc aggcgtcttc    30480
gttcatctat cggatcgcca cactcacaac aatgagtggc agatatagcc tggtggttca    30540
ggcggcgcat ttttattgct gtgttgcgct gtaattcttc tatttctgat gctgaatcaa    30600
tgatgtctgc catctttcat taatccctga actgttggtt aatacgcttg agggtgaatg    30660
cgaataataa aaaaggagcc tgtagctccc tgatgatttt gcttttcatg ttcatcgttc    30720
cttaaagacg ccgtttaaca tgccgattgc caggcttaaa tgagtcggtg tgaatcccat    30780
cagcgttacc gtttcgcggt gcttcttcag tacgctacgg caaatgtcat cgacgttttt    30840
atccggaaac tgctgtctgg ctttttttga tttcagaatt agcctgacgg gcaatgctgc    30900
gaagggcgtt ttcctgctga ggtgtcattg aacaagtccc atgtcggcaa gcataagcac    30960
acagaatatg aagcccgctg ccagaaaaat gcattccgtg gttgtcatac ctggtttctc    31020
tcatctgctt ctgctttcgc caccatcatt tccagctttt gtgaaaggga tgcggctaac    31080
gtatgaaatt cttcgtctgt ttctactggt attggcacaa acctgattcc aatttgagca    31140
aggctatgtg ccatctcgat actcgttctt aactcaacag aagatgcttt gtgcatacag    31200
cccctcgttt attatttatc tcctcagcca gccgctgtgc tttcagtgga tttcggataa    31260
cagaaaggcc gggaaatacc cagcctcgct ttgtaacgga gtagacgaaa gtgattgcgc    31320
ctacccggat attatcgtga ggatgcgtca tcgccattgc tccccaaata caaaccaat    31380
ttcagccagt gcctcgtcca ttttttcgat gaactccggc acgatctcgt caaaactcgc    31440
catgtacttt tcatcccgct caatcacgac ataatgcagg ccttcacgct tcatacgcgg    31500
gtcatagttg gcaaagtacc aggcattttt tcgcgtcacc cacatgctgt actgcacctg    31560
ggccatgtaa gctgacttta tggcctcgaa accaccgagc cggaacttca tgaaatcccg    31620
ggaggtaaac gggcatttca gttcaaggcc gttgccgtca ctgcataaac catcgggaga    31680
gcaggcggta cgcatacttt cgtcgcgata tgatcgggg gattcagtaa cattcacgcc    31740
ggaagtgaat tcaaacaggg ttctggcgtc gttctcgtac tgttttcccc aggccagtgc    31800
tttagcgtta acttccggag ccacaccggt gcaaacctca gcaagcaggg tgtggaagta    31860
ggacattttc atgtcaggcc acttctttcc ggagcggggt tttgctatca cgttgtgaac    31920
ttctgaagcg gtgatgacgc cgagccgtaa tttgtgccac gcatcatccc cctgttcgac    31980
agctctcaca tcgatcccgg tacgctgcag gataatgtcc ggtgtcatgc tgccaccttc    32040
tgctctgcgc ctttctgttt caggaatcca agagcttttt actcttcggc ctgtgtcagt    32100
tctgacgatg cacgaatgtc gcggcgaaat atctgggaac agagcggcaa taagtcgtca    32160
```

```
tcccatgttt tatccagggc gatcagcaga gtgttaatct cctgcatggt ttcatcgtta    32220
accggagtga tgtcgcgttc cggctgacgt tctgcagtgt atgcagtatt ttcgacaatg    32280
cgctcggctt catccttgtc atagatacca gcaaatccga aggccagacg ggcacactga    32340
atcatggctt tatgacgtaa catccgtttg ggatgcgact gccacggccc cgtgatttct    32400
ctgccttcgc gagttttgaa tggttcgcgg cggcattcat ccatccattc ggtaacgcag    32460
atcggatgat tacggtcctt gcggtaaatc cggcatgtac aggattcatt gtcctgctca    32520
aagtccatgc catcaaactg ctggttttca ttgatgatgc gggaccagcc atcaacgccc    32580
accaccggaa cgatgccatt ctgccttatc aggaaaggcg aaatttcttt cgtccacgga    32640
ttaaggccgt actggttggc aacgatcagt aatgcgatga actgcgcatc gctggcatca    32700
cctttaaatg ccgtctggcg aagagtggtg atcagttcct gtgggtcgac agaatccatg    32760
ccgacacgtt cagccagctt cccagccagc gttgcgagtg cagtactcat tcgtttttata   32820 cctctgaatc aatatcaacc tggtggtgag caatggtttc aaccatgtac cggatgtgtt    32880
ctgccatgcg ctcctgaaac tcaacatcgt catcaaacgc acgggtaatg gattttttgc    32940
tggccccgtg gcgttgcaaa tgatcgatgc atagcgattc aaacaggtgc tggggcaggc    33000 cttttttccat gtcgtctgcc agttctgcct cttttctcttc acgggcgagc tgctggtagt    33060
gacgcgccca gctctgagcc tcaagacgat cctgaatgta ataagcgttc atggctgaac    33120
tcctgaaata gctgtgaaaa tatcgcccgc gaaatgccgg gctgattagg aaaacaggaa    33180
agggggttag tgaatgcttt tgcttgatct cagtttcagt attaatatcc atttttttata   33240 agcgtcgacg gcttcacgaa acatcttttc atcgccaata aaagtggcga tagtgaattt    33300
agtctggata gccataagtg tttgatccat tctttgggac tcctggctga ttaagtatgt    33360
cgataaggcg tttccatccg tcacgtaatt tacgggtgat tcgttcaagt aaagattcgg    33420
aagggcagcc agcaacaggc caccctgcaa tggcatattg catggtgtgc tccttattta    33480
tacataacga aaaacgcctc gagtgaagcg ttattggtat gcggtaaaac cgcactcagg    33540
cggccttgat agtcatatca tctgaatcaa atattcctga tgtatcgata tcggtaattc    33600
ttattccttc gctaccatcc attggaggcc atccttcctg accatttcca tcattccagt    33660
cgaactcaca cacaacacca tatgcattta agtcgcttga aattgctata agcagagcat    33720
gttgcgccag catgattaat acagcattta atacagagcc gtgtttattg agtcggtatt    33780
cagagtctga ccagaaatta ttaatctggt gaagtttttc ctctgtcatt acgtcatggt    33840
cgatttcaat ttctattgat gctttccagt cgtaatcaat gatgtatttt ttgatgtttg    33900
acatctgttc atatcctcac agataaaaaa tcgccctcac actggagggc aaagaagatt    33960
tccaataatc agaacaagtc ggctcctgtt tagttacgag cgacattgct ccgtgtattc    34020
actcgttgga atgaatacac agtgcagtgt ttattctgtt atttatgcca aaaataaagg    34080
ccactatcag gcagctttgt tgttctgttt accaagttct ctggcaatca ttgccgtcgt    34140
tcgtattgcc catttatcga catatttccc atcttccatt acaggaaaca tttcttcagg    34200
cttaaccatg cattccgatt gcagcttgca tccattgcat cgcttgaatt gtccacacca    34260
ttgattttta tcaatagtcg tagtcatacg gatagtcctg gtattgttcc atcacatcct    34320
gaggatgctc ttcgaactct tcaaattctt cttccatata tcaccttaaa tagtggattg    34380
cggtagtaaa gattgtgcct gtcttttaac cacatcaggc tcggtggttc tcgtgtaccc    34440
ctacagcgag aaatcggata aactattaca acccctacag tttgatgagt atagaaatgg    34500
```

```
atccactcgt tattctcgga cgagtgttca gtaatgaacc tctggagaga accatgtata    34560
tgatcgttat ctgggttgga cttctgcttt taagcccaga taactggcct gaatatgtta    34620
atgagagaat cggtattcct catgtgtggc atgttttcgt ctttgctctt gcattttcgc    34680
tagcaattaa tgtgcatcga ttatcagcta ttgccagcgc cagatataag cgatttaagc    34740
taagaaaacg cattaagatg caaaacgata aagtgcgatc agtaattcaa aaccttacag    34800
aagagcaatc tatggttttg tgcgcagccc ttaatgaagg caggaagtat gtggttacat    34860
caaaacaatt cccatacatt agtgagttga ttgagcttgg tgtgttgaac aaaacttttt    34920
cccgatggaa tggaaagcat atattattcc ctattgagga tatttactgg actgaattag    34980
ttgccagcta tgatccatat aatattgaga taaagccaag gccaatatct aagtaactag    35040
ataagaggaa tcgattttcc cttaattttc tggcgtccac tgcatgttat gccgcgttcg    35100
ccaggcttgc tgtaccatgt gcgctgattc ttgcgctcaa tacgttgcag gttgctttca    35160
atctgtttgt ggtattcagc cagcactgta aggtctatcg gatttagtgc gctttctact    35220
cgtgatttcg gtttgcgatt cagcgagaga atagggcggt taactggttt tgcgcttacc    35280
ccaaccaaca ggggatttgc tgctttccat tgagcctgtt tctctgcgcg acgttcgcgg    35340
cggcgtgttt gtgcatccat ctggattctc ctgtcagtta gctttggtgg tgtgtggcag    35400
ttgtagtcct gaacgaaaac cccccgcgat tggcacattg gcagctaatc cggaatcgca    35460
cttacggcca atgcttcgtt tcgtatcaca caccccaaag cctctgctt tgaatgctgc    35520 ccttcttcag ggcttaattt ttaagagcgt caccttcatg gtggtcagtg cgtcctgctg    35580
atgtgctcag tatcaccgcc agtggtattt atgtcaacac cgccagagat aatttatcac    35640
cgcagatggt tatctgtatg ttttttatat gaatttattt tttgcagggg ggcattgttt    35700
ggtaggtgag agatctgaat tgctatgttt agtgagttgt atctatttat ttttcaataa    35760
atacaattgg ttatgtgttt tgggggcgat cgtgaggcaa agaaaacccg gcgctgaggc    35820
cgggttattc ttgttctctg gtcaaattat atagttggaa acaaggatg catatatgaa    35880 tgaacgatgc agaggcaatg ccgatggcga tagtgggtat catgtagccg cttatgctgg    35940
aaagaagcaa taacccgcag aaaaacaaag ctccaagctc aacaaaacta agggcataga    36000
caataactac cgatgtcata tacccatact ctctaatctt ggccagtcgg cgcgttctgc    36060
ttccgattag aaacgtcaag gcagcaatca ggattgcaat catggttcct gcatatgatg    36120
acaatgtcgc cccaagacca tctctatgag ctgaaaaaga acaccagga atgtagtggc    36180 ggaaaaggag atagcaaatg cttacgataa cgtaaggaat tattactatg taaacaccag    36240
gcatgattct gttccgcata attactcctg ataattaatc cttaactttg cccacctgcc    36300 tttttaaaaca ttccagtata tcacttttca ttccttgcgta gcaatatgcc atctcttcag    36360
ctatctcagc attggtgacc ttgttcagag gcgctgagag atggcctttt tctgatagat    36420
aatgttctgt taaatatct ccggcctcat cttttgcccg caggctaatg tctgaaaatt    36480
gaggtgacgg gttaaaaata atatccttgg caaccttttt tatatccctt ttaaattttg    36540
gcttaatgac tatatccaat gagtcaaaaa gctccccttc aatatctgtt gcccctaaga    36600
cctttaatat atcgccaaat acaggtagct tggcttctac cttcaccgtt gttcggccga    36660
tgaaatgcat atgcataaca tcgtctttgg tggttcccct catcagtggc tctatctgaa    36720
cgcgctctcc actgcttaat gacattcctt tcccgattaa aaaatctgtc agatcggatg    36780
tggtcggccc gaaaacagtt ctggcaaaac caatggtgtc gccttcaaca aacaaaaaag    36840
atgggaatcc caatgattcg tcatctgcga ggctgttctt aatatcttca actgaagctt    36900
```

```
tagagcgatt tatcttctga accagactct tgtcatttgt tttggtaaag agaaaagttt    36960
ttccatcgat tttatgaata tacaaataat tggagccaac ctgcaggtga tgattatcag    37020
ccagcagaga attaaggaaa acagacaggt ttattgagcg cttatctttc cctttatttt    37080
tgctgcggta agtcgcataa aaccattct tcataattca atccatttac tatgttatgt     37140
tctgagggga gtgaaaattc ccctaattcg atgaagattc ttgctcaatt gttatcagct    37200
atgcgccgac cagaacacct tgccgatcag ccaaacgtct cttcaggcca ctgactagcg    37260
ataactttcc ccacaacgga acaactctca ttgcatggga tcattgggta ctgtgggttt    37320
agtggttgta aaaacacctg accgctatcc ctgatcagtt tcttgaaggt aaactcatca    37380
cccccaagtc tggctatgca gaaatcacct ggctcaacag cctgctcagg gtcaacgaga    37440
attaacattc cgtcaggaaa gcttggcttg gagcctgttg gtgcggtcat ggaattacct    37500
tcaacctcaa gccagaatgc agaatcactg gcttttttgg ttgtgcttac ccatctctcc    37560
gcatcacctt tggtaaaggt tctaagctta ggtgagaaca tccctgcctg aacatgagaa    37620
aaaacagggt actcatactc acttctaagt gacggctgca tactaaccgc ttcatacatc    37680
tcgtagattt ctctggcgat tgaagggcta aattcttcaa cgctaacttt gagaattttt    37740
gtaagcaatg cggcgttata agcatttaat gcattgatgc cattaaataa agcaccaacg    37800
cctgactgcc ccatccccat cttgtctgcg acagattcct gggataagcc aagttcattt    37860 ttctttttt cataaattgc tttaaggcga cgtgcgtcct caagctgctc ttgtgttaat     37920
ggtttctttt ttgtgctcat acgttaaatc tatcaccgca agggataaat atctaacacc    37980
gtgcgtgttg actatttac ctctggcggt gataatggtt gcatgtacta aggaggttgt     38040
atggaacaac gcataaccct gaaagattat gcaatgcgct ttgggcaaac caagacagct    38100
aaagatctcg gcgtatatca agcgcgatc aacaaggcca ttcatgcagg ccgaaagatt     38160
tttttaacta taaacgctga tggaagcgtt tatgcggaag aggtaaagcc cttcccgagt    38220
aacaaaaaaa caacagcata ataaccccg ctcttacaca ttccagcccct gaaaagggc     38280 atcaaattaa accacaccta tggtgtatgc atttatttgc atacattcaa tcaattgtta    38340
tctaaggaaa tacttacata tggttcgtgc aaacaaacgc aacgaggctc tacgaatcga    38400
gagtgcgttg cttaacaaaa tcgcaatgct tggaactgag aagacagcgg aagctgtggg    38460
cgttgataag tcgcagatca gcaggtgaa gagggactgg attccaaagt tctcaatgct     38520
gcttgctgtt cttgaatggg gggtcgttga cgacgacatg gctcgattgg cgcgacaagt    38580
tgctgcgatt ctcaccaata aaaaacgccc ggcggcaacc gagcgttctg aacaaatcca    38640
gatggagttc tgaggtcatt actggatcta tcaacaggag tcattatgac aaatacagca    38700
aaaatactca acttcggcag aggtaacttt gccggacagg agcgtaatgt ggcagatctc    38760
gatgatggtt acgccagact atcaaatatg ctgcttgagg cttattcggg cgcagatctg    38820
accaagcgac agtttaaagt gctgcttgcc attctgcgta aaacctatgg gtggaataaa    38880
ccaatggaca gaatcaccga ttctcaactt agcgagatta caaagttacc tgtcaaacgg    38940
tgcaatgaag ccaagttaga actcgtcaga atgaatatta tcaagcagca aggcggcatg    39000
tttggaccaa ataaaaacat ctcagaatgg tgcatccctc aaaacgaggg aaaatcccct    39060
aaaacgaggg ataaaacatc cctcaaattg ggggattgct atccctcaaa acaggggac    39120 acaaaagaca ctattacaaa agaaaaaaga aagattatt cgtcagagaa ttctggcgaa     39180
tcctctgacc agccagaaaa cgacctttct gtggtgaaac cggatgctgc aattcagagc    39240
```

```
ggcagcaagt gggggacagc agaagacctg accgccgcag agtggatgtt tgacatggtg    39300
aagactatcg caccatcagc cagaaaaccg aattttgctg ggtgggctaa cgatatccgc    39360
ctgatgcgtg aacgtgacgg acgtaaccac cgcgacatgt gtgtgctgtt ccgctgggca    39420
tgccaggaca acttctggtc cggtaacgtg ctgagcccgg ccaaactccg cgataagtgg    39480
acccaactcg aaatcaaccg taacaagcaa caggcaggcg tgacagccag caaaccaaaa    39540
ctcgacctga caaacacaga ctggatttac ggggtggatc tatgaaaaac atcgccgcac    39600
agatggttaa ctttgaccgt gagcagatgc gtcggatcgc caacaacatg ccggaacagt    39660
acgacgaaaa gccgcaggta cagcaggtag cgcagatcat caacggtgtg ttcagccagt    39720
tactggcaac tttcccggcg agcctggcta accgtgacca gaacgaagtg aacgaaatcc    39780
gtcgccagtg ggttctggct tttcgggaaa acgggatcac cacgatggaa caggttaacg    39840
caggaatgcg cgtagcccgt cggcagaatc gaccatttct gccatcaccc gggcagtttg    39900
ttgcatggtg ccgggaagaa gcatccgtta ccgccggact gccaaacgtc agcgagctgg    39960
ttgatatggt ttacgagtat tgccggaagc gaggcctgta tccggatgcg gagtcttatc    40020
cgtggaaatc aaacgcgcac tactggctgg ttaccaacct gtatcagaac atgcgggcca    40080
atgcgcttac tgatgcggaa ttcgccgta aggccgcaga tgagcttgtc catatgactc    40140
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tggggacgca    40320
taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccggtttg ctaccaggga agaacgggaa ggaaagatga gcacgaacct    40500
ggtttttaag gagtgtcgcc agagtgccgc gatgaaacgg gtattggcgg tatatggagt    40560
taaaagatga ccatctacat tactgagcta ataacaggcc tgctggtaat cgcaggcctt    40620
tttatttggg ggagagggaa gtcatgaaaa aactaacctt tgaaattcga tctccagcac    40680
atcagcaaaa cgctattcac gcagtacagc aaatccttcc agacccaacc aaaccaatcg    40740
tagtaaccat tcaggaacgc aaccgcagct tagaccaaaa caggaagcta tgggcctgct    40800
taggtgacgt ctctcgtcag gttgaatggc atggtcgctg gctggatgca gaaagctgga    40860
agtgtgtgtt taccgcagca ttaaagcagc aggatgttgt tcctaacctt gccgggaatg    40920
gctttgtggt aataggccag tcaaccagca ggatgcgtgt aggcgaattt gcggagctat    40980
tagagcttat acaggcattc ggtacagagc gtggcgttaa gtggtcagac gaagcgagac    41040
tggctctgga gtgaaagcg agatggggag acagggctgc atgataaatg tcgttagttt    41100
ctccggtggc aggacgtcag catatttgct ctggctaatg gagcaaaagc gacgggcagg    41160
taaagacgtg cattacgttt tcatggatac aggttgtgaa catccaatga catatccggtt   41220 tgtcagggaa gttgtgaagt tctgggatat accgctcacc gtattgcagg ttgatatcaa    41280
cccggagctt ggacagccaa atggttatac ggtatgggaa ccaaaggata ttcagacgcg    41340
aatgcctgtt ctgaagccat ttatcgtat ggtaaagaaa tatggcactc catacgtcgg    41400
cggcgcgttc tgcactgaca gattaaaact cgttcccttc accaaatact gtgatgacca    41460
tttcgggcga gggaattaca ccacgtggat tggcatcaga gctgatgaac cgaagcggct    41520
aaagccaaag cctggaatca gatatcttgc tgaactgtca gactttgaga aggaagatat    41580
cctcgcatgg tggaagcaac aaccattcga tttgcaaata ccggaacatc tcggtaactg    41640
```

```
catattctgc attaaaaaat caacgcaaaa aatcggactt gcctgcaaag atgaggaggg    41700
attgcagcgt gtttttaatg aggtcatcac gggatcccat gtgcgtgacg gacatcggga    41760
aacgccaaag gagattatgt accgaggaag aatgtcgctg gacggtatcg cgaaaatgta    41820
ttcagaaaat gattatcaag ccctgtatca ggacatggta cgagctaaaa gattcgatac    41880
cggctcttgt tctgagtcat gcgaaatatt tggagggcag cttgatttcg acttcgggag    41940
ggaagctgca tgatgcgatg ttatcggtgc ggtgaatgca aagaagataa ccgcttccga    42000
ccaaatcaac cttactggaa tcgatggtgt ctccggtgtg aaagaacacc aacaggggtg    42060
ttaccactac cgcaggaaaa ggaggacgtg tggcgagaca gcgacgaagt atcaccgaca    42120
taatctgcga aaactgcaaa taccttccaa cgaaacgcac cagaaataaa cccaagccaa    42180
tcccaaaaga atctgacgta aaaaccttca actacacggc tcacctgtgg gatatccggt    42240
ggctaagacg tcgtgcgagg aaaacaaggt gattgaccaa aatcgaagtt acgaacaaga    42300
aagcgtcgag cgagctttaa cgtgcgctaa ctgcggtcag aagctgcatg tgctggaagt    42360
tcacgtgtgt gagcactgct gcgcagaact gatgagcgat ccgaatagct cgatgcacga    42420
ggaagaagat gatggctaaa ccagcgcgaa gacgatgtaa aaacgatgaa tgccgggaat    42480
ggtttcaccc tgcattcgct aatcagtggt ggtgctctcc agagtgtgga accaagatag    42540
cactcgaacg acgaagtaaa gaacgcgaaa aagcggaaaa agcagcagag aagaaacgac    42600
gacgagagga gcagaaacag aaagataaac ttaagattcg aaaactcgcc ttaaagcccc    42660
gcagttactg gattaaacaa gcccaacaag ccgtaaacgc cttcatcaga gaaagagacc    42720
gcgacttacc atgtatctcg tgcggaacgc tcacgtctgc tcagtgggat gccggacatt    42780
accggacaac tgctgcggca cctcaactcc gatttaatga acgcaatatt cacaagcaat    42840
gcgtggtgtg caaccagcac aaaagcggaa atctcgttcc gtatcgcgtc gaactgatta    42900
gccgcatcgg gcaggaagca gtagacgaaa tcgaatcaaa ccataaccgc catcgctgga    42960
ctatcgaaga gtgcaaggcg atcaaggcag agtaccaaca gaaactcaaa gacctgcgaa    43020
atagcagaag tgaggccgca tgacgttctc agtaaaaacc attccagaca tgctcgttga    43080
aacatacgga aatcagacag aagtagcacg cagactgaaa tgtagtcgcg gtacggtcag    43140
aaaatacgtt gatgataaag acgggaaaat gcacgccatc gtcaacgacg ttctcatggt    43200
tcatcgcgga tggagtgaaa gagatgcgct attacgaaaa aattgatggc agcaaatacc    43260
gaaatatttg ggtagttggc gatctgcacg gatgctacac gaacctgatg aacaaactgg    43320
atacgattgg attcgacaac aaaaaagacc tgcttatctc ggtgggcgat ttggttgatc    43380
gtggtgcaga gaacgttgaa tgcctggaat taatcacatt ccctggttc agagctgtac    43440
gtggaaacca tgagcaaatg atgattgatg gcttatcaga gcgtggaaac gttaatcact    43500
ggctgcttaa tggcggtggc tggttctttta atctcgatta cgacaaagaa attctggcta    43560
aagctcttgc ccataaagca gatgaacttc cgttaatcat cgaactggtg agcaaagata    43620
aaaaatatgt tatctgccac gccgattatc cctttgacga atacgagttt ggaaagccag    43680
ttgatcatca gcaggtaatc tggaaccgcg aacgaatcag caactcacaa aacgggatcg    43740
tgaaagaaat caaaggcgcg gacacgttca tctttggtca tacgccagca gtgaaaccac    43800
tcaagtttgc caaccaaatg tatatcgata ccggcgcagt gttctgcgga aacctaacat    43860
tgattcaggt acagggagaa ggcgcatgag actcgaaagc gtagctaaat tcattcgcc    43920
aaaaagcccg atgatgagcg actcaccacg ggccacggct tctgactctc tttccggtac    43980
```

```
tgatgtgatg gctgctatgg ggatggcgca atcacaagcc ggattcggta tggctgcatt    44040
ctgcggtaag cacgaactca gccagaacga caaacaaaag gctatcaact atctgatgca    44100
atttgcacac aaggtatcgg ggaaataccg tggtgtggca aagcttgaag gaaatactaa    44160
ggcaaaggta ctgcaagtgc tcgcaacatt cgcttatgcg gattattgcc gtagtgccgc    44220
gacgccgggg gcaagatgca gagattgcca tggtacaggc cgtgcggttg atattgccaa    44280
aacagagctg tgggggagag ttgtcgagaa agagtgcgga agatgcaaag gcgtcggcta    44340
ttcaaggatg ccagcaagcg cagcatatcg cgctgtgacg atgctaatcc caaaccttac    44400
ccaacccacc tggtcacgca ctgttaagcc gctgtatgac gctctggtgg tgcaatgcca    44460
caaagaagag tcaatcgcag acaacatttt gaatgcggtc acacgttagc agcatgattg    44520
ccacggatgg caacatatta acggcatgat attgacttat tgaataaaat tgggtaaatt    44580
tgactcaacg atgggttaat tcgctcgttg tggtagtgag atgaaaagag gcggcgctta    44640
ctaccgattc cgcctagttg gtcacttcga cgtatcgtct ggaactccaa ccatcgcagg    44700
cagagaggtc tgcaaaatgc aatcccgaaa cagttcgcag gtaatagtta gagcctgcat    44760
aacggtttcg ggatttttta tatctgcaca acaggtaaga gcattgagtc gataatcgtg    44820
aagagtcggc gagcctggtt agccagtgct ctttccgttg tgctgaatta agcgaatacc    44880
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggt ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattggggt    45180 aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tagttcattc    45360
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga aatcaataat caacgtaagg cgttcctcga tatgctggcg    45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgctttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
gatgtatgag cagagtcacc gcgattatct ccgctctggt tatctgcatc atcgtctgcc    46020
tgtcatgggc tgttaatcat taccgtgata acgccattac ctacaaagcc cagcgcgaca    46080
aaaatgccag agaactgaag ctggcgaacg cggcaattac tgacatgcag atgcgtcagc    46140
gtgatgttgc tgcgctcgat gcaaaataca cgaaggagtt agctgatgct aaagctgaaa    46200
atgatgctct gcgtgatgat gttgccgctg tcgtcgtcg gttgcacatc aaagcagtct    46260
gtcagtcagt gcgtgaagcc accaccgcct ccggcgtgga taatgcagcc tcccccgac    46320 tggcagacac cgctgaacgg gattatttca ccctcagaga gaggctgatc actatgcaaa    46380
```

```
aacaactgga aggaacccag aagtatatta atgagcagtg cagatagagt tgcccatatc    46440
gatgggcaac tcatgcaatt attgtgagca atacacacgc gcttccagcg gagtataaat    46500
gcctaaagta ataaaaccga gcaatccatt tacgaatgtt tgctgggttt ctgttttaac    46560
aacattttct gcgccgccac aaattttggc tgcatcgaca gttttcttct gcccaattcc    46620
agaaacgaag aaatgatggg tgatggtttc ctttggtgct actgctgccg gtttgttttg    46680
aacagtaaac gtctgttgag cacatcctgt aataagcagg gccagcgcag tagcgagtag    46740
catttttttc atggtgttat tcccgatgct ttttgaagtt cgcagaatcg tatgtgtaga    46800
aaattaaaca aaccctaaac aatgagttga aatttcatat tgttaatatt tattaatgta    46860
tgtcaggtgc gatgaatcgt cattgtattc ccggattaac tatgtccaca gccctgacgg    46920
ggaacttctc tgcgggagtg tccgggaata attaaaacga tgcacacagg gtttagcgcg    46980
tacacgtatt gcattatgcc aacgccccgg tgctgacacg gaagaaaccg gacgttatga    47040
tttagcgtgg aaagatttgt gtagtgttct gaatgctctc agtaaatagt aatgaattat    47100
caaaggtata gtaatatctt ttatgttcat ggatatttgt aacccatcgg aaaactcctg    47160
ctttagcaag attttccctg tattgctgaa atgtgatttc tcttgatttc aacctatcat    47220
aggacgtttc tataagatgc gtgtttcttg agaatttaac atttacaacc ttttttaagtc   47280 cttttattaa cacggtgtta tcgtttttcta acacgatgtg aatattatct gtggctagat   47340
agtaaatata atgtgagacg ttgtgacgtt ttagttcaga ataaaacaat tcacagtcta    47400
aatcttttcg cacttgatcg aatatttctt taaaaatggc aacctgagcc attggtaaaa    47460
ccttccatgt gatacgaggg cgcgtagttt gcattatcgt ttttatcgtt tcaatctggt    47520
ctgacctcct tgtgttttgt tgatgattta tgtcaaatat taggaatgtt ttcacttaat    47580
agtattggtt gcgtaacaaa gtgcggtcct gctggcattc tggagggaaa tacaaccgac    47640
agatgtatgt aaggccaacg tgctcaaatc ttcatacaga aagatttgaa gtaatatttt    47700
aaccgctaga tgaagagcaa gcgcatggag cgacaaaatg aataaagaac aatctgctga    47760
tgatccctcc gtggatctga ttcgtgtaaa aaatatgctt aatagcacca tttctatgag    47820
ttaccctgat gttgtaattg catgtataga acataaggtg tctctggaag cattcagagc    47880
aattgaggca gcgttggtga agcacgataa taatatgaag gattattccc tggtggttga    47940
ctgatcacca taactgctaa tcattcaaac tatttagtct gtgacagagc caacacgcag    48000
tctgtcactg tcaggaaagt ggtaaaactg caactcaatt actgcaatgc cctcgtaatt    48060
aagtgaattt acaatatcgt cctgttcgga gggaagaacg cgggatgttc attcttcatc    48120 actttttaatt gatgtatatg ctctcttttc tgacgttagt ctccgacggc aggcttcaat    48180
gacccaggct gagaaattcc cggacccttt ttgctcaaga gcgatgttaa tttgttcaat    48240
catttggtta ggaaagcgga tgttgcgggt tgttgttctg cgggttctgt tcttcgttga    48300
catgaggttg ccccgtattc agtgtcgctg atttgtattg tctgaagttg tttttacgtt    48360
aagttgatgc agatcaatta atacgatacc tgcgtcataa ttgattattt gacgtggttt    48420
gatggcctcc acgcacgttg tgatatgtag atgataatca ttatcacttt acgggtcctt    48480
tccggtgatc cgacaggtta cg                                              48502

<210> SEQ ID NO 30
<211> LENGTH: 85
<212> TYPE: DNA
<213> ORGANISM: Artificial Sequence
<220> FEATURE:
```

<223> OTHER INFORMATION: sequence used in Example 2

<400> SEQUENCE: 30
ttatcgtgaa actccggagc gttttctgtg cgccgcttca ccggtatcag gtagcagtag    60
ctcgcaatat cagcaccaac agaaa    85

<210> SEQ ID NO 31
<211> LENGTH: 40
<212> TYPE: DNA
<213> ORGANISM: Artificial Sequence
<220> FEATURE:
<223> OTHER INFORMATION: sequence used in Example 2

<400> SEQUENCE: 31
tttctgttgg tgctgatatt gcgagctact gctacctgat    40

<210> SEQ ID NO 32
<211> LENGTH: 44
<212> TYPE: DNA
<213> ORGANISM: Artificial Sequence
<220> FEATURE:
<223> OTHER INFORMATION: sequence used in Example 2
<220> FEATURE:
<221> NAME/KEY: misc_feature
<222> LOCATION: (5)..(5)
<223> OTHER INFORMATION: n is uridine

<400> SEQUENCE: 32
gatcngaagc ggcgcacgaa aaacgctccg gagtttcacg ataa    44

<210> SEQ ID NO 33
<211> LENGTH: 85
<212> TYPE: DNA
<213> ORGANISM: Artificial Sequence
<220> FEATURE:
<223> OTHER INFORMATION: complementary sequence to SEQ ID NO:30 used in
      Example 2

<400> SEQUENCE: 33
tttctgttgg tgctgatatt gcgagctact gctacctgat accggtgaag cggcgcacga    60 aaacgctcc ggagtttcac gataa    85

<210> SEQ ID NO 34
<211> LENGTH: 77
<212> TYPE: DNA
<213> ORGANISM: Artificial Sequence
<220> FEATURE:
<223> OTHER INFORMATION: sequence used in Example 3 and 4

<400> SEQUENCE: 34
tttttttttt tttttttttt tttttttttt tttttttttt tttttttttt ggttgtttct    60
gttggtgctg atattgc    77

<210> SEQ ID NO 35
<211> LENGTH: 50
<212> TYPE: DNA
<213> ORGANISM: Artificial Sequence
<220> FEATURE:
<223> OTHER INFORMATION: sequence used in Example 3 and 4

<400> SEQUENCE: 35
gttttcgcat ttatcgtgaa acgctttcgc gttttcgtg cgccgcttca    50

<210> SEQ ID NO 36

-continued

```
<211> LENGTH: 54
<212> TYPE: DNA
<213> ORGANISM: Artificial Sequence
<220> FEATURE:
<223> OTHER INFORMATION: sequence used in Example 3
<220> FEATURE:
<221> NAME/KEY: misc_feature
<222> LOCATION: (5)..(5)
<223> OTHER INFORMATION: n is uridine

<400> SEQUENCE: 36
gatcngaagc ggcgcacgaa aaacgcgaaa gcgtttcacg ataaatgcga aaac      54

<210> SEQ ID NO 37
<211> LENGTH: 50
<212> TYPE: DNA
<213> ORGANISM: Artificial Sequence
<220> FEATURE:
<223> OTHER INFORMATION: sequence used in Examples 3 and 4

<400> SEQUENCE: 37
tttttttttt tttttttttt tttttttttt tttttttttt tttttttttt            50

<210> SEQ ID NO 38
<211> LENGTH: 49
<212> TYPE: DNA
<213> ORGANISM: Artificial Sequence
<220> FEATURE:
<223> OTHER INFORMATION: sequence used in Example 3

<400> SEQUENCE: 38
gaagcggcgc acgaaaaacg cgaaagcgtt tcacgataaa tgcgaaaac             49

<210> SEQ ID NO 39
<211> LENGTH: 29
<212> TYPE: DNA
<213> ORGANISM: Artificial Sequence
<220> FEATURE:
<223> OTHER INFORMATION: sequence used in Examples 3 and 4

<400> SEQUENCE: 39
gcaatatcag caccaacaga aacaacctt                                   29

<210> SEQ ID NO 40
<211> LENGTH: 970
<212> TYPE: PRT
<213> ORGANISM: Clostridium botulinum

<400> SEQUENCE: 40

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110
```

```
His Trp Ala Glu Lys Asn Ala Glu Thr Arg Val Glu Lys Gly
            115                 120                 125
Met Val Val Thr Gln Ala Thr Gly Asn Leu Ala Ile Gly Leu Phe Gln
130                 135                 140
His Asp Thr Asn Arg Asn Gln Glu Pro Asn Leu His Phe His Ala Val
145                 150                 155                 160
Ile Ala Asn Val Thr Gln Gly Lys Asp Gly Lys Trp Arg Thr Leu Lys
                165                 170                 175
Asn Asp Arg Leu Trp Gln Leu Asn Thr Thr Leu Asn Ser Ile Ala Met
            180                 185                 190
Ala Arg Phe Arg Val Ala Val Glu Lys Leu Gly Tyr Glu Pro Gly Pro
        195                 200                 205
Val Leu Lys His Gly Asn Phe Glu Ala Arg Gly Ile Ser Arg Glu Gln
    210                 215                 220
Val Met Ala Phe Ser Thr Arg Arg Lys Glu Val Leu Glu Ala Arg Arg
225                 230                 235                 240
Gly Pro Gly Leu Asp Ala Gly Arg Ile Ala Ala Leu Asp Thr Arg Ala
                245                 250                 255
Ser Lys Glu Gly Ile Glu Asp Arg Ala Thr Leu Ser Lys Gln Trp Ser
            260                 265                 270
Glu Ala Ala Gln Ser Ile Gly Leu Asp Leu Lys Pro Leu Val Asp Arg
        275                 280                 285
Ala Arg Thr Lys Ala Leu Gly Gln Gly Met Glu Ala Thr Arg Ile Gly
    290                 295                 300
Ser Leu Val Glu Arg Gly Arg Ala Trp Leu Ser Arg Phe Ala Ala His
305                 310                 315                 320
Val Arg Gly Asp Pro Ala Asp Pro Leu Val Pro Pro Ser Val Leu Lys
                325                 330                 335
Gln Asp Arg Gln Thr Ile Ala Ala Ala Gln Ala Val Ala Ser Ala Val
            340                 345                 350
Arg His Leu Ser Gln Arg Glu Ala Ala Phe Glu Arg Thr Ala Leu Tyr
        355                 360                 365
Lys Ala Ala Leu Asp Phe Gly Leu Pro Thr Thr Ile Ala Asp Val Glu
    370                 375                 380
Lys Arg Thr Arg Ala Leu Val Arg Ser Gly Asp Leu Ile Ala Gly Lys
385                 390                 395                 400
Gly Glu His Lys Gly Trp Leu Ala Ser Arg Asp Ala Val Val Thr Glu
                405                 410                 415
Gln Arg Ile Leu Ser Glu Val Ala Ala Gly Lys Gly Asp Ser Ser Pro
            420                 425                 430
Ala Ile Thr Pro Gln Lys Ala Ala Ser Val Gln Ala Ala Ala Leu
        435                 440                 445
Thr Gly Gln Gly Phe Arg Leu Asn Glu Gly Gln Leu Ala Ala Ala Arg
    450                 455                 460
Leu Ile Leu Ile Ser Lys Asp Arg Thr Ile Ala Val Gln Gly Ile Ala
465                 470                 475                 480
Gly Ala Gly Lys Ser Ser Val Leu Lys Pro Val Ala Glu Val Leu Arg
                485                 490                 495
Asp Glu Gly His Pro Val Ile Gly Leu Ala Ile Gln Asn Thr Leu Val
            500                 505                 510
Gln Met Leu Glu Arg Asp Thr Gly Ile Gly Ser Gln Thr Leu Ala Arg
        515                 520                 525
```

```
Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940
```

```
Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 41
<211> LENGTH: 55
<212> TYPE: DNA
<213> ORGANISM: Artificial Sequence
<220> FEATURE:
<223> OTHER INFORMATION: sequence used in Example 4
<220> FEATURE:
<221> NAME/KEY: misc_feature
<222> LOCATION: (1)..(5)
<223> OTHER INFORMATION: n is inosine

<400> SEQUENCE: 41
nnnnntgaag cggcgcacga aaacgcgaa agcgtttcac gataaatgcg aaaac          55
```